(12) United States Patent
Wang

(10) Patent No.: US 9,175,326 B2
(45) Date of Patent: Nov. 3, 2015

(54) TRANSGLYCOSYLATION ACTIVITY OF GLYCOSYNTHASE MUTANTS OF AN ENDO-BETA-N-ACETYLGLUCOSAMINIDASE (ENDO-D) FROM STREPTOCOCCUS PNEUMONIAE

(71) Applicant: UNIVERSITY OF MARYLAND, BALTIMORE, Baltimore, MD (US)

(72) Inventor: Lai-Xi Wang, Ellicott City, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 13/759,221

(22) Filed: Feb. 5, 2013

(65) Prior Publication Data

US 2013/0137857 A1 May 30, 2013

Related U.S. Application Data

(63) Continuation-in-part of application No. 13/411,733, filed on Mar. 5, 2012.

(60) Provisional application No. 61/597,468, filed on Feb. 10, 2012, provisional application No. 61/448,702, filed on Mar. 3, 2011.

(51) Int. Cl.
| | |
|---|---|
| *C12P 21/06* | (2006.01) |
| *C12P 21/08* | (2006.01) |
| *C12N 9/24* | (2006.01) |
| *A61K 39/00* | (2006.01) |
| *C07K 1/00* | (2006.01) |
| *C07K 14/00* | (2006.01) |
| *C07K 16/00* | (2006.01) |
| *C07K 17/00* | (2006.01) |
| *C12P 21/00* | (2006.01) |
| *C07K 16/28* | (2006.01) |

(52) U.S. Cl.
CPC .............. *C12P 21/005* (2013.01); *C07K 16/00* (2013.01); *C07K 16/2887* (2013.01); *C12N 9/2402* (2013.01); *C12Y 302/01096* (2013.01); *C07K 2317/41* (2013.01)

(58) Field of Classification Search
None
See application file for complete search history.

(56) References Cited

U.S. PATENT DOCUMENTS

| | | | |
|---|---|---|---|
| 2005/0064540 A1* | 3/2005 | Defrees et al. | ............... 435/68.1 |
| 2005/0159341 A1 | 7/2005 | Wang et al. | |
| 2005/0176642 A1 | 8/2005 | Wang et al. | |
| 2005/0244424 A1 | 11/2005 | Wang | |
| 2007/0224211 A1 | 9/2007 | Wang | |
| 2008/0138855 A1 | 6/2008 | Wang | |
| 2009/0117154 A1 | 5/2009 | Wang et al. | |
| 2010/0173323 A1 | 7/2010 | Strome et al. | |
| 2010/0221241 A1 | 9/2010 | DeVico et al. | |
| 2012/0226024 A1 | 9/2012 | Wang et al. | |

OTHER PUBLICATIONS

Fan et al. 'Remarkable transglycosylation activity of glycosynthase mutants of endo-D, an endo-p-N-acetylglucosaminidase from *Streptococcus pneumoniae*.' J. Biol. Chem. 287(14):11272-11281,2012.*
Abbott D. W., et al., (2009) *Streptococcus pneumoniae* endohexosaminidase D, structural and mechanistic insight into substrate-assisted catalysis in family 85 glycoside hydrolases. *J. Biol. Chem.* 284, 11676-11689.
Amin M. N., et al., (2011) Convergent synthesis of homogeneous Glc1Man9G1cNAc2 protein and derivatives as ligands of molecular chaperones in protein quality control. *J. Am. Chem. Soc.* 133, 14404-14417.
Collin M., et al., (2001) EndoS, a novel secreted protein from *Streptococcus pyogenes* with endoglycosidase activity on human IgG. *EMBO J.* 20, 3046-3055.
Collin M., et al., (2001) Effect of SpeB and EndoS from *Streptococcus pyogenes* on human immunoglobulins. *Infect. Immun.* 69, 7187-7189.
Fujita M., et al., (2001) A novel disaccharide substrate having 1,2-oxazoline moiety for detection of transglycosylating activity of endoglycosidases. *Biochim. Biophys. Acta* 1528, 9-14.
Fujita K., et al., (2001) Tryptophan-216 is essential for the transglycosylation activity of endo-β-N-acetylglucosaminidase A. *Biochem. Biophys. Res. Commun.* 283, 680-686.
Huang W., et al., (2009) Glycosynthases enable a highly efficient chemoenzymatic synthesis of N-glycoproteins carrying intact natural N-glycans. *J. Am. Chem. Soc.* 131, 2214-2223.
Huang W., et al., (2011) Unusual transglycosylation activity of *Flavobacterium meningosepticum* endoglycosidases enables convergent chemoenzymatic synthesis of core-fucosylated complex N-glycopeptides. *ChemBioChem.* 12, 932-941.
Jefferis R. (2009) Glycosylation as a strategy to improve antibody-based therapeutics. *Nat. Rev. Drug Discov.* 8, 226-234.
Kadowaki, S., et al., 4 (1991) Microbial endo-β-N-acetylglucosaminidases acting on complex-type sugar chains of glycoproteins. *J. Biochem.* 110, 17-21.
Kato T., et al., (2002) Identification of an endo-β-N-acetylglucosaminidase gene in *Caenorhabditis elegans* and its expression in *Escherichia coli*. *Glycobiology* 12, 581-587.
Li B., et al., (2005) Highly efficient endoglycosidase-catalyzed synthesis of glycopeptides using oligosaccharide oxazolines as donor substrates. *J. Am. Chem. Soc.* 127, 9692-9693.
Li B., et al., (2006) A highly efficient chemoenzymatic approach toward glycoprotein synthesis. *Org. Lett.* 8, 3081-3084.
Ling Z., et al., (2009) tThe x-ray crystal structure of an Arthrobacter protophormiae endo-β-N-acetylglucosaminidase reveals a (β/α)8 catalytic domain, two ancillary domains, and active site residues key for transglycosylation activity. *J. Mol. Biol.* 389, 1-9.

(Continued)

*Primary Examiner* — Nora Rooney
(74) *Attorney, Agent, or Firm* — Marianne Fuierer; Moore & Van Allen, PLLC

(57) ABSTRACT

The present invention provides for recombinant Endo-D and selected mutants that exhibit reduced hydrolysis activity and increased transglycosylation activity for the synthesis of glycoproteins wherein a desired sugar chain is added to a core fucosylated or nonfucosylated GlcNAc-protein acceptor by transglycosylation. Such recombinant Endo-D and selected mutants are useful for efficient glycosylation remodeling of IgG1-Fc domain.

11 Claims, 11 Drawing Sheets

(56) References Cited

OTHER PUBLICATIONS

Muramatsu H., et al., (2001) Molecular cloning and expression of endo-β-Nacetylglucosaminidase D, which acts on the core structure of complex type asparagine-linked oligosaccharides. *J. Biochem.* 129, 923-928.

Nimmerjahn F., et al., (2008) Anti-inflammatory actions of intravenous immunoglobulin. *Annu. Rev. Immunol.* 26, 513-533.

Ochiai H., et al., (2008) Expeditious chemoenzymatic synthesis of homogeneous N-glycoproteins carrying defined oligosaccharide ligands. *J. Am. Chem. Soc.* 130, 13790-13803.

Parsons T. B., et al., (2010) *Streptococcus pneumoniae* endohexosaminidase D: feasibility of using N-glycan oxazoline donors for synthetic glycosylation of a GlcNAc-asparagine acceptor. *Org. Biomol. Chem.* 8, 1861-1869.

Raju T. S., et al., (2006) Glycosylation in the Fc domain of IgG increases resistance to proteolytic cleavage by papain. *Biochem. Biophys. Res. Commun.* 341, 797-803.

Rao V., et al., (1999) Mutations of endo-β-N-acetylglucosaminidase H active site residues Asp-130 and Glu-132: activities and conformations. *Protein Sci.* 8, 2338-2346.

Rising T. W., et al., (2006) Endohexosaminidase M: exploring and exploiting enzyme substrate specificity. *ChemBioChem.* 7, 1177-1180.

Robbins, P.W., et al. (1984) Primary structure of the Streptomyces enzyme endo-β-N-acetylglucosaminidase H., *J. Biol. Chem.* 259, 7577-7583.

Schwarz F., et al., (2010) A combined method for producing homogeneous glycoproteins with eukaryotic N-glycosylation. *Nat. Chem. Biol.* 6, 264-266.

Takegawa K., et al., (1997) Cloning, sequencing, and expression of Arthrobacter protophormiae endo-β-N-acetylglucosaminidase in *Escherichia coli.* Arch. *Biochem. Biophys.* 338, 22-28.

Tarentino, A. L., et al., (1992) Multiple endoglycosidase (Endo) F activities expressed by *Flavobacterium meningosepticum.* Endo F1: molecular cloning, primary sequence, and structural relationship to Endo H., *J. Biol. Chem.* 267, 3868-3872.

Tarentino, A.L., et al., (1993) Multiple endoglycosidase F activities expressed by *Flavobacterium meningosepticum* endoglycosidases F2 and F3: molecular cloning, primary sequence, and enzyme expression. *J. Biol. Chem.* 268, 9702-9708.

Umekawa M., et al., (2008) Mutants of Mucor hiemalis endo-β-Nacetylglucosaminidase show enhanced transglycosylation and glycosynthase-like activities. *J. Biol. Chem.* 283, 4469-4479.

Umekawa M., et al., (2010) Efficient glycosynthase mutant derived from Mucor hiemalis endo-β-N-acetylglucosaminidase capable of transferring oligosaccharide from both sugar oxazoline and natural N-glycan. *J. Biol. Chem.* 285, 511-521.

Umekawa M., et al., (2010) Efficient transfer of sialo-oligosaccharide onto proteins by combined use of a glycosynthase-like mutant of *Mucor hiemalis* endoglycosidase and synthetic sialo-complex-type sugar oxazoline. *Biochim. Biophys. Acta* 1800, 1203-1209.

Van Roey P., et al., (1994) Crystal structure of endo-β-N-acetylglucosaminidase F1, an α/β-barrel enzyme adapted for a complex substrate. *Biochemistry* 33, 13989-13996.

Waddling C. A., et al., (2000) Structural basis for the substrate specificity of endo-β-N-acetylglucosaminidase F3. *Biochemistry* 39, 7878-7885.

Wang L. X., (2008) Chemoenzymatic synthesis of glycopeptides and glycoproteins through endoglycosidase-catalyzed transglycosylation. *Carbohydr. Res.* 343, 1509-1522.

Wang L. X., (2011) The amazing transglycosylation activity of endo-β-Nacetylglucosaminidases. *Trends Glycosci. Glycotechnol.* 23, 33-52.

Wei Y., et al., (2008) Glycoengineering of human IgG1-Fc through combined yeast expression and in vitro chemoenzymatic glycosylation. *Biochemistry* 47, 10294-10304.

Yamamoto K., et al., (1994) Novel specificities of *Mucor hiemalis* endo-β-Nacetylglucosaminidase acting complex asparagine-linked oligosaccharides. *Biosci. Biotechnol. Biochem.* 58, 72-77.

Yamamoto S., et al., (2005) Mutational studies on endo-β-N-acetylglucosaminidase D which hydrolyzes core portion of asparagine-linked complex type oligosaccharides. *Glycoconj. J.* 22, 35-42.

Yin J., et al., (2009) Structural basis and catalytic mechanism for the dual functional endo-β-N-acetylglucosaminidase A. PLoS One 4, e4658.

Zou G., et al., (2011) Chemoenzymatic synthesis and Fcγ receptor binding of homogeneous glycoforms of antibody Fc domain: presence of a bisecting sugar moiety enhances the affinity of Fc to FcγIIIa receptor. *J. Am. Chem. Soc.* 133, 18975-18991.

* cited by examiner

```
                                                                 322 324
Endo-A    EQEEDGSFPL------ADKLLEVADYYGFDGWFI QETEG----ADEG-TAEAMQAFLV  190
Endo-D    KQDADGSFPI------ARKLVDMAKYYGYDGYFI QETTG----DLVKPLGEKMRQFML  342
Endo-M    PLLNNTDDPMRLWSPYYADQLVAIAKHYGFDGWLF I CEFFPFPTNPKFKAEELAKFLH  199
                  *:   *:*..:*:* ***:.* *.::*     :*.:.* *

360         371
Endo-A    YLQEQKPEG---MHIMW DSMIDTGAIA QNHLTDRNKMYLQ-NGSTRVADSMFLNFWWR  246
Endo-D    YSKEYAAKVNHPIKYSW DAMTYNYGRY QDGLGEYNYQFMQPEGDKVPADNFFANFNWD  402
Endo-M    YFKEKLHNEIPGSQLIW DSMTNEGEIH QNQLTWKNELFFK-----NTDGIFLNYWWK  253
          * .*     .    : * *:*.: .   *.   .:: :: :     :*.:* **:*
```

Figure 1

B
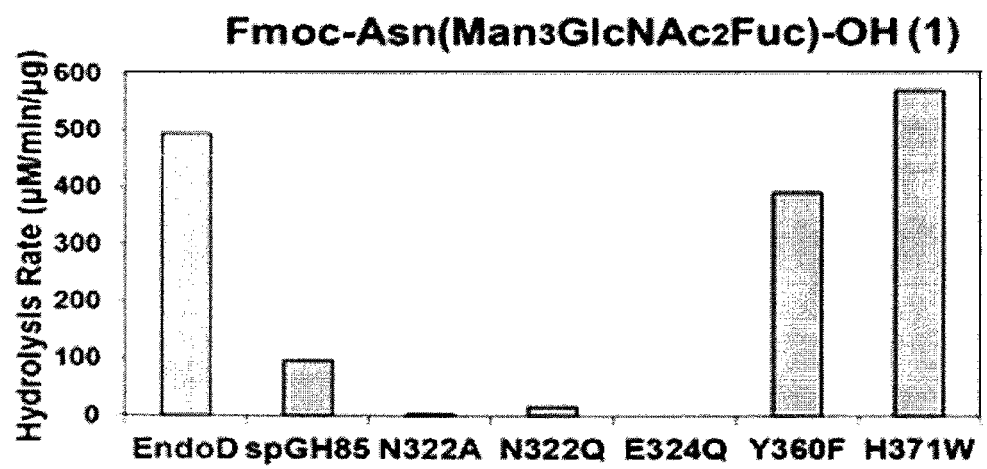
C
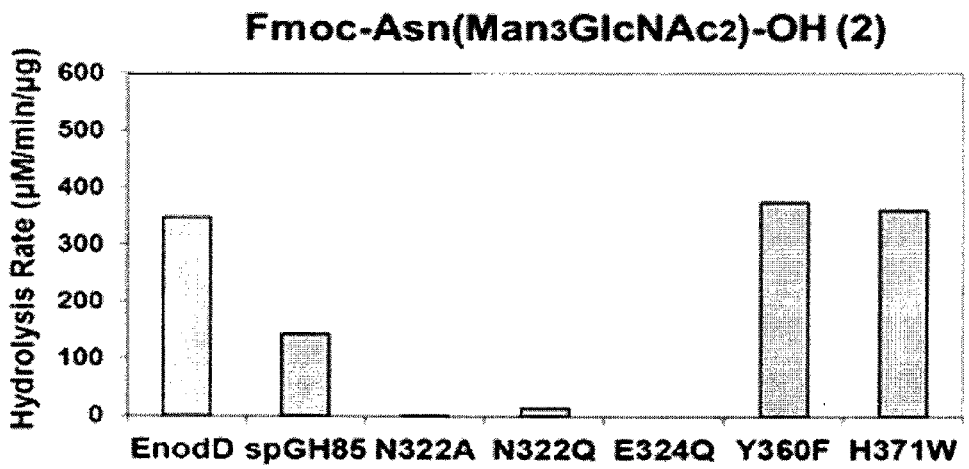
Figure 2 B and C

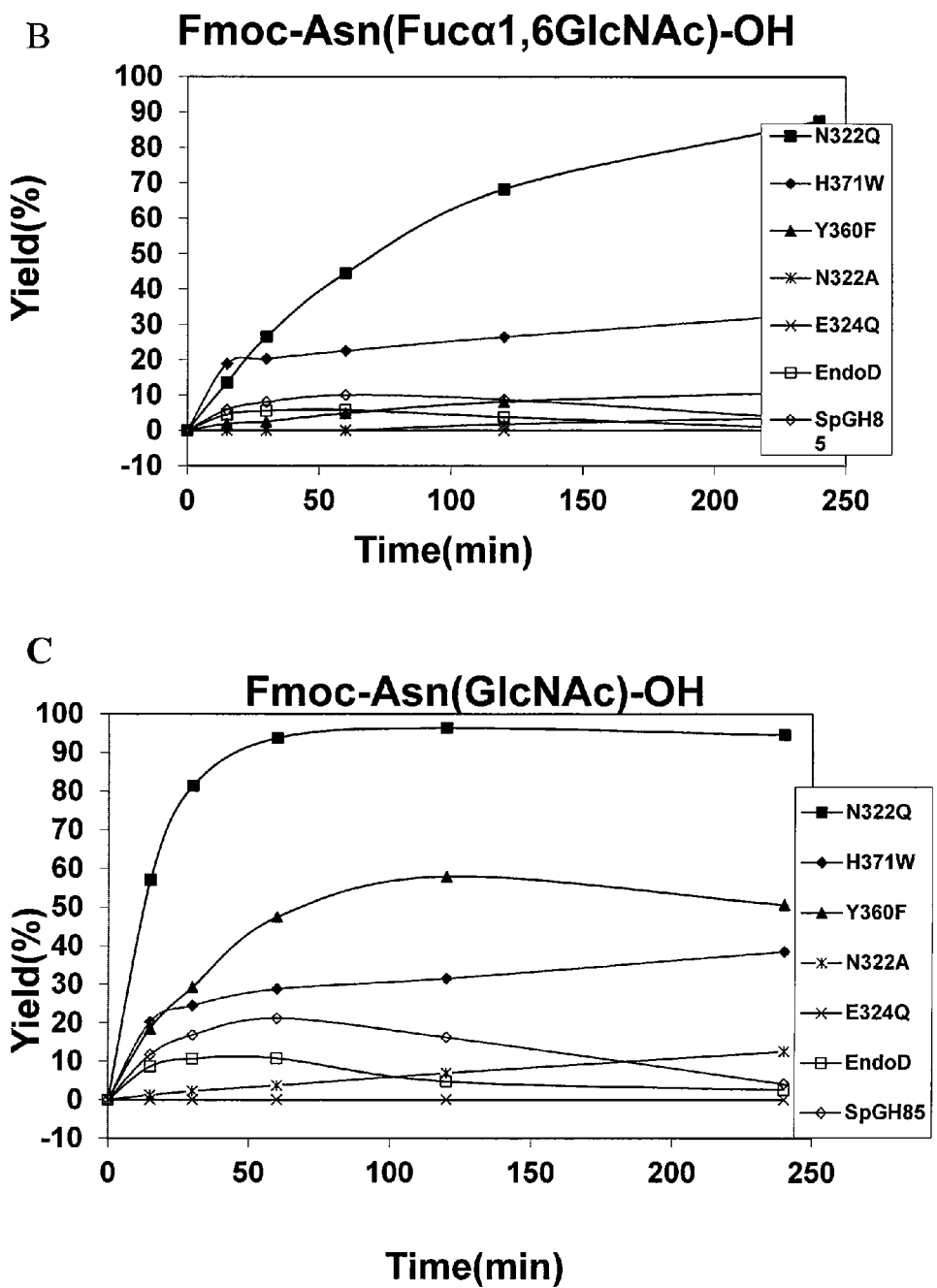
Figure 3 B and C

TRANSGLYCOSYLATION ACTIVITY OF GLYCOSYNTHASE MUTANTS OF AN ENDO-BETA-N-ACETYLGLUCOSAMINIDASE (ENDO-D) FROM STREPTOCOCCUS PNEUMONIAE

CROSS-REFERENCE TO RELATED APPLICATION

The application is a Continuation-in-Part application of and claims priority to co-pending U.S. patent application Ser. No. 13/411,733 filed on Mar. 5, 2012, which in turn claims priority to U.S. Provisional Application No. 61/448,702 filed on Mar. 3, 2011; and also claims priority to U.S. Provisional Application No. 61/597,468 filed on Feb. 10, 2012, the contents of all applications are hereby incorporated by reference herein for all purposes.

GOVERNMENT RIGHTS IN INVENTION

This invention was made with government support under Grant Numbers GM080374 and GM096973 awarded by the National Institutes of Health. The government has certain rights in the invention.

BACKGROUND OF THE INVENTION

1. Field of the Invention

The invention relates to glycoprotein synthesis, and more particularly, to the use of a recombinant Endo D, an Endo-β-N-acetylglucosaminidase, that possesses transglycosylation activity with sugar oxazoline with limited hydrolyzing activity thereby providing for efficient glycosylation remodeling of IgG1-Fc domain.

2. Description of the Related Art

Endo-β-N-acetylglucosaminidases (ENGases) are a class of glycoside hydrolases that hydrolyze the β-1,4-glycosidic bond in the N,N'-diacetylchitobiose core of N-glycans. The deglycosylation property of ENGases has been frequently used for structural and functional studies of glycoproteins. ENGases are classified into two classes of the glycoside hydrolase (GH) families in the CAZY database, GH18 and GH85. The commonly used bacterial endo-β-N-acetylglucosaminidases, such as Endo-H from *Streptomyces plicatus* (1) and Endo-$F_1$, Endo-$F_2$, and Endo-$F_3$ from *Flavobacterium meningosepticum* (2,3), belong to the GH18 family. In contrast, the GH85 family includes ENGases from both prokaryotes and eukaryotes, including Endo-M from *Mucor hiemalis* (4,5), Endo-A from *Arthrobacter protophormiae* (6), Endo-D from *Streptococcus pneumoniae* (7), and Endo-CE from *Caenorhabditis elegans* (8). In addition to the hydrolytic activity, some of the ENGases have been shown to possess transglycosylation activity, capable of transferring the released N-glycan to an alcoholic acceptor such as an N-acetylglucosamine (GlcNAc) moiety to reconstitute the natural β-1,4-glycosidic linkage. The transglycosylation activity of ENGases has attracted much attention in recent years for chemoenzymatic synthesis of oligosaccharides, glycopeptides, and glycoproteins (9, 10).

Structural and mechanistic studies on Endo-H (11), Endo-$F_1$ (12), Endo-$F_3$ (13), Endo-A (14, 15), and Endo-D (16) suggest that the ENGase-catalyzed N-glycan hydrolysis follows a substrate-assisted mechanism. In this mechanism, a general acid/base residue (Asp or Glu) first acts as a general acid to protonate the glycosidic oxygen. Upon activation, the 2-acetamide group of the (−1)GlcNAc in the substrate acts as a nucleophile to attack the anomeric center, resulting in the breakdown of the glycosidic bond with simultaneous formation of an oxazolinium ion intermediate. The oxazolinium intermediate then undergoes hydrolysis or transglycosylation via its reaction with a water molecule or an alcoholic acceptor activated by the general acid/base residue. These structural studies also identified another important residue, which is located at 1 or 2 amino acid residues upstream from the general acid/base catalytic residue. This key residue was shown to be an Asp residue for the GH18 ENGases (Endo-H, Endo-$F_1$, and Endo-$F_3$) or an Asn residue for the GH85 ENGases (Endo-A, Endo-M, and Endo-D), which was required for the proper orientation of the acetamide group to promote the oxazolinium ion formation. The essential role of this residue for hydrolysis was confirmed by the fact that mutation of this residue abolished the hydrolytic activity of ENGases (11-16).

These mechanistic and mutagenesis studies laid the basis for exploring synthetic sugar oxazolines as donor substrates for transglycosylation, which resulted in significant enhancement of the transglycosylation efficiency for glycopeptide and glycoprotein synthesis (17-22). Moreover, it was further demonstrated that novel glycosynthases could be generated by site-directed mutation at the critical Asn residue that promotes oxazolinium intermediate formation in hydrolysis (Asn-175 in Endo-M and Asn-171 in Endo-A). The resulting mutants such as EndoM-N175Q and EndoA-N171A were able to take the activated sugar oxazolines for transglycosylation with marginal or abolished hydrolytic activity on the transglycosylation product (23-29). These discoveries open a new avenue to glycoprotein synthesis and glycosylation remodeling and specifically, immunoglobulin G (IgG) antibodies.

A typical IgG antibody is composed of two light and two heavy chains that are associated with each other to form three major domains connected through a flexible hinge region: the two identical antigen-binding (Fab) regions and the constant (Fc) region. It is noted that there are heterogeneous glycosylation states of the human IgG when expressed in mammalian cell lines (e.g., CHO cell lines), and isolation of human IgG having a particular glycosylation state from this mixture is extremely difficult. Small amounts of impurities of a highly active species can dramatically interfere with the results and data interpretation. Generation of high-affinity mAbs to Fc receptors, such as the Fc γIIIa receptor, may overcome the problem of polymorphism of the Fcγ receptor variants, thus enhancing the clinical efficacy of therapeutic mAbs.

Endo-D from *S. pneumoniae* belongs to the glycoside hydrolase family 85 (GH85). However, in contrast to Endo-A and Endo-M that belong to the same family, Endo-D is able to hydrolyze fucosylated N-glycan core. Fairbanks and co-workers (30) first reported that Endo-D possessed transglycosylation activity, capable of using $Man_3GlcNAc$ oxazoline as donor substrate to glycosylate a GlcNAc acceptor, but the transglycosylation efficiency was very low.

In light of the above known activities of Endo D, it would be advantageous to provide a mutant Endo-D that exhibits reduced hydrolyzing activity with increased transglycosylating activity.

SUMMARY OF THE INVENTION

The present invention provides for recombinant Endo-D and selected mutants that exhibit reduced hydrolysis activity and increased transglycosylation activity for the synthesis of glycopeptides or glycoproteins wherein a desired sugar chain is added to a fucosylated and nonfucosylated GlcNAc-protein acceptor by transglycosylation. As such, the present invention allows for the synthesis and remodeling of therapeutic glycopeptides or glycoprotein drugs, glycoprotein hormones, cytokines, therapeutic antibodies thereby providing for certain biological activities, such as, prolonged half-life time in vivo, less immunogenicity, enhanced in vivo activity, increased targeting ability, and/or ability to deliver a therapeutic agent.

In one aspect, the present invention provides for transglycosylation activity of a recombinant Endo-β-N-acetylglucosamindase of *Streptococcus pneumoniae*, and mutants thereof, wherein the mutants have at least 95% homology thereto and exhibit transglycosylation activity on both fucosylated and nonfucosylated GlcNAc acceptors, wherein the endoglycosidases enable the transfer of an oligosaccharide (in the form of an activated sugar oxazoline) en bloc to a fucosylated or nonfucosylated GlcNAc-peptide acceptor to form a glycopeptide.

In another aspect, the present invention provides for Endo-D mutants that show remarkably enhanced transglycosylation efficiency due to the diminished or abrogated product hydrolytic activity. Mutants preferably include site-specific mutations including mutations at Asn-322 and Asn-324 of Endo-D including N322Q (SEQ ID NO:7), N322A (SEQ ID NO: 8) and E324Q (SEQ ID NO: 9).

In yet another aspect, the present invention provides efficient mutants of Endo-D, an endo-β-N-acetylglucosaminidase from *Streptococcus pneumoniae*, for transglycosylation with glycan oxazolines. The Endo-D mutants, including but not limited to, N322A (SEQ ID NO: 7) and N322Q (SEQ ID NO: 8), show remarkably enhanced transglycosylation to either core fucosylated or non-fucosylated GlcNAc acceptor.

In a further aspect, the present invention provides for a chemoenzymatic method for the preparation of a homogeneous fucosylated or nonfucosylated glycoprotein, comprising:
providing an acceptor selected from the group consisting of a core fucosylated GlcNAc-protein and nonfucosylated GlcNAc-protein; and
reacting the acceptor with a donor substrate including an activated oligosaccharide moiety, in the presence of Endo-D or mutants thereof to transfer the activated oligosaccharide moiety to the acceptor and yield the homogeneous core fucosylated or nonfucosylated glycoprotein.

In a still further aspect, the present invention provides a method for preparing a core-fucosylated glycoprotein having a predetermined oligosaccharide moiety, comprising:
providing a core-fucosylated acceptor protein comprising an asparagine-linked N-acetylglucosamine (GlcNAc) residue linked to a core fucosylated residue; and
enzymatically reacting the core-fucosylated acceptor protein with an activated oligosaccharide donor in the presence of Endoglycosidase-D N322Q (SEQ ID NO: 7) or N322A (SEQ ID NO: 8) mutant, wherein the activated oligosaccharide donor carries an oligosaccharide moiety comprising a predetermined number and type of sugar residues, such that, via an enzymatic reaction, the oligosaccharide moiety is covalently linked to the acceptor protein; thereby preparing the core-fucosylated glycoprotein having the predetermined oligosaccharide moiety.

In yet another aspect, the present invention provides for an activated oligosaccharide moiety, such as glycosyl fluoride, glycosyl azide or an aryl glycoside, as a donor substrate for the synthesis of homogeneous core-fucosylated glycopeptides or nonfucosylated glycoproteins. Preferably the activated oligosaccharide moiety is an oligosaccharide oxazoline.

In a further aspect, the present invention relates to a chemoenzymatic method for the preparation of a homogeneous fucosylated or nonfucosylated glycoprotein, said method comprising:
providing an acceptor selected from fucosylated GlcNAc protein or nonfucosylated GlcNAc protein; and
reacting the acceptor with a donor substrate in the presence of an Endo-D mutant, wherein the donor substrate comprises a predetermined oligosaccharide component with a defined number and type of sugar residues and specific linkage types, thereby providing the homogeneous fucosylated or nonfucosylated glycoprotein.

A core fucosylated GlcNAc containing protein is an alpha-1-6-fucosyl-GlcNAc-protein.

In a still further aspect, the present invention provides for a composition comprising at least one of the novel Endoglycosidase-D mutants selected from the group consisting of N322Q (SEQ ID NO:7), N322A (SEQ ID NO: 8) and E324Q (SEQ ID NO: 9).

In another aspect, the invention relates to a method of fucosylated glycopeptide or glycoprotein remodeling with an oligosaccharide having a predetermined oligosaccharide component with a defined number and type of sugar residues and with specific linkage types, the method comprising:
providing a glycopeptide or glycoprotein substrate carrying core fucosylated N-glycans having at least two GlcNAc residues;
treating the fucosylated glycopeptide or glycoprotein substrate with an endo-enzyme to hydrolyze the bond between the two GlcNAc residues positioned closest to the peptide thereby forming a fucosylated glycopeptide or glycoprotein substrate with a single GlcNAc-moiety; and
attaching the oligosaccharide to the single GlcNAc moiety in the presence of an Endo-D mutant having an amino acid sequence selected from the group consisting of SEQ ID NO: 7 and SEQ ID NO: 8, thereby adding a predetermined the oligosaccharide component.

In a further aspect, the invention relates to a method of fucosylated or nonfucosylated glycoprotein remodeling with an oligosaccharide having a predetermined oligosaccharide component with a defined number and type of sugar residues and with specific linkage types, the method comprising:
a. providing a fucosylated or nonfucosylated glycoprotein obtained from natural or recombined sources carrying heterogeneous N-glycans;
b. treating the fucosylated or nonfucosylated glycoprotein substrate with an endo-enzyme (a wild type endoglycosidase or a mutant endoglycosidase with efficient hydrolytic activity) to hydrolyze the bond between the two GlcNAc residues positioned closest to the peptide thereby forming a deglycosylated protein carrying the fucosylated or nonfucosylated GlcNAc disaccharide moiety at the original glycosylation site(s); and
c. attaching the pre-determined oligosaccharide to the GlcNAc residue to reconstitute the natural β-1,4-glycosidic bond through the transglycosylation with an endoglycosidase selected from Endo-D and its glycosythase mutants, thereby adding a predetermined the oligosaccharide component.

Applicable oligosaccharide oxazolines include, but not limited to, high-mannose type, hybrid type, and complex type N-glycan, as well as their selectively modified derivatives. Preferably, di-, tri-, tetra-, penta-, hexyl-, hepta-, octyl-, nona-, deca-, or undeca-saccharide oxazolines are utilized as donor substrates for a highly efficient chemoenzymatic synthesis of homogeneous fucosylated or nonfucosylated glycopeptides or glycoproteins.

In yet another aspect, the present invention relates to a method of synthesis of a modified antibody or fragment thereof, the method comprising;
a. using a naturally existing IgG antibody or a recombinant antibody or Fc domains carrying Fc N-glycans as precursors;
b. Fc deglycosylating using an endoglycosidase such an Endo-S to deglycosylate the Fc domain to form a GlcNAc-acceptor; wherein the GlcNAc moiety is positioned on the Fc region of the antibody and the GlcNAc moiety is either fucosylated or nonfucosylated; and
c. transglycosylating the GlcNAc moiety in the antibody with an oligosaccharide oxazoline having a predetermined number of sugar residues under the catalysis of an enzyme selected from the group consisting of Endo-D and mutants including SEQ ID NO: 7, SEQ ID NO: 8, SEQ ID NO: 4 and SEQ ID NO: 5 to form the modified antibody with the predetermined number of saccharides.

In a still further aspect, the invention relates to a method of synthesizing homogeneous fucosylated or nonfucosylated glycoprotein, the method comprising:
a. providing a heterogeneous fucosylated or nonfucosylated glycoprotein comprising different high mannose type N-glycans, wherein the heterogeneous fucosylated or nonfucosylated glycoprotein is from a natural source or produced from a wild type or engineered yeast system;
b. removing the different high mannose type N-glycans by an enzyme selected from the group consisting of Endo-H, Endo-S and Endo-A to form a fucosylated or nonfucosylated GlcNAc-containing protein;
c. providing a sugar containing oxazolines with a desired oligosaccharide component comprising a defined number and type of sugar residues in the chain; and
d. enzymatically transglycosylating with an endoglycosidase selected from the group consisting of Endo-D and mutants thereof, the fucosylated or nonfucosylated GlcNAc-containing protein with the sugar containing oxazoline thereby forming a homogeneous fucosylated or nonfucosylated glycoprotein having an extension of desired number of sugar residues.

It is envisioned that the oligosaccharide oxazoline having a predetermined oligosaccharide component with a defined number and type of sugar residues may further comprises an additional moiety or tag including, a therapeutic agent or drug such as for treating cancer, HIV or other viruses, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof.

As such, the present invention further provides a delivery device for delivering a drug having biological activity to treat a condition, the delivery device comprising: a remodeled fucosylated glycoprotein or glycopeptides having a predetermined sugar chain and a therapeutic agent or drug attached to the terminal sugar residue.

The present invention envisions modifying monoclonal antibodies related to HIV including, but not limited to 17b, 48d, A32, C11, 2G12, F240, IgG1b12, 19e, X5, TNX-355 and F91, all of which are commercially available.

Further antibodies related to cancer or other diseases may also be remodeled for individual fit to certain receptors thereby increasing biological activity, the monoclonal antibodies may include, but are not limited to, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101 (Aphton), volociximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), eraptuzumab (Immunomedics), MDX-010 (Medarex and BMS), MDX-060 (Medarex), MDX-070 (Medarex), matuzumab (Merck), CP-675,206 (Pfizer), CAL (Roche), SGN-30 (Seattle Genetics), zanolimumab (Serono and Genmab), adecatumumab (Sereno), oregovomab (United Therapeutics), nimotuzumab (YM Bioscience), ABT-874 (Abbott Laboratories), denosumab (Amgen), AM 108 (Amgen), AMG 714 (Amgen), fontolizumab (Biogen Idec and PDL BioPharm), daclizumab (Biogent Idec and PDL BioPharm), golimumab (Centocor and Schering-Plough), CNTO 1275 (Centocor), ocrelizumab (Genetech and Roche), HuMax-CD20(Genmab), belimumab (HGS and GSK), epratuzumab (Immunomedics), MLN1202 (Millennium Pharmaceuticals), visilizumab (PDL BioPharm), tocilizumab (Roche), ocrerlizumab (Roche), certolizumab pegol (UCB, formerly Celltech), eculizumab (Alexion Pharmaceuticals), pexelizumab (Alexion Pharmaceuticals and Procter & Gamble), abciximab (Centocor), ranibizimumab (Genetech), mepolizumab (GSK), TNX-355 (Tanox), or MYO-029 (Wyeth).

A still further aspect of the invention relates to a method of remodeling an antibody which initially includes a heterogeneous sugar chain, including polyclonal and monoclonal antibodies, the method comprising:
a. removing the heterogeneous sugar chain from the antibody with an endoglycosidase to leave a fucosylated- or nonfucosylated-GlcNAc moiety attached to an original glycosylation site; and
b. transferring a core oligosaccharide with at least one tag to the fucosylated- or -nonfucosylated GlcNAc moiety by an endoglycosidase catalyzed transglycosylation to yield a tagged antibody, wherein the endoglycosidase is selected from the group consisting of Endo-D and mutants thereof including SEQ ID NO: 7, SEQ ID NO: 8, SEQ ID NO: 4 and SEQ ID NO: 5.

The tag moiety may include, but is not limited to, antigens, therapeutic drugs such as for cancer or HIV, toxins, fluorescent probes, biotin, PEG species, lipids, or nucleotides.

In another aspect, the present invention provides for a method of treatment using a remodeled antibody having a desired glycosylation state in an amount sufficient to modulate biological activity in the treated subject.

Other aspects, features and embodiments of the invention will be more fully apparent from the ensuing disclosure and appended claims.

BRIEF DESCRIPTION OF THE FIGURES

FIG. 1 shows the alignment of amino acid sequence of catalytic core of Endo-D (SEQ ID NO: 10), Endo-A (SEQ ID NO: 11), and Endo-M (SEQ ID NO:12). Residues Asn-322, Glu-324, Tyr-360, and His-371 of Endo-D are highlighted in dark gray.

DETAILED DESCRIPTION OF THE INVENTION

Figure 2:
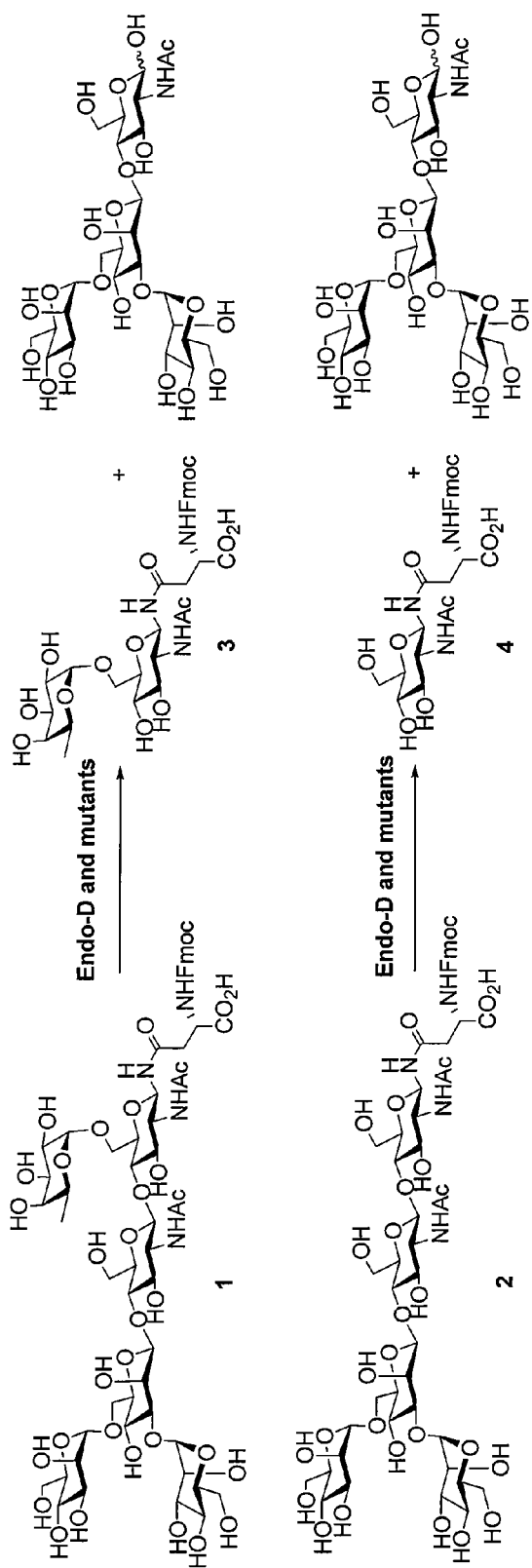
FIG. 2 shows the hydrolysis rate of Endo-D and its mutants using synthetic substrates. A, reaction scheme. B, hydrolysis rates of fucosylated substrate Fmoc-Asn(Man$_3$GlcNAc(Fucα1,6)GlcNAc)-OH (1). C, hydrolysis rate of nonfucosylated substrate Fmoc-Asn(Man$_3$GlcNAc$_2$)-OH (2). The hydrolysis rates were determined using 2.8 mM of each substrate and quantified by RP-HPLC.

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

It is understood that aspects of the present invention described herein include "consisting" and/or "consisting essentially of" aspects.

DEFINITIONS

As used in the specification herein, "a" or "an" may mean one or more. As used herein in the claim(s), when used in conjunction with the word "comprising", the words "a" or "an" may mean one or more than one. As used herein "another" may mean at least a second or more.

As used herein, "biological activity" refers to pharmacodynamic and pharmacokinetic properties including, for example, molecular affinity or resultant biochemical or physiological effect, receptor affinity or resultant biochemical or physiological effect, non-receptor affinity or biochemical or physiological effect, efficacy, bioavailability, absorption, distribution, metabolism, or elimination.

As used herein, "sugar" refers to an oxidized or unoxidized carbohydrate-containing molecule, including, but not limited to, a monosaccharide, disaccharide, trisaccharide, oligosaccharide, or polysaccharide, including, for example, N-acetylglucosamine, mannose, galactose, N-acetylneuraminic acid (sialic acid), glucose, fructose, fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer. Sugar further refers to, such molecules produced naturally, recombinantly, synthetically, and/or semi-synthetically.

As used herein, "homogenous" refers to core-fucosylated glycoproteins or nonfucosylated glycoproteins wherein the oligosaccharide component comprises at least 75%, more preferably at least 90%, and most preferably at least 95% of the same number and types of sugar residues.

As used herein, "protein" or "glycoprotein" is interchangeable with the term peptide and glycopeptide.

As used herein, "homology" refers to amino acid sequence having substantial identity or similarity between two polypeptides and having at least 90%, and more preferably at least 95% similarity to a reference polypeptide. For polypeptides, the length of comparison to obtain the above-described percent homologies between sequences will generally be at least 25 amino acids, alternatively at least 50 amino acids, more likely at least 100 amino acids, and most likely 200 amino acids or more. Substantially identity or homologous polypeptides include additions, truncations, internal deletions or insertions, conservative and non-conservative substitutions, or other modifications located at positions of the amino acid sequence which do not destroy the function of the endoglycosidase. Those of skill in the art will recognize the numerous amino acids that can be modified or substituted with other chemically similar residues without substantially altering activity.

As used herein, "modulates" refers to an increase or decrease in "biological activity", as defined above, when comparing to a glycosylation-engineered antibody of the present invention to a non-glycosylation-engineered antibody.

As used herein, "immunoglobulin molecule" or "antibodies," refers to molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including but not limited to Fab fragment(s) and Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

As used herein, with respect to antibodies, "substantially pure" means separated from those contaminants that accompany it in its natural state or those contaminants generated or used in the process of the obtaining the antibody. This term further includes the desired product having a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, and most preferably at least about 99%, by weight, of the desired antibody. A substantially pure antibody includes a naturally, recombinantly, or synthetically produced antibody.

As used herein, "therapeutically effective amount" refers to an amount that results in an improvement or remediation of the symptoms of the disease or condition.

Antigens useful for attachment as a tag to a modified fucosylated or nonfucosylated glycoprotein of the present invention and more preferably an antibody or fragment thereof may be a foreign antigen, an endogenous antigen, fragments thereof, or variants having the same functional activity.

As used herein, "endogenous antigen" refers to a protein or part thereof that is naturally present in the recipient animal cell or tissue, such as a cellular protein, an immunoregulatory agent, or a therapeutic agent.

As used herein, "foreign antigen" refers to a protein or fragment thereof, which is foreign to the recipient animal cell or tissue including, but not limited to, a viral protein, a parasite protein, an immunoregulatory agent, or a therapeutic agent.

The foreign antigen may be a protein, an antigenic fragment or antigenic fragments thereof that originate from viral and parasitic pathogens.

Alternatively, the foreign antigen may be encoded by a synthetic gene and may be constructed using conventional recombinant DNA methods; the synthetic gene may express antigens or parts thereof that originate from viral and parasitic pathogens. These pathogens can be infectious in humans, domestic animals or wild animal hosts.

The foreign antigen can be any molecule that is expressed by any viral or parasitic pathogen prior to or during entry into, colonization of, or replication in their animal host.

The viral pathogens, from which the viral antigens are derived include, but are not limited to, Orthomyxoviruses, such as influenza virus (Taxonomy ID: 59771); Retroviruses, such as RSV, HTLV-1 (Taxonomy ID: 39015) and HTLV-II (Taxonomy ID: 11909); Herpes viruses, such as EBV (Taxonomy ID: 10295), CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia Taxonomy ID: 10245); Rotavirus Taxonomy ID: 10912); and Parvoviruses, such as adeno-associated virus 1 (Taxonomy ID: 85106).

Examples of viral antigens include, but are not limited to, the human immunodeficiency virus antigens Nef (National Institute of Allergy and Infectious Disease HIV Repository Cat. #183; GenBank accession # AF238278), Gag, Env (National Institute of Allergy and Infectious Disease HIV Repository Cat. #2433; GenBank accession # U39362), Tat (National Institute of Allergy and Infectious Disease HIV Repository Cat. #827; GenBank accession # M13137), Rev (National Institute of Allergy and Infectious Disease HIV Repository Cat. #2088; GenBank accession # L14572), Pol (National Institute of Allergy and Infectious Disease HIV Repository Cat. #238; GenBank accession # AJ237568) and T cell and B cell epitopes of gp120; the hepatitis B surface antigen (GenBank accession # AF043578); rotavirus antigens, such as VP4 (GenBank accession # AJ293721) and VP7 (GenBank accession # AY003871); influenza virus antigens, such as hemagglutinin (GenBank accession # AJ404627); nucleoprotein (GenBank accession # AJ289872); and herpes simplex virus antigens, such as thymidine kinase (GenBank accession # AB047378).

The bacterial pathogens, from which the bacterial antigens are derived, include but are not limited to, *Mycobacterium* spp., *Helicobacter pylori*, *Salmonella* spp., *Shigella* spp., *E. coli*, *Rickettsia* spp., *Listeria* spp., *Legionella pneumoniae*, *Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borellia burgdorferi*, protective paracrystalline-surface-layer proteins of *Rickettsia prowazekii* and *Rickettsia typhi*, the listeriolysin (also known as "Llo" and "Hly") and/or the superoxide dismutase (also know as "SOD" and "p60") of *Listeria monocytogenes*; the urease of *Helicobacter pylori*, and the receptor-binding domain of lethal toxin and/or the protective antigen of *Bacillus* anthrax.

Example of antigens from biological weapons or pathogens include, but are not limited to, smallpox, anthrax, tularemia, plague, listeria, brucellosis, hepatitis, vaccinia, mycobacteria, coxsackievirus, tuberculosis, malaria, erhlichosis and bacterial meningitis.

The parasitic pathogens, from which the parasitic antigens are derived, include but are not limited to, *Plasmodium* spp., such as *Plasmodium falciparum* (ATCC#: 30145); *Trypanosome* spp., such as *Trypanosoma cruzi* (ATCC#: 50797); *Giardia* spp., such as *Giardia intestinalis* (ATCC#: 30888D); *Boophilus* spp.; *Babesia* spp., such as *Babesia microti* (ATCC#: 30221); *Entamoeba* spp., such as *Entamoeba histolytica* (ATCC#: 30015); *Eimeria* spp., such as *Eimeria maxima* (ATCC#40357); *Leishmania* spp., (Taxonomy ID: 38568); *Schistosome* spp., such as *Schistosoma mansoni* (GenBank accession # AZ301495); *Brugia* spp., such as *Brugia malayi* (GenBank accession # BE352806); *Fascida* spp., such as *Fasciola hepatica* (GenBank accession # AF286903); *Dirofilaria* spp., such as *Dirofilaria immitis* (GenBank accession # AF008300); *Wuchereria* spp., such as *Wuchereria bancrofti* (GenBank accession # AF250996); and *Onchocerca* spp; such as *Onchocerca volvulus* (GenBank accession # BE588251).

Examples of parasite antigens include, but are not limited to, the pre-erythrocytic stage antigens of *Plasmodium* spp. such as the circumsporozoite antigen of *P. falciparum* (Gen- Bank accession # M22982) *P. vivax* (GenBank accession # M20670); the liver stage antigens of *Plasmodium* spp, such as the liver stage antigen 1 (as referred to as LSA-1; GenBank accession # AF086802); the merozoite stage antigens of *Plasmodium* spp; such as the merozoite surface antigen-1 (also referred to as MSA-1 or MSP-1; GenBank accession # AF199410); the surface antigens of *Entamoeba histolytica*, such as the galactose specific lectin (GenBank accession # M59850) or the serine rich *Entamoeba histolytica* protein; the surface proteins of *Leishmania* spp, such as 63 kDa glycoprotein (gp63) of *Leishmania major* (GenBank accession # Y00647 or the 46 kDa glycoprotein (gp46) of *Leishmania major*; paramyosin of *Brugia malayi* (GenBank accession # U77590; the triose-phosphate isomerase of *Schistosoma mansoni* (GenBank accession # W06781; the secreted globin-like protein of *Trichostrongylus colubriformis* (GenBank accession # M63263; the glutathione-S-transferases of *Fasciola hepatica* (GenBank accession # M77682; *Schistosoma bovis* (GenBank accession # M77682); *S. japonicum* (GenBank accession # U58012; and KLH of *Schistosoma bovis* and *S. japonicum* (Bashir, et al., supra).

Examples of tumor specific antigens include prostate specific antigen (PSA), TAG-72 and CEA; human tyrosinase (GenBank accession # M27160); tyrosinase-related protein (also referred to as TRP; GenBank accession # AJ132933); and tumor-specific peptide antigens.

Examples of transplant antigens include the CD3 molecule on T cells and histocompatibility antigens such as HLA A, HLA B, HLA C, HLA DR and HLA.

Examples of autoimmune antigens include IAS β chain, which is useful in therapeutic vaccines against autoimmune encephalomyelitis (GenBank accession # D88762); glatamic acid decarboxylase, which is useful in therapeutic vaccines against insulin-dependent type 1 diabetes (GenBank accession # NM013445); thyrotropin receptor (TSHr), which is useful in therapeutic vaccines against Grave's disease (GenBank accession # NM000369) and tyrosinase-related protein 1, which is useful in therapeutic vaccines against vitiligo (GenBank accession # NM000550).

HIV drugs that may be used in the construction of the tagged antibodies or fragments thereof include, but are not limited to antiviral agents such as nucleoside RT inhibitors, CCR5 inhibitors/antagonists, viral entry inhibitors and their functional analogs. Specifically, an antiviral agent may nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies; and viral entry inhibitors, such as Fuzeon (T-20) (enfuvirtide), NB-2, NB-64, T-649, T-1249, SCH-C, SCH-D, PRO 140, TAK 779, TAK-220, RANTES analogs, AK602, UK-427, 857; and functional analogs or equivalents thereof.

It is envisioned that many different fucosylated glycoproteins and nonfucosylated glycoproteins can be modified according to the methods of the present invention or used as a therapeutic agent for conjugation to a terminal sugar including but not limited to, adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives; bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. C SF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides; endotherins; enkephalins; enkephalin derivatives; epidermal growth factor (EGF); erythropoietin (EPO); follicle-stimulating hormone (FSH); gallanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and .alpha. and .beta. subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha- beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyl-dipeptide; nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide; and vasopressin.

Fucosylated and nonfucosylated glycoproteins are important classes of biomolecules that play crucial roles in many biological events such as cell adhesion, tumor metastasis, pathogen infection, and immune response. As indicated previously herein, a major problem in structural and functional studies of fucosylated or nonfucosylated glycoproteins is their structural microheterogeneity. Natural and recombinant core fucosylated or nonfucosylated glycoproteins are typically produced as a mixture of glycoforms that differ only in the structure of the pendent oligosaccharides.

The remodeled glycoproteins, such as antibodies can be subjected to any further structural modifications that are necessary or desired, including, without limitation, glycosyl transfer, and selective ligation (e.g., click chemistry, Staudinger reaction, etc.) to introduce the additional functional groups or tags. The functional groups can be of any suitable type, including, without limitation, toxins, special antigens (such as alpha-Gal), radioactive species, photoactive species, PEGs, etc. The glycoprotein can be catalytically reacted in a "click chemistry" cycloaddition reaction of the azide functionality of the glycoprotein with an alkyne bearing the functional moiety of interest. The azido and alkyne functional groups can be switched in the respective ligation components, and the glycoprotein can be functionalized with an alkynyl functionality and reacted with an azide-functionalized compound including the moiety of interest. It will also be appreciated that other ligation pairs can be devised for the click chemistry reaction.

The fucosylated and nonfucosylated glycoproteins, produced according to the methods described herein, can be used for diagnosis and therapeutics. Approximately two-thirds of therapeutic proteins used on the market and/or currently in clinical trials are glycoproteins. However, the structural heterogeneity in different glycoforms of natural and recombinant glycoproteins presents a major barrier in developing glycoprotein-based drugs, as different glycoforms may have different biological activities and controlling glycosylation to a homogeneous glycoform is extremely difficult during expression. The previous discovery of the transglycosylation activity of a class of endoglycosidases represents a major advance in the field for glycosylation engineering to enhance glycoproteins' therapeutic and diagnostic potentials and the Endo-D mutants of the present invention are able transglycosylate fucosylated and nonfucosylated natural and recombinant glycoproteins.

The features and advantages of the present invention are more fully shown by the following non-limiting examples.

EXAMPLES

Cloning and Expression of Endo-D and Selected Mutants

The full-length Endo-D is a large protein consisting of 1646 amino acid residues (SEQ ID NO: 1) ($M_r$=178,000), which is encoded by a gene of 4941 bp in length (SEQ ID NO:2)(7,35). It has been previously reported that a truncated form (a.a. 135-1047) of the wild type Endo-D, in which 134 and 599 amino acids from the N and C terminus were removed, respectively, still retains enzymatic activity comparable with the full-length wild type enzyme (35). In the present invention, this truncated form of enzyme (hereafter called Endo-D) (SEQ ID NO 3) was selected as the template for site-directed mutagenesis because of its much smaller size than the full-length wild type Endo-D, although a full length form may be used if with the correct mutations in the full length at Asn-322 (N322Q (SEQ ID NO: 4) and N322A (SEQ ID NO: 5)) and Glu-324 (E324Q) (SEQ ID NO: 6).

Also an extensively truncated Endo-D form (amino acid sequence 159-807) was cloned for comparative studies. This further truncated form, the catalyzed domain of Endo-D termed spGH85, was recently expressed and used for x-ray crystallographic analysis and for transglycosylation study (16,30).

Figure 6:
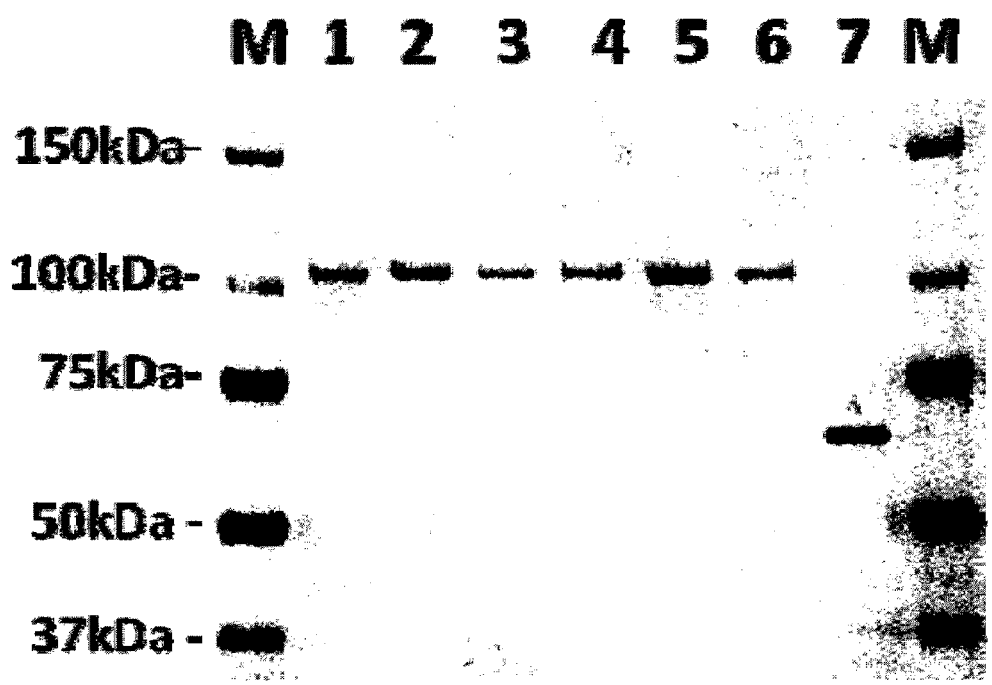
FIG. 6 shows SDS-PAGE of Endo-D and mutants. Lane 1, Endo-D (a.a. 135-1047); Lane 2, N322A; Lane 3, N322Q; Lane 4, E324Q; Lane 5, Y360F; Lane 6, H371W; Lane 7, spGH85 (a.a. 159-807).

Sequence alignment of Endo-D (SEQ ID NO: 11), Endo-A (SEQ ID NO: 10), and Endo-M (SEQ ID NO: 12) led to the identification of several interesting residues that are likely to be directly involved in the substrate-assisted mechanism of catalysis by the GH85 enzymes (FIG. 1). These include Asn-322, Glu-324, Tyr-360, and His-371 of Endo-D. The Asn-322 residue corresponded to the Asn-171 in Endo-A and Asn-175 in Endo-M, which were previously identified as the key residue for orientating and promoting oxazoline formation in glycosidic bond hydrolysis (14, 15, 23, 24). The Glu-324 residue was equivalent to the Glu-173 of Endo-A and the Glu-177 in Endo-M, which was identified as the general acid/base residue in the catalysis (14, 15, 23, 24). The recent x-ray structural study of spGH85 also confirmed the essential roles of Asn-322 and Glu-324 in the substrate-assisted mechanism of catalysis (the two residues were numbered as Asn-335 and Glu-337 in the x-ray crystal structure) (16). The Tyr-360 residue in Endo-D was aligned with Tyr-205 in Endo-A and Tyr-217 in Endo-M, mutation of which to a Phe residue was previously shown to significantly enhance the transglycosylation efficiency (23). The alignment of His-371 in Endo-D to the residues Trp-216 and Trp-228 in Endo-A and Endo-M, respectively, came as a surprise as Trp-216 in Endo-A was shown to be essential for transglycosylation but dispensable for hydrolytic activity (36). Accordingly, five mutants (N322Q (SEQ ID NO: 7), N322A (SEQ ID NO: 8), E324Q (SEQ ID NO: 9), Y360F (SEQ ID NO: 13), and H371W (SEQ ID NO: 14)) were generated by site-directed mutagenesis on these four sites to probe the effects of these mutations on the transglycosylation activity of Endo-D. The genes encoding Endo-D (a.a. 135-1047, (SEQ ID NO: 3)) and spGH85 (a.a. 159-807, SEQ ID NO: 15)) were amplified from the genomic DNA of *S. pneumoniae* by PCR and cloned into the expression vector, pET28a. Endo-D mutants were created on the pET28a-EndoD template (encoding a.a. 135-1047) using the GENEART site-directed mutagenesis kit by designing appropriate pairs of primers. Endo-D, spGH85, and the mutants were then overproduced in the transformed *E. coli* strain BL21 (DE3) and purified to homogeneity on a nickel affinity column. The Endo-D (a.a. 135-1047) and its mutants appeared as a single band at ~100 kDa (FIG. 6, lanes 1 to 6), which was in good agreement with the expected molecular weight (calculated, $M_r$=102,000). The extensively truncated Endo-D fragment, spGH85, appeared as a single band at ~73 kDa (FIG. 6, lane 7) which was consistent with the calculated molecular mass ($M_r$=74,500).

Hydrolytic Activity of Endo-D and its Mutants

Two synthetic substrates were used to assess the hydrolytic activity of the recombinant enzymes: the core-fucosylated N-pentasaccharide derivative (1) and the nonfucosylated derivative (2) (FIG. 2A). An Fmoc tag was introduced to the Asn residue to facilitate HPLC monitoring of the enzymatic reactions. It was found that the spGH85, an extensively truncated form (a.a. 159-807), was much less active than Endo-D in hydrolyzing the core-fucosylated substrate (1) (FIG. 2B). The hydrolysis rate of Endo-D was about 4-fold lower than that of spGH85, indicating a loss of ~80% activity due to the further deletions of amino acid residues from the N and C terminus. This result is consistent with a previous study indicating that although the Endo-D (a.a. 135-1047) retained activity comparable with the full-length wild type enzyme, the further truncated Endo-D fragments (a.a. 1-966 and a.a. 201-1646) almost lost all the hydrolytic activity on the fucosylated N-pentasaccharide core (35). The N322Q (SEQ ID NO: 7), N322A (SEQ ID NO: 8), and E324Q (SEQ ID NO: 9) mutants showed no or only residual hydrolytic activity, confirming the crucial role of these two residues for hydrolysis. In comparison with wild type Endo-D, the Y360F mutant demonstrated a decreased hydrolytic activity, whereas the H371W mutant showed a slightly enhanced hydrolytic activity on the core-fucosylated substrate (1) (FIG. 2B). When the nonfucosylated substrate (2) was used as the substrate, the difference in activity between Endo-D and spGH85 was much smaller than that for the fucosylated substrate (1), whereas the Y360F and H371W mutants showed about the same activity as the Endo-D itself (FIG. 2C). On the other hand, the mutants N322Q and N322A demonstrated only marginal activity on substrate (2), and the E324Q did not show any detectable activity on substrate (2). These data again confirm the critical roles of the two residues for catalyzing the hydrolysis.

Transglycosylation Activity of Endo-D, spGH85, and Selected Endo-D Mutants

To assess the transglycosylation activities of Endo-D and its mutants, the transglycosylation reaction was performed using Man₃GlcNAc-oxazoline (5) as the donor substrate and Fmoc-Asn(Fucα1,6GlcNAc)-OH (3) and Fmoc-Asn (GlcNAc)-OH (4) as the acceptor substrates, respectively (FIG. 3A). The enzymatic reactions with Endo-D, spGH85, and the mutants were carried out under the same conditions (phosphate buffer, 50 mM, pH 7.5, donor/acceptor, 10:1).

Figure 3:
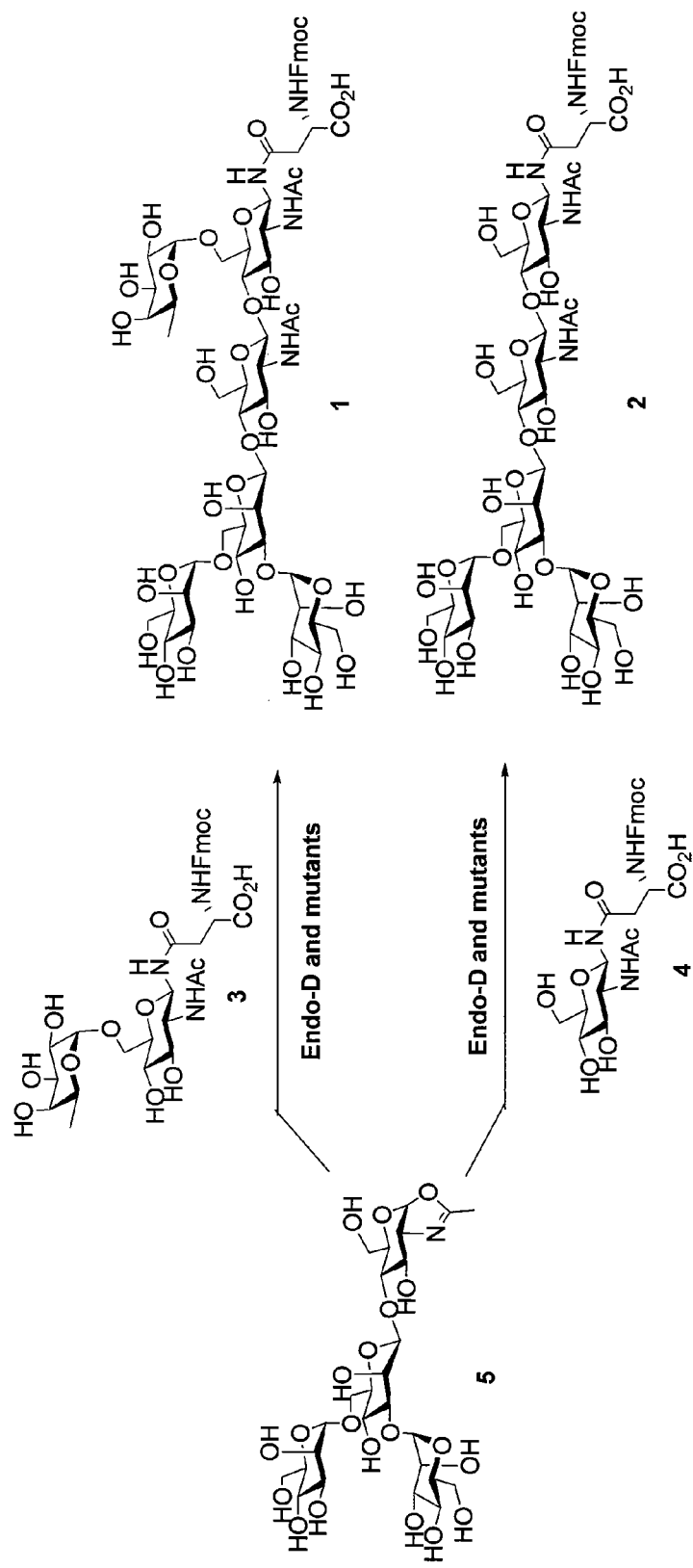
FIG. 3 shows the transglycosylation activity of Endo-D and mutants. A, reaction scheme. B, Fmoc-Asn(Fucα1,6GlcNAc)-OH (3) as the acceptor. C, Fmoc-Asn(GlcNAc)-OH (4) as the acceptor. Square, N322Q; diamond, H371W; triangle, Y360F; star, N322A; cross, E324Q; open square, Endo-D; open diamond, spGH85. The transglycosylation reaction was carried out using 5 mM Man$_3$GlcNAc-oxazoline as donor and 0.5 mM of each acceptor. The yields were calculated by the ratio of product/acceptor in RP-HPLC.

The transglycosylation reactions were monitored by HPLC analysis, and the yield was calculated on the basis of conversion of the acceptor substrate to the product (FIGS. 3 B and C). The Endo-D and spGH85 showed only low transglycosylation efficiency for both the fucosylated and the nonfucosylated GlcNAc acceptors (3 and 4), and the transglycosylation product was gradually hydrolyzed (FIGS. 3 B and C). In comparison, Endo-D and spGH85 showed a higher efficiency for transglycosylation on the GlcNAc acceptor (4) than the fucosylated GlcNAc acceptor (3). The transglycosylation of Endo-D on the fucosylated acceptor was marginal (less than 5% at the maximum under the assay conditions), which is consistent with our previous observations on wild type Endo-D (31). The extensively truncated enzyme, spGH85, gave a maximal yield of 20% when GlcNAc acceptor was used, which was similar to the previously reported results (30), whereas the less truncated enzyme (Endo-D) gave a maximal yield of 11%. In both cases, the product was hydrolyzed at the end. The Y360F mutant showed an enhanced transglycosylation activity and reduced product hydrolysis activity in comparison with Endo-D. The H371W mutant also demonstrated significantly enhanced transglycosylation efficiency, indicating that changing the His-371 to a Trp residue, as found at the equivalent position in Endo-A and Endo-M, did enhance the transglycosylation activity. Nevertheless, the Y360F and H371W mutants would still gradually hydrolyze the product given a prolonged time (data not shown). The E324Q mutant did not show any transglycosylation activity under the reaction condition, indicating the critical role of the Glu-324 residue for both hydrolysis and transglycosylation. The N322A mutant showed a moderate transglycosylation activity but, in contrast to Y360F and H371W, the N322A mutant proceeded with a steady increase of the transglycosylation yield without product hydrolysis even when the reaction was extended for 20 h (data not shown). The N322Q mutant demonstrated the highest transglycosylation activity, reaching 90% yield at 4 h for the fucosylated GlcNAc acceptor (3) (FIG. 3B) and at 1 h for the nonfucosylated GlcNAc acceptor (4) (FIG. 3C). N322A and N322Q thus act as typical glycosynthases that take the activated sugar oxazoline for transglycosylation but lack the activity to hydrolyze the product. The N322A and N322Q mutants represent the first glycosynthases that can use an α-1,6-fucosylated GlcNAc moiety as acceptor for transglycosylation to form core-fucosylated N-glycopeptides. Interestingly, Endo-D and its mutants so far tested demonstrated much higher transglycosylation efficiency with the nonfucosylated acceptor (4) than the corresponding fucosylated acceptor (3). In particular, N322Q showed extraordinarily high transglycosylation efficiency.

Kinetic Studies on Transglycosylation by N322A and N322Q Mutants

The initial transglycosylation activity screening indicated that the N322Q and N322A mutants were two promising glycosynthases capable of catalyzing transglycosylation but having no or only residual product hydrolysis activity. In addition, the N322Q mutant showed apparently much higher transglycosylation initial rate than the N322A mutant. To understand the mechanism behind the observed kinetic difference of N322A and N322Q mutants, the kinetic parameters of the transglycosylation catalyzed by the two mutants was determined. The results were summarized in Tables 1 and 2, as shown below. It was found that N322Q and N322A had a similar $K_m$ value (0.5-0.6 mM) for the donor substrate, Man₃GlcNAc-oxazoline, suggesting that both mutants have about the same affinity for the donor substrate. However, the $k_{cat}$ of N322Q was remarkably higher (over 48-fold) than that of N322A for the donor substrate (Table 1). Comparison of the kinetic data for the fucosylated and nonfucosylated GlcNAc acceptors (3 and 4) also revealed several interesting points (Table 2). The $K_m$ of N322Q for the fucosylated acceptor (3) was 24-fold higher than that for the nonfucosylated substrate (4), whereas its $k_{cat}$ for the fucosylated acceptor (3) was about 2-fold of that of the nonfucosylated acceptor (4). These data suggest that N322Q mutant has a much lower affinity for the fucosylated GlcNAc acceptor. As a result, the transglycosylation efficiency of N322Q on the nonfucosylated substrate (4) was about 10-fold higher than that on the fucosylated substrate (3), as estimated by the $k_{cat}/K_m$ values (8.7 mM⁻¹s⁻¹ for 4 and 0.77 mM⁻¹s⁻¹ for 3, respectively). The enhanced catalytic efficiency of N322Q for the nonfucosylated substrate mainly comes from the dramatic enhanced affinity of N322Q for the nonfucosylated substrate. In contrast, the N322A had similar $k_{cat}$ and $K_m$ values for both fucosylated and nonfucosylated GlcNAc acceptors. The catalytic efficiency of N322A on the nonfucosylated substrate (4) was about 2-fold higher than that of the fucosylated substrate (3). By a cross comparison of the two mutants, the N322Q mutant was much more efficient than the N322A mutant for both types of substrates. The catalytic efficiency (as estimated by the $k_{cat}/K_m$ values) of N322Q is 27-fold higher than that of the N322A mutant for the fucosylated substrate (3), which was mainly contributed from the much higher turnover rate ($k_{cat}$) of the N322Q mutant. The catalytic efficiency of N322Q was about 90-fold higher that of N322A mutant for the nonfucosylated substrate (4), which was contributed by both the higher turnover rate and the higher affinity of N322Q than that of the N322A mutant. Taken together, these data suggest that the N322Q mutant is a superior glycosynthase for the synthesis of both core-fucosylated and nonfucosylated glycopeptides or glycoproteins.

TABLE 1

Kinetic parameters on the donor substrate for the transglycosylation catalyzed by Endo-D mutants
Fmoc-Asn(Fucα1,6GlcNAc)-OH was used as acceptor substrate.

| Mutant | Man₃GlcNAc-oxazoline (5) | | |
|---|---|---|---|
| | $k_{cat}{}^a$ s⁻¹ | $K_m{}^a$ mm | $k_{cat}/K_m$ mm⁻¹s⁻¹ |
| N322Q | 10.17 ± 0.18 | 0.50 ± 0.07 | 20.4 |
| N322A | 0.21 ± 0.01 | 0.67 ± 0.13 | 0.31 |

$^a$The $k_{cat}$ and $K_m$ values represent mean ± S.D. (n = 3).

TABLE 2

Kinetic parameters on the acceptor substrates for the transglycosylation catalyzed by Endo-D mutants
Man₃GlcNAc-oxazoline was used as donor substrate.

| | GlcNAc(Fuc)AsnFmoc (3) | | | GlcNAcAsnFmoc (4) | | |
|---|---|---|---|---|---|---|
| Mutant | $k_{cat}^{a}$ $s^{-1}$ | $K_m^{a}$ mM | $k_{cat}/K_m$ $mM^{-1} s^{-1}$ | $k_{cat}^{a}$ $s^{-1}$ | $K_m^{a}$ mM | $k_{cat}/K_m$ $mM^{-1} s^{-1}$ |
| N322Q | 14.32 ± 0.98 | 18.51 ± 2.43 | 0.77 | 6.37 ± 0.43 | 0.73 ± 0.24 | 8.7 |
| N322A | 0.24 ± 0.05 | 8.51 ± 4.16 | $2.86 \times 10^{-2}$ | 0.5 ± 0.06 | 5.22 ± 1.5 | $9.6 \times 10^{-2}$ |

$^{a}$The $k_{cat}$ and $K_m$ values represent mean ± S.D. (n = 3).

Glycosylation Engineering of IgG1-Fc Using Endo-D Mutant

Figure 4:
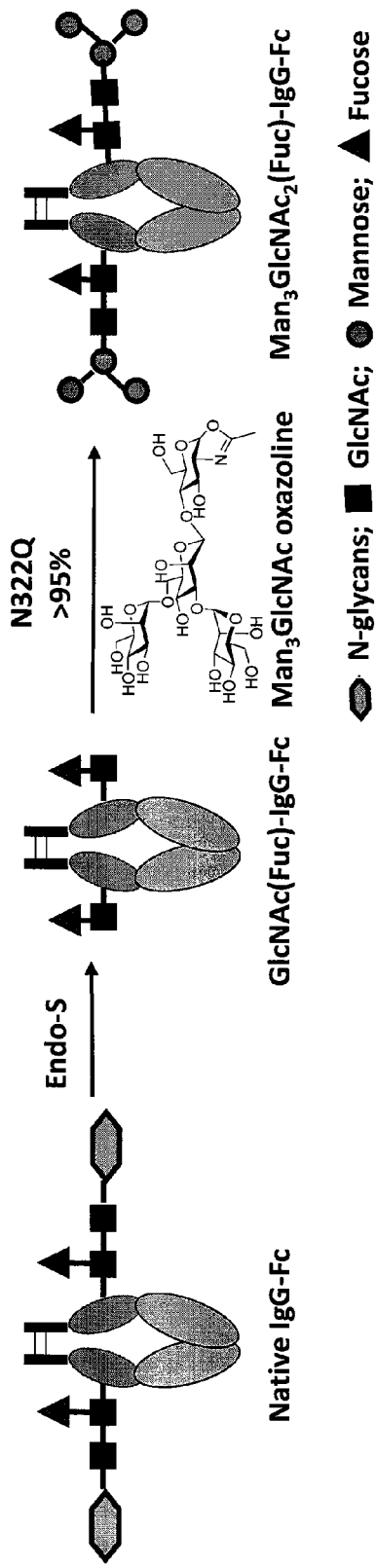
FIG. 4 shows the glycosylation remodeling of IgG-Fc through transglycosylation with Endo-D mutants.
Figure 5:
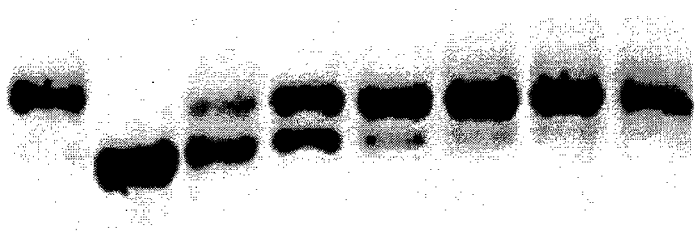
FIG. 5 shows the analysis of IgG-Fc glycosylation remodeling. The N322Q-catalyzed transglycosylation reaction was carried out using Man$_3$GlcNAc-oxazoline (5) as donor substrate and (Fucα1,6)GlcNAc-Fc as acceptor substrate. A, SDS-PAGE analysis. Lane 1, native Fc; lane 2, (Fucα1,6)GlcNAc-Fc; lanes 3-8, monitoring of the transglycosylation reaction (15 min-5 h). B, ESI-MS spectrum of the intact native Fc dimer (calculated for nonglycosylated IgG-Fc dimer, M$_r$=49,896. found (m/z), 52,763 (G0F homodimer), 52,925 (G0F/G1F heterodimer), 53,084 (G1F homodimer), and 53,400 (G2F homodimer) (deconvoluted data)). C, ESI-MS spectrum of (Fucα1,6)GlcNAc-Fc (calculated, M$_r$=50,594. found (m/z), 50,573 (deconvoluted data)). D, ESI-MS spectrum of transglycosylation product Man$_3$GlcNAc(Fucα1,6)GlcNAc-Fc (calculated, M$_r$=51,951. found (m/z), 51,946 (deconvoluted data)).
Figure 5:
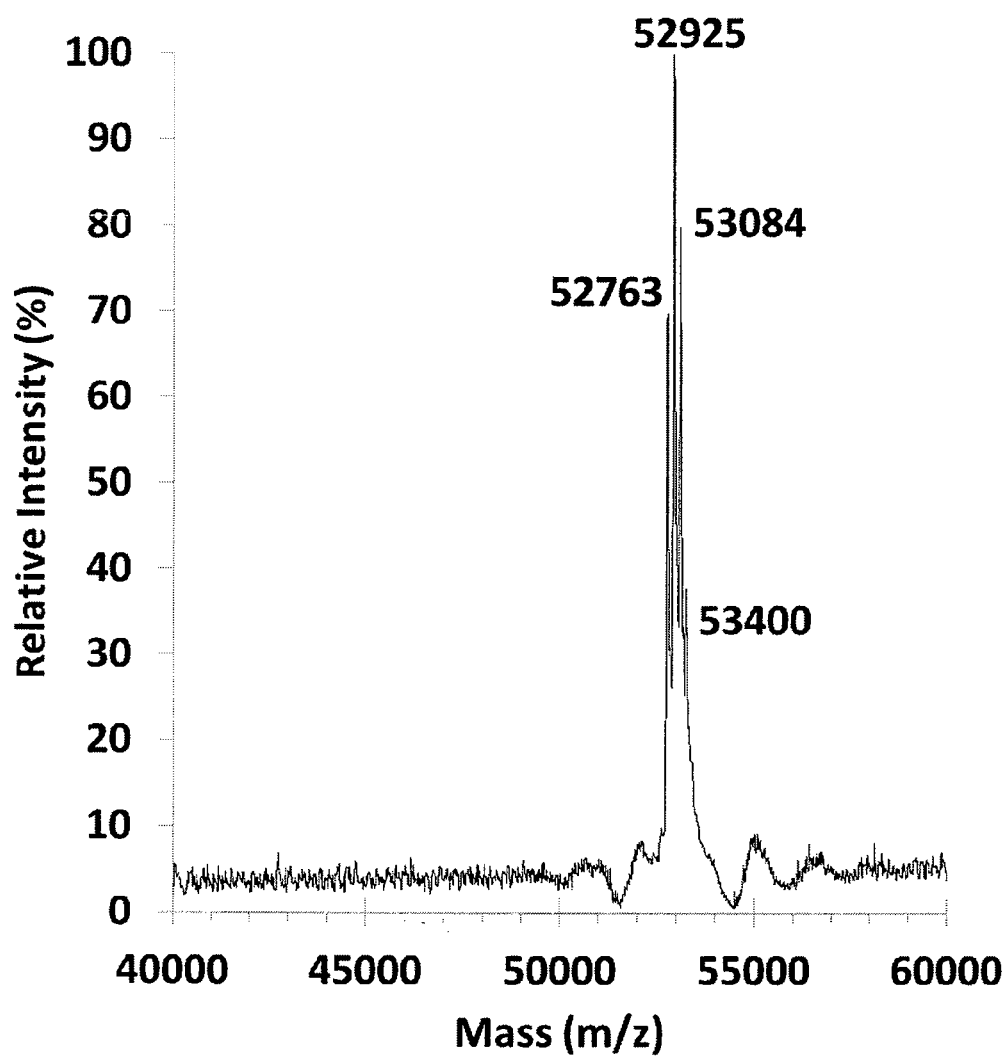
Figure 5:
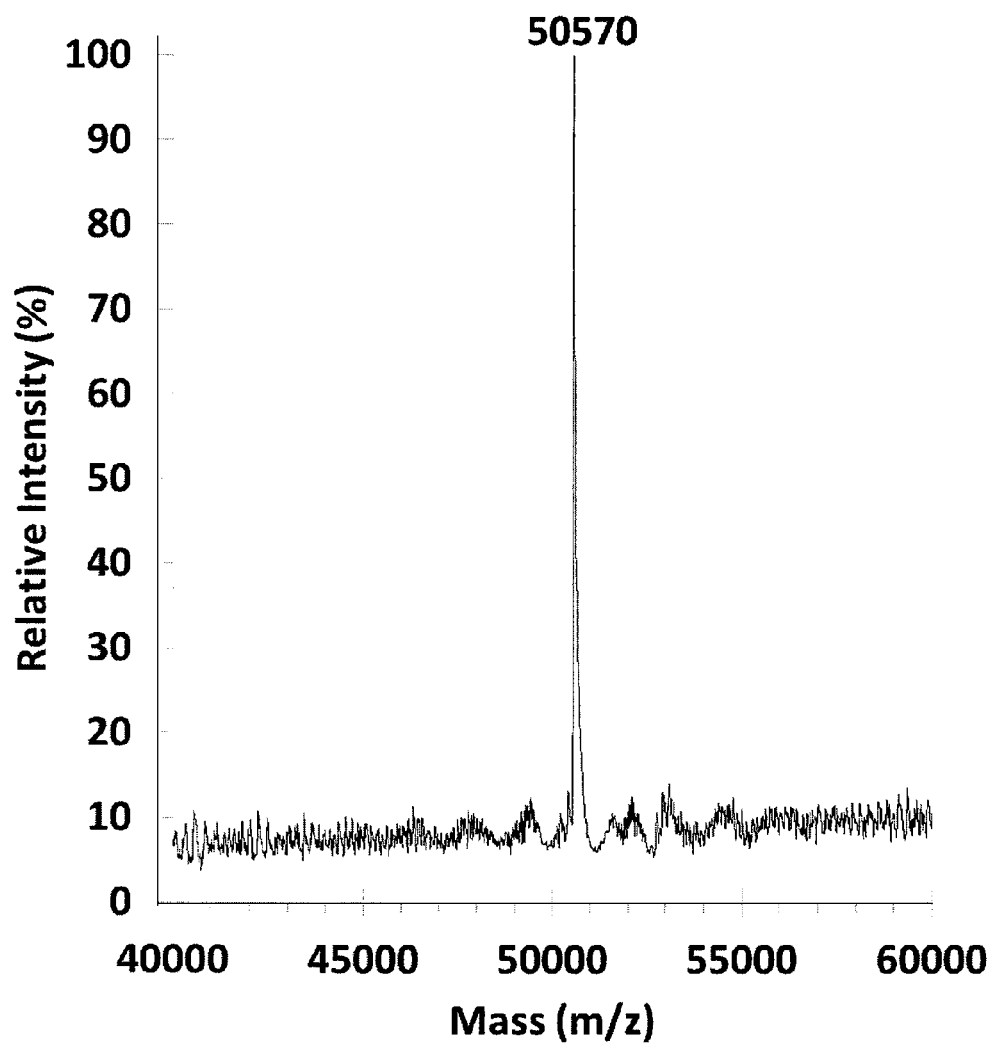
Figure 5:
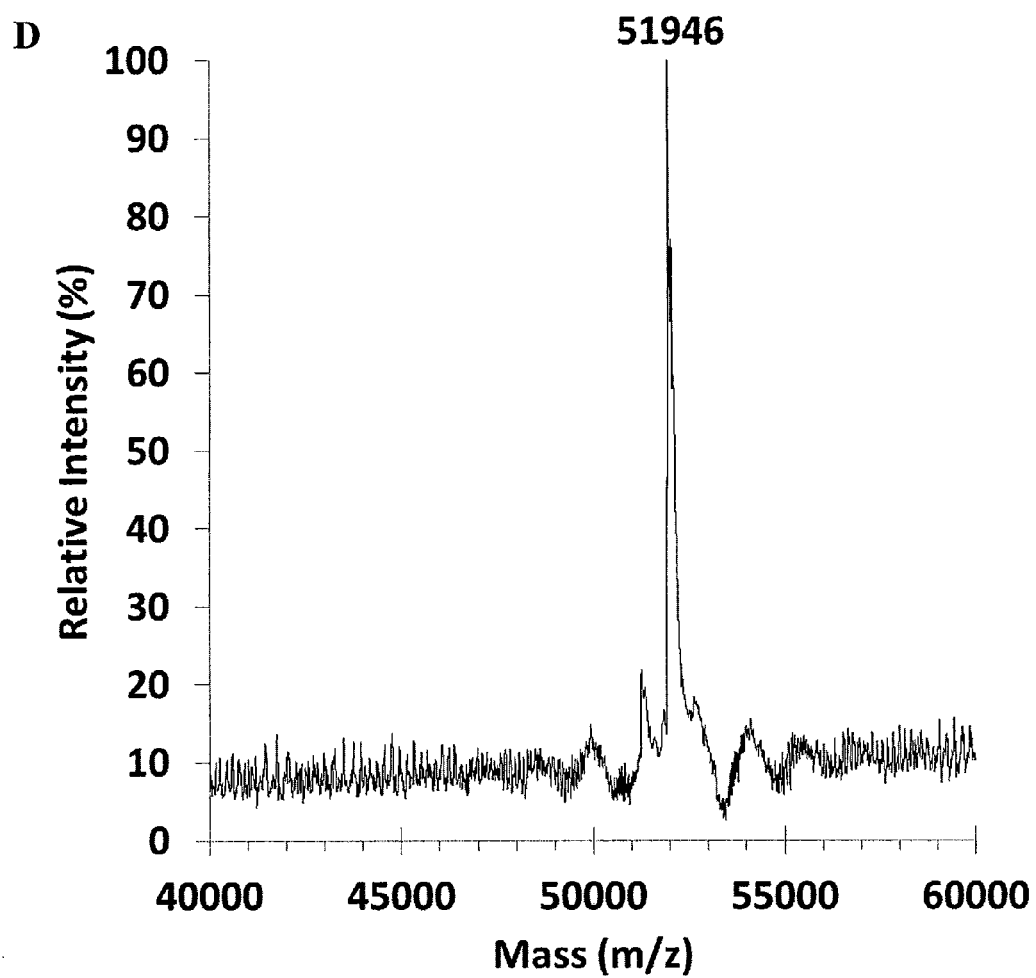

The ability of N322Q mutant to transfer an N-glycan core to the fucosylated GlcNAc-Asn derivative prompted testing to determine whether the mutant was also efficient for glycosylation remodeling of IgG-Fc domain, as demonstrated in FIG. 4. For this purpose, human IgG-Fc fragment was prepared by papain digestion of rituximab, a commercial monoclonal antibody widely used for the treatment of lymphomas, following the previously reported procedure (34). The IgG-Fc fragment was purified by protein A affinity chromatography and was then deglycosylated using Endo-S, an endoglycosidase from S. pyogenes that is specific for IgG deglycosylation (32). The resulting deglycosylated IgG-Fc ((Fucα1,6)GlcNAc-Fc) was a homodimer, in which the innermost disaccharide unit (Fucα1,6GlcNAc) remained at each of the Fc glycosylation sites. SDS-PAGE analysis of the reduced Fc fragments (Fc monomers) before and after deglycosylation indicated that the deglycosylated monomeric Fc (under reduced conditions) appeared as a single band that was about 1.4 kDa smaller than the original IgG-Fc monomer, suggesting the removal of a typical N-glycan from each of the Fc glycosylation sites (FIG. 5A, lane 1, natural complex type-Fc; lane 2, deglycosylated IgG-Fc). The transglycosylation of (Fucα1,6)GlcNAc-Fc with Man₃GlcNAc-oxazoline (5) as the donor substrate and N322Q mutant as the enzyme was monitored by SDS-PAGE (FIG. 5A, lanes 3-8). After 30 min, about half of the Fc acceptor was glycosylated as indicated by a new protein band, which appeared about 1 kDa larger than the precursor (FIG. 5A, lane 4). The reaction reached about 90% of conversion at 2 h (FIG. 5A, lane 6) and went to completion at 5 h (FIG. 5A, lane 8). It should be mentioned that a relatively low molar ratio of donor to acceptor (4:1, oxazoline to GlcNAc of Fc homodimer) could still lead to a 80% conversion at 5 h (data not shown), indicating the high catalytic efficiency of the Endo-D mutant. The glycosylation identity of the Fc fragments before and after remodeling was confirmed by mass spectrometric analysis. MALDI-TOF MS analysis of the Fc N-glycans released by N-glycosidase F revealed that the native N-glycans in the Fc dimer obtained from rituximab were three core-fucosylated biantennary complex type oligosaccharides carrying 0, 1, and 2 terminal galactose residues (termed as G0F, G1F, and G2F glycoforms) (data not shown). ESI-MS of the intact Fc dimer showed four major glycoforms: 52,763 (G0F homodimer), 52,925 (G0F/G1F heterodimer), 53,084 (G1F homodimer), and 53,400 (G2F homodimer) (FIG. 5B). Endo-5-catalyzed deglycosylation converted it into a single species, the ESI-MS data (m/z, 50,573), which matched with the Fc homodimer carrying two Fucα1,6GlcNAc disaccharides (calculated, $M_r$=50,594) (FIG. 5C). The transglycosylation product appeared as a single peak in the ESI-MS (m/z, 51,946), which was in good agreement with the Fc homodimer carrying two core-fucosylated N-pentasaccharides (calculated, $M_r$=51,951) (FIG. 5D). The activity of Endo-D mutants (N322Q and N322A) was also tested on full-size complex type N-glycan oxazolines, including (Gal(β1,4)GlcNAc(β1,2))₂Man₃GlcNAc and (Sia(α-2,6)Galβ(1,4)GlcNAc(β1,2))₂Man₃GlcNAc oxazolines, but no transglycosylation product was detected. These results are consistent with the previously reported substrate specificity of Endo-D in hydrolysis, which shows that Endo-D cannot hydrolyze complex type N-glycan core unless the terminal sialic acid and that the internal galactose and GlcNAc residues are removed by α-sialidase, β-galactosidase, and β-N-acetylglucosaminidase sequentially (7, 35).

The hydrolysis and transglycosylation activity of recombinant Endo-D and its selected mutants was evaluated and the experimental data show that Endo-D can hydrolyze both fucosylated and nonfucosylated N-glycan cores, but the fucosylated N-glycan is a more favorable substrate than the nonfucosylated N-glycan for Endo-D-catalyzed hydrolysis (FIG. 2). The extensively truncated form of Endo-D (a.a. 159-807), which is the proposed catalytic domain (spGH85) used in a previous crystallographic study (16), was much less active than the less truncated Endo-D (a.a. 135-1047) (FIG. 3). Mutation at the Asn-322 and Glu-324 residues abolished the hydrolytic activity of the enzyme, confirming the essential roles of the two residues in Endo-D-catalyzed hydrolysis.

For the transglycosylation, it was found that the Endo-D and related mutants clearly prefer the nonfucosylated GlcNAc to the fucosylated GlcNAc as the acceptor (FIG. 3). Previous studies showed that Endo-D and the recombinant catalytic domain (spGH85) gave a low overall transglycosylation yield, probably because of quick enzymatic hydrolysis of the sugar oxazoline and/or the transglycosylation product (30, 31). In the present invention, several mutants were generated, including Y360F, H371W, N322A, and N322Q, which show significantly enhanced transglycosylation efficiency. In particular, the N322A and N322Q mutants demonstrate remarkable transglycosylation activity with only marginal product hydrolysis activity, leading to an excellent yield of transglycosylation. The two mutants represent the first glycosynthases derived from Endo-D. Kinetic studies have revealed interesting features of the two glycosynthase mutants in terms of their substrate specificity and catalytic efficiency. Both the N322Q and the N322A mutants prefer the nonfucosylated GlcNAc (4) as the acceptor for transglycosylation. For the N322Q mutant, the catalytic efficiency ($k_{cat}/K_m$) on the nonfucosylated GlcNAc acceptor (4) is 10-fold higher than that of the fucosylated GlcNAc acceptor (3) (Table 2). This difference is mainly attributed to the much enhanced affinity of the mutant to the nonfucosylated acceptor ($K_m$ of 0.73 mM for 4 versus $K_m$ of 18.5 mM for 3). The decreased affinity of N322Q for the fucosylated GlcNAc acceptor is most likely due to the steric hindrance caused by the attachment of the α1,6-linked fucose to the GlcNAc acceptor. It has been previously shown that Endo-A, Endo-M, and their corresponding mutants did not recognize core-fucosylated GlcNAc acceptor for transglycosylation (31). Taken together, these results suggest that the ability of Endo-D mutants to glycosylate fucosylated GlcNAc acceptor is most likely due to a more flexible space at the catalytic site in Endo-D to accommodate the fucose than in Endo-A or Endo-M, rather than due to favorable interactions between the fucose residue and the enzyme. The alignment of the available crystal structures of Endo-D (16) and Endo-A (14, 15) was performed and it was found that indeed Endo-D seemed to have a much more opened space for the acceptor recognition site than in Endo-A (data not shown). On the other hand, Endo-D did not recognize the complex type N-glycan oxazoline or Man$_9$GlcNAc-oxazoline for transglycosylation, which is consistent with its substrate specificity in N-glycan hydrolysis.

Comparison of the N322Q and N322A mutants indicates that the N322Q mutant is much more efficient for catalyzing transglycosylation than the N322A mutant. This was reflected by the much enhanced turnover rate ($k_{cat}$) of the N322Q mutant over the N322A mutant for both sugar oxazoline and the acceptor substrates (Tables 1 and 2). In addition, in the case of the nonfucosylated acceptor (4), the N322Q mutant also shows much enhanced affinity for the substrate over the N322A mutant, as estimated by the $K_m$ value (Table 2). These data suggest that although replacement of the Asn-322 with both the Gln and the Ala residue disables its ability to promote oxazolinium ion intermediate formation for product hydrolysis, the Gln residue can better mimic the Asn-322 in promoting the later stage transglycosylation by facilitating the turnover and, in the case of the nonfucosylated GlcNAc acceptor, significantly enhancing the recognition of the acceptor substrate. The N322Q is particularly efficient for glycosylating the deglycosylated Fc domain having a Fucα1,6GlcNAc disaccharide moiety at each of the glycosylation sites. Because Endo-A and Endo-M are unable to recognize the Fucα1,6GlcNAc-Fc domain for transglycosylation (29), the N322Q mutant provides a valuable tool complementing well the existing endoglycosidase-based glycosynthases for remodeling IgG-Fc glycosylation, which is essential for the downstream effector functions of antibodies (37, 38).

In summary, the present invention reveals interesting hydrolysis and transglycosylation properties of Endo-D and its selected mutants. Two novel glycosynthase mutants, N322Q and N322A, demonstrated remarkable transglycosylation efficiency with Man$_3$GlcNAc oxazoline but cannot act on full-length complex type N-glycan oxazoline, showing strict substrate specificity. The N322Q can efficiently glycosylate IgG-Fc domain carrying the Fucα(1,6)GlcNAc moiety.

Materials and Experimental Procedures

The synthesis of Fmoc-Asn(Fucα1,6GlcNAc)-OH, Fmoc-Asn(GlcNAc)-OH, Fmoc-Asn(Man$_3$GlcNAc$_2$Fuc)-OH, and Fmoc-Asn (Man$_3$GlcNAc$_2$)-OH was described in our previous publication (31). Man$_3$GlcNAc-oxazoline was synthesized according to our previously reported procedure (18). Monoclonal antibody rituximab (rituxan, Genentech Inc., South San Francisco, Calif.) was purchased through Premium Health Services Inc. (Columbia, Md.). Papain was purchased from Sigma-Aldrich. The endoglycosidase from *Streptococcus pyogenes* (Endo-S) was expressed and purified according to the reported procedure (32,33).

Cloning, Expression, and Purification of Endo-D in *Escherichia coli*

The cDNA fragment encoding the Endo-D fragment (nucleotides 403-3141; amino acids 135-1047), here called Endo-D, was amplified by PCR from the genomic DNA of *S. pneumoniae* (ATCC number: BA.A.-334D-5). The forward primer was 5'-TATATACATATGGAGTCTAAACCAGCAG-CAGAAGC-3' (SEQ ID NO: 16), and the reverse primer was 5'-GCGCGCCTCGAGTTCTTCTGT-CATCTTTTGGAACGG-3' (SEQ ID NO: 17). NdeI and XhoI site (underlined) were added to the forward and reverse primers, respectively. The cDNA fragment of a further truncated form (nucleotides 475-2471; amino acids 157-807) of Endo-D (called spGH85) was cloned following the previously reported procedure (16). Both of the amplified DNA fragments were cloned into pET28a (Novagen) after digestion with NdeI and XhoI. The constructed plasmids, pET28a-EndoD and pET28a-spGH85, respectively, were transformed into BL21 (DE3). The transformants were cultured in LB media supplemented with 50 µg/ml kanamycin. Cultures were grown at 37° C. until the cells reached an absorbance of 0.5-0.8 at 600 nm. Then 0.5 mM isopropyl β-D-1-thiogalactopyranoside was added to the culture to induce protein overproduction. After further incubation at 25° C. for 8 h, the cells were harvested by centrifugation. The cell pellets was suspended in a sodium phosphate buffer (50 mM, pH 7.0) with lysozyme before sonication. After sonication and centrifugation, the supernatant from the cell lysis was applied onto an Ni$^{2+}$-immobilized HisTrap HP column (GE Healthcare). The column was washed with 50 mM imidazole and then eluted with 200 mM imidazole in a buffer containing 0.5 M NaCl and 0.1 M sodium phosphate (pH 7.4). The eluent was desalted and concentrated by Amicon® Ultra filtration (10 kDa, Millipore, Billerica, Mass.). The homogeneity of the recombinant Endo-D and spGH85 was confirmed by SDS-PAGE with Coomassie Brilliant Blue staining. The protein concentration was quantified using the Bradford assay protocol with bovine serum albumin (BSA) as standard.

Site-Directed Mutagenesis of Endo-D

The selected mutants (N322A, N322Q, E324Q, Y360F, and H371W) were generated using the GENEART site-directed mutagenesis kit (Invitrogen) per the manufacturer's directions. The pET28a-EndoD plasmid encoding the Endo-D gene (nucleotides 403-3141 of SEQ ID NO: 2; amino acids 135-1047, SEQ ID NO: 3) was used as the template, and LA Taq polymerase (Takara) was used for PCR. Mutations were confirmed by DNA sequencing and transformed into BL21 (DE3). Expression and purification of mutants were carried out in the same way as for the wild type enzyme.

Assay for Hydrolytic Activity of Endo-D and Mutants

The hydrolytic activity of each enzyme was determined using the fucosylated and nonfucosylated compounds (1 and 2), respectively. The enzymatic reaction was performed at 30° C. with 0.3 mM substrate in a phosphate buffer (100 mM, pH 7.5, 10 µl) containing an appropriate amount of enzyme (5 ng for Endo-D, 3.6 ng for SpGH85, 100 ng for N322A, 20 ng for N322Q, 10 ng for Y360F, or 5 ng for H371W). Aliquots (1 µl each) were taken at intervals, and the enzymatic reaction was quenched by mixing each aliquot with 50 µl of 0.1% trifluoroacetic acid. The resulting mixture was analyzed by reverse-phase HPLC to quantify the amount of substrate hydrolysis.

High-Performance Liquid Chromatography (HPLC)

Analytical reverse-phase HPLC (RP-HPLC) was performed on a Waters 626 HPLC instrument with a Symmetry300™ $C_{18}$ column (3.5 µm, 4.6×250 mm) at 40° C. The Symmetry300 column was eluted with a linear gradient of 24-35% aq. MeCN containing 0.1% TFA for 30 min at a flow rate of 1 ml/min. The HPLC was monitored by a UV detector at 280 nm. Preparative HPLC was performed with a Waters 600 HPLC instrument on a Waters C18 column (5.0 µm, 10×250 mm). The column was eluted with an appropriate gradient of aq. MeCN containing 0.1% TFA at a flow rate of 4 mL/min.

Electron Spray Ionization Mass Spectrometry (ESI-MS) and Matrix-Assisted Laser Desorption/Ionization Time of Flight Mass Spectrometry (MALDI-TOF MS)

The ESI-MS spectra were measured on a Waters Micromass ZQ-4000 single quadruple mass spectrometer. The MALDI-TOF MS was performed on an Autoflex II MALDI-TOF mass spectrometer (Bruker Daltonics). The instrument was calibrated by using ProteoMass Peptide MALDI-MS calibration kit (MSCAL2, Sigma/Aldrich). The matrix used for glycans was 2,5-dihydroxybenzoic acid (DHB).

Liquid Chromatography-Mass Spectrometry (LC-MS)

The LC-MS analysis of IgG-Fc samples was performed on a LXQ linear ion trap mass spectrometer (Thermo Scientific) equipped with a Hypersil GOLD column (1.9 µm, 50×2.1 mm) (LC conditions: linear gradient of 0-40% MeCN containing 0.1% formic acid within 10 min at a flow rate of 0.25 mL/min; column temperature: 40° C.).

Assay for Transglycosylation Activity of Endo-D and its Mutants

The transglycosylation activity of the enzyme was assayed as follows. A mixture of $Man_3GlcNAc$-oxazoline (5 mM) and Fmoc-Asn(Fucα1,6GlcNAc)-OH (0.5 mM) or Fmoc-Asn (GlcNAc)-OH (0.5 mM) in a sodium phosphate buffer (50 mM, pH 7.5, 5 µl) containing 10% DMSO was incubated with spGH85 (0.19 µg), Endo-D (0.01 µg), or its mutant (0.01 µg), respectively at 30° C. DMSO was added to enhance the solubility of the Fmoc-Asn(GlcNAc)-OH substrate in the aqueous buffer. Aliquots were taken at intervals, and the enzymatic reaction was analyzed by RP-HPLC as described above. The yield of the transglycosylation product was calculated by integration of the peak areas and normalized with the absorbance as follows: transglycosylation yield (%)=(product area/(product area+residual acceptor area))×100%.

Kinetic Studies on Transglycosylation by N322A and N322Q Mutants

To determine the constants ($K_m$ and $k_{cat}$) for $Man_3GlcNAc$-oxazoline, Fmoc-Asn(Fucα1,6GlcNAc)-OH was used as an acceptor at a fixed concentration of 28.4 mM, and the concentration of $Man_3GlcNAc$-oxazoline was varied from 0.63 to 10 mM. The reaction was performed in phosphate buffer (100 mM, pH 7.5, 5 µl) containing 10% DMSO incubated at 30° C. for 10 min with 1 µg of N322A or 0.05 µg of N322Q. Each experimental point was quenched by adding 0.1% trifluoroacetic acid, the mixture was analyzed by RP-HPLC, and the transglycosylation product was quantified as described above. The parameters ($K_m$ and $k_{cat}$) for Fmoc-Asn(Fucα1, 6GlcNAc)-OH were determined with $Man_3GlcNAc$-oxazoline fixed at 2.5 mM, and Fmoc-Asn(Fucα1,6GlcNAc)-OH was varied at five concentrations between 1.77 and 28.4 mM. To determine the parameters for Fmoc-Asn(GlcNAc)-OH, $Man_3GlcNAc$-oxazoline was also fixed at 2.5 mM, and the concentration of Fmoc-Asn(GlcNAc)-OH was varied at five concentrations between 0.89 and 14.2 mM. The $K_m$ and $V_{max}$ values were obtained by fitting the experimental data into the Michaelis-Menten kinetics model using the GraphPad Prism software (GraphPad Software, Inc.).

Papain Digestion of Antibody Rituximab

The antibody was digested with protease papain according the reported method (34), with some modifications. Briefly, a solution of rituximab (20 mg) in a Tris-Cl buffer (20 mM, pH 6.5, 20 ml) containing L-cysteine (2 mM) was incubated with papain (200 µg) at 37° C. The reaction was monitored by SDS-PAGE and LC-MS. When the production of an Fc fragment reached plateau (after 2 h), the reaction mixture was loaded on a column of protein A-agarose resin (5 ml) that was pre-equilibrated with a Tris-Cl buffer (20 mM, pH 8.0). The column was washed with Tris-Cl (20 mM, pH 8.0, 25 ml) and glycine-HCl (20 mM, pH 5.0, 20 ml) successively. The bound Fc fragments were then eluted with glycine-HCl (100 mM, pH 2.5, 20 ml), and the elution fractions were immediately neutralized with Tris-Cl buffer (1.0 M, pH 8.8). The fractions containing the Fc fragments were combined and concentrated by centrifugal filtration (Amicon® Ultra centrifugal filter) to give IgG-Fc (3.5 mg). As determined by LC-MS: calculated for nonglycosylated IgG-Fc dimer, $M_r$=49,896 Da. found (m/z) (deconvoluted data), 52,763 (G0F homodimer), 52,925 (G0F/G1F heterodimer), 53,084 (G1F homodimer), and 53,400 (G2F homodimer).

Deglycosylation of Fc Fragments by Endo-S to Prepare Fucα1,6GlcNAc-Fc

A solution of the purified IgG-Fc (2 mg) in a Tris-Cl buffer (50 mM, pH 7.0, 0.4 ml) was incubated with Endo-S (20 µg) at 30° C. After 30 min, the SDS-PAGE and LC-MS indicated the completion of the deglycosylation. The product was then purified through protein A affinity chromatography following the procedures described above to give the Fucα1,6GlcNAc-Fc (2 mg, quantitative yield). As determined by ESI-MS: calculated for Fucα1,6GlcNAc-Fc, $M_r$=50,594. found (m/z) (deconvoluted data), 50,573.

Transglycosylation to Fucα1,6GlcNAc-Fc by EndoD-N322Q

A solution of Fucα1,6GlcNAc-Fc (506 µg, 10 nmol) and $Man_3GlcNAc$-oxazoline (138 µg, 200 nmol) in a Tris buffer (50 mM, pH 6.8, 50 µl) was incubated with the N322Q mutant (10 µg) at 30° C. Aliquots were taken at intervals and were analyzed by LC-MS. After 5 h, LC-MS indicated the completion reaction of Fucα1,6GlcNAc-Fc to give a new species corresponding to the transglycosylation product. The reaction mixture was injected into LC-MS, and the molecular weight of transglycosylation product was determined by ESI-MS: calculated for $Man_3GlcNAc(\alpha1,6Fuc)GlcNAc$-Fc homodimer, $M_r$=51,951. found (m/z) (deconvoluted data), 51,946.

REFERENCES

The contents of all references cited herein are hereby incorporated by reference herein for all purposes.

1. Robbins, P. W., et al. (1984) Primary structure of the *Streptomyces* enzyme endo-β-N-acetylglucosaminidase H., *J. Biol. Chem.* 259, 7577-7583.
2. Tarentino, A. L., et al., (1992) Multiple endoglycosidase (Endo) F activities expressed by *Flavobacterium meningosepticum*. Endo F1: molecular cloning, primary sequence, and structural relationship to Endo H., *J. Biol. Chem.* 267, 3868-3872.
3. Tarentino, A. L., et al., (1993) Multiple endoglycosidase F activities expressed by *Flavobacterium meningosepticum* endoglycosidases F2 and F3: molecular cloning, primary sequence, and enzyme expression. *J. Biol. Chem.* 268, 9702-9708.
4. Kadowaki, S., et al., 4 (1991) Microbial endo-β-N-acetylglucosaminidases acting on complex-type sugar chains of glycoproteins. *J. Biochem.* 110, 17-21.
5. Yamamoto K., et al., (1994) Novel specificities of *Mucor hiemalis* endo-β-N-acetylglucosaminidase acting complex asparagine-linked oligosaccharides. *Biosci. Biotechnol. Biochem.* 58, 72-77.

6. Takegawa K., et al., (1997) Cloning, sequencing, and expression of *Arthrobacter* protophormiae endo-β-N-acetylglucosaminidase in *Escherichia coli*. *Arch. Biochem. Biophys.* 338, 22-28.

7. Muramatsu H., et al., (2001) Molecular cloning and expression of endo-β-N-acetylglucosaminidase D, which acts on the core structure of complex type asparagine-linked oligosaccharides. *J. Biochem.* 129, 923-928.

8. Kato T., et al., (2002) Identification of an endo-β-N-acetylglucosaminidase gene in *Caenorhabditis elegans* and its expression in *Escherichia coli*. *Glycobiology* 12, 581-587.

9. Wang L. X., (2008) Chemoenzymatic synthesis of glycopeptides and glycoproteins through endoglycosidase-catalyzed transglycosylation. *Carbohydr. Res.* 343, 1509-1522.

10. Wang L. X., (2011) The amazing transglycosylation activity of endo-β-N-acetylglucosaminidases. *Trends Glycosci. Glycotechnol.* 23, 33-52.

11. Rao V., et al., (1999) Mutations of endo-β-N-acetylglucosaminidase H active site residues Asp-130 and Glu-132: activities and conformations. *Protein Sci.* 8, 2338-2346.

12. Van Roey P., et al., (1994) Crystal structure of endo-β-N-acetylglucosaminidase F1, an α/β-barrel enzyme adapted for a complex substrate. *Biochemistry* 33, 13989-13996.

13. Waddling C. A., et al., (2000) Structural basis for the substrate specificity of endo-β-N-acetylglucosaminidase F3. *Biochemistry* 39, 7878-7885.

14. Yin J., et al., (2009) Structural basis and catalytic mechanism for the dual functional endo-β-N-acetylglucosaminidase A. *PLoS One* 4, e4658.

15. Ling Z., et al., (2009) The x-ray crystal structure of an *Arthrobacter* protophormiae endo-β-N-acetylglucosaminidase reveals a ((β/α)8 catalytic domain, two ancillary domains, and active site residues key for transglycosylation activity. *J. Mol. Biol.* 389, 1-9.

16. Abbott D. W., et al., (2009) *Streptococcus pneumoniae* endohexosaminidase D, structural and mechanistic insight into substrate-assisted catalysis in family 85 glycoside hydrolases. *J. Biol. Chem.* 284, 11676-11689.

17. Fujita M., et al., (2001) A novel disaccharide substrate having 1,2-oxazoline moiety for detection of transglycosylating activity of endoglycosidases. *Biochim. Biophys. Acta* 1528, 9-14.

18. Li B., et al., (2005) Highly efficient endoglycosidase-catalyzed synthesis of glycopeptides using oligosaccharide oxazolines as donor substrates. *J. Am. Chem. Soc.* 127, 9692-9693

19. Li B., et al., (2006) A highly efficient chemoenzymatic approach toward glycoprotein synthesis. *Org. Lett.* 8, 3081-3084.

20. Rising T. W., et al., (2006) Endohexosaminidase M: exploring and exploiting enzyme substrate specificity. *ChemBioChem.* 7, 1177-1180.

21. Ochiai H., et al., (2008) Expeditious chemoenzymatic synthesis of homogeneous N-glycoproteins carrying defined oligosaccharide ligands. *J. Am. Chem. Soc.* 130, 13790-13803.

22. Wei Y., et al., (2008) Glycoengineering of human IgG1-Fc through combined yeast expression and in vitro chemoenzymatic glycosylation. *Biochemistry* 47, 10294-10304.

23. Umekawa M., et al., (2008) Mutants of *Mucor hiemalis* endo-β-N-acetylglucosaminidase show enhanced transglycosylation and glycosynthase-like activities. *J. Biol. Chem.* 283, 4469-4479.

24. Huang W., et al., (2009) Glycosynthases enable a highly efficient chemoenzymatic synthesis of N-glycoproteins carrying intact natural N-glycans. *J. Am. Chem. Soc.* 131, 2214-2223.

25. Umekawa M., et al., (2010) Efficient glycosynthase mutant derived from *Mucor hiemalis* endo-β-N-acetylglucosaminidase capable of transferring oligosaccharide from both sugar oxazoline and natural N-glycan. *J. Biol. Chem.* 285, 511-521.

26. Umekawa M., et al., (2010) Efficient transfer of sialo-oligosaccharide onto proteins by combined use of a glycosynthase-like mutant of *Mucor hiemalis* endoglycosidase and synthetic sialo-complex-type sugar oxazoline. *Biochim. Biophys. Acta* 1800, 1203-1209.

27. Schwarz F., et al., (2010) A combined method for producing homogeneous glycoproteins with eukaryotic N-glycosylation. *Nat. Chem. Biol.* 6, 264-266.

28. Amin M. N., et al., (2011) Convergent synthesis of homogeneous Glc1Man9GlcNAc2 protein and derivatives as ligands of molecular chaperones in protein quality control. *J. Am. Chem. Soc.* 133, 14404-14417.

29. Zou G., et al., (2011) Chemoenzymatic synthesis and Fcγ receptor binding of homogeneous glycoforms of antibody Fc domain: presence of a bisecting sugar moiety enhances the affinity of Fc to FcγIIIa receptor. *J. Am. Chem. Soc.* 133, 18975-18991.

30. Parsons T. B., et al., (2010) *Streptococcus pneumoniae* endohexosaminidase D: feasibility of using N-glycan oxazoline donors for synthetic glycosylation of a GlcNAc-asparagine acceptor. *Org. Biomol. Chem.* 8, 1861-1869.

31. Huang W., et al., (2011) Unusual transglycosylation activity of *Flavobacterium meningosepticum* endoglycosidases enables convergent chemoenzymatic synthesis of core-fucosylated complex N-glycopeptides. *ChemBioChem.* 12, 932-941.

32. Collin M., et al., (2001) EndoS, a novel secreted protein from *Streptococcus pyogenes* with endoglycosidase activity on human IgG. *EMBO J.* 20, 3046-3055.

33. Collin M., et al., (2001) Effect of SpeB and EndoS from *Streptococcus pyogenes* on human immunoglobulins. *Infect. Immun.* 69, 7187-7189.

34. Raju T. S., et al., (2006) Glycosylation in the Fc domain of IgG increases resistance to proteolytic cleavage by papain. *Biochem. Biophys. Res. Commun.* 341, 797-803.

35. Yamamoto S., et al., (2005) Mutational studies on endo-β-N-acetylglucosaminidase D which hydrolyzes core portion of asparagine-linked complex type oligosaccharides. *Glycoconj. J.* 22, 35-42.

36. Fujita K., et al., (2001) Tryptophan-216 is essential for the transglycosylation activity of endo-β-N-acetylglucosaminidase A. *Biochem. Biophys. Res. Commun.* 283, 680-686.

37. Jefferis R. (2009) Glycosylation as a strategy to improve antibody-based therapeutics. *Nat. Rev. Drug Discov.* 8, 226-234.

38. Nimmerjahn F., et al., (2008) Anti-inflammatory actions of intravenous immunoglobulin. *Annu. Rev. Immunol.* 26, 513-533.

That which is claimed is:

1. A method of preparing a fucosylated or nonfucosylated glycoprotein having a predetermined oligosaccharide moiety, the method comprising:
   providing a fucosylated or nonfucosylated GlcNAc acceptor protein comprising an asparagine-linked N-acetylglucosamine (GlcNAc) residue, wherein the fucosylated acceptor protein is an alpha-1-6-fucosyl-GlcNAc-protein and the nonfucosylated acceptor protein is an alpha-1-6-GlcNAc-protein; and
   enzymatically reacting the fucosylated or nonfucosylated GlcNAc acceptor protein with an activated oligosaccharide donor in the presence of an Endoglycosidase-D full length or truncated mutant selected from the group consisting of SEQ ID NO: 4, SEQ ID NO: 5, SEQ ID NO: 6, SEQ ID NO: 7, SEQ ID NO: 8, and SEQ ID NO: 9, wherein the activated oligosaccharide donor comprises an oxazoline covalently linked to an oligosaccharide moiety, wherein the oligosaccharide moiety comprises a mannose type N-glycan having a predetermined number of mannose residues, wherein the enzymatically reacting covalently links the oligosaccharide moiety to the fucosylated or nonfucosylated GlcNAc acceptor protein, thereby providing the fucosylated or nonfucosylated glycoprotein having the predetermined oligosaccharide moiety.

2. The method of claim 1, wherein the fucosylated or nonfucosylated GlcNAc acceptor protein is an antibody or fragment thereof.

3. The method of claim 1, wherein the activated oligosaccharide donor is a oligosaccharide oxazoline.

4. The method of claim 3, wherein the oligosaccharide oxazoline comprises di-, tri-, tetra-, penta-, hexyl-, hepta-, or octyl-mannoses.

5. The method of claim 4, wherein the activated oligosaccharide oxazoline further comprises an additional biologically active agent or a tag.

6. The method of claim 5, wherein the additional biologically active agent or tag is a drug, toxin, fluorescent probe, biotin, a PEG, lipid, or polypeptide.

7. The method of claim 2, wherein the antibody is a monoclonal antibody selected from the group consisting of cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, efalizumab, bevacizumab, panitumumab, pertuzumab, natalizumab, etanercept, volociximab, Anti-CD80 mAb, Anti-CD23 mAb, eraptuzumab, matuzumab, zanolimumab, adecatumumab, oregovomab, nimotuzumab, denosumab, fontolizumab, daclizumab, golimumab, ocrelizumab, HuMax-CD20, belimumab, epratuzumab, visilizumab, tocilizumab, ocrerlizumab, certolizumab pegol, eculizumab, pexelizumab, abciximab, ranibizimumab, and mepolizumab.

8. The method of claim 1, wherein the step of providing a fucosylated or nonfucosylated GLcNAc acceptor protein comprises
   (a) providing a fucosylated or nonfucosylated glycoprotein substrate comprising at least two GlcNAc residues having a covalent bond between the at least two GlcNAc residues, wherein one of the at least two GlcNAc residues is covalently bonded to an amino acid residue of the fucosylated or nonfucosylated glycoprotein; and
   (b) enzymatically treating the fucosylated or nonfucosylated glycoprotein substrate with an endoglycosidase enzyme to hydrolyze the covalent bond between the at least two GlcNAc residues, thereby forming a deglycosylated protein having a single GlcNAc-moiety, wherein the endoglycosidase enzyme is selected from the group consisting of Endoglycosidase-H, Endoglycosidase-S, Endoglycosidase-F3 and Endoglycosidase-A.

9. The method of claim 2, wherein the antibody or fragment thereof further comprises an additional moiety selected from a group consisting of a therapeutic agent for treating cancer, a therapeutic agent for HIV, a toxin, an antigen, a chemokine and a cytokine.

10. A method of synthesizing a modified antibody or fragment thereof, the method comprising;
    providing an antibody or fragment thereof comprising a fucosylated or nonfucosylated N-acetylglucosamine (GlcNAc) moiety; wherein the fucosylated or nonfucosylated N-acetylglucosamine (GlcNAc) moiety is positioned on a Fc region of the antibody or fragment thereof;
    enzymatically transferring an oligosaccharide having a predetermined number of saccharides to the fucosylated or nonfucosylated N-acetylglucosamine (GlcNAc) moiety under the catalysis of an Endoglycosidase-D full length or truncated mutant selected from the group consisting of SEQ ID NO: 4, SEQ ID NO: 5, SEQ ID NO: 6, SEQ ID NO: 7, SEQ ID NO: 8 and SEQ ID NO: 9, to form the modified antibody or fragment thereof with the predetermined number of saccharides.

11. The method of claim 10, wherein the modified antibody or fragment thereof further comprises an additional moiety including, a therapeutic agent for treating cancer, a therapeutic agent for HIV, a toxin, an antigen, a therapeutic polypeptide, a chemokine and/or a cytokine attached to the oligosaccharide.

* * * * *

SEQUENCE LISTING

<160> NUMBER OF SEQ ID NOS: 17

<210> SEQ ID NO 1
<211> LENGTH: 1646
<212> TYPE: PRT
<213> ORGANISM: Streptococcus pneumoniae

<400> SEQUENCE: 1

```
Met Lys Asn Pro Phe Phe Glu Arg Arg Cys Arg Tyr Ser Ile Arg Lys
1               5                   10                  15

Leu Ser Val Gly Ala Cys Ser Leu Met Ile Gly Ala Val Leu Phe Val
            20                  25                  30

Gly Pro Ala Leu Ala Glu Glu Thr Ala Val Pro Glu Asn Ser Gly Ala
        35                  40                  45

Asn Thr Glu Leu Val Ser Gly Glu Ser Glu His Ser Thr Asn Glu Ala
    50                  55                  60

Asp Lys Gln Asn Glu Gly Glu His Thr Arg Glu Asn Lys Leu Glu Lys
65                  70                  75                  80

Ala Glu Gly Val Ala Thr Ala Ser Glu Thr Ala Glu Ala Ala Ser Ala
                85                  90                  95

Ala Lys Pro Glu Glu Lys Ala Gly Glu Val Ala Glu Thr Pro Ser
            100                 105                 110

Ala Glu Ala Lys Pro Lys Ser Asp Lys Glu Thr Glu Lys Pro Glu
        115                 120                 125

Ala Thr Asn Gln Gly Asp Glu Ser Lys Pro Ala Ala Glu Ala Asn Lys
    130                 135                 140

Thr Glu Lys Glu Val Gln Pro Asp Val Pro Lys Asn Thr Glu Lys Thr
145                 150                 155                 160

Leu Lys Pro Lys Glu Ile Lys Phe Asn Ser Trp Glu Gly Leu Leu Lys
                165                 170                 175

Trp Glu Pro Gly Ala Arg Glu Asp Asp Ala Ile Asn Arg Gly Ser Val
            180                 185                 190

Val Leu Ala Ser Arg Arg Thr Gly His Leu Val Asn Glu Lys Ala Ser
        195                 200                 205

Lys Glu Ala Lys Val Gln Ala Leu Ser Asn Thr Asn Ser Lys Ala Lys
    210                 215                 220

Asp His Ala Ser Val Gly Gly Glu Glu Phe Lys Ala Tyr Ala Phe Asp
225                 230                 235                 240

Tyr Trp Gln Tyr Leu Asp Ser Met Val Phe Trp Glu Gly Leu Val Pro
                245                 250                 255

Thr Pro Asp Val Ile Asp Ala Gly His Arg Asn Gly Val Pro Val Tyr
            260                 265                 270

Gly Thr Leu Phe Phe Asn Trp Ser Asn Ser Ile Ala Asp Gln Glu Arg
        275                 280                 285

Phe Ala Glu Ala Leu Lys Gln Asp Ala Asp Gly Ser Phe Pro Ile Ala
    290                 295                 300

Arg Lys Leu Val Asp Met Ala Lys Tyr Tyr Gly Tyr Asp Gly Tyr Phe
305                 310                 315                 320

Ile Asn Gln Glu Thr Thr Gly Asp Leu Val Lys Pro Leu Gly Glu Lys
                325                 330                 335

Met Arg Gln Phe Met Leu Tyr Ser Lys Glu Tyr Ala Ala Lys Val Asn
            340                 345                 350

His Pro Ile Lys Tyr Ser Trp Tyr Asp Ala Met Thr Tyr Asn Tyr Gly
        355                 360                 365
```

```
Arg Tyr His Gln Asp Gly Leu Gly Glu Tyr Asn Tyr Gln Phe Met Gln
    370             375                 380

Pro Glu Gly Asp Lys Val Pro Ala Asp Asn Phe Phe Ala Asn Phe Asn
385             390                 395                 400

Trp Asp Lys Ala Lys Asn Asp Tyr Thr Ile Ala Thr Ala Asn Trp Ile
                405                 410                 415

Gly Arg Asn Pro Tyr Asp Val Phe Ala Gly Leu Glu Leu Gln Gln Gly
                420                 425                 430

Gly Ser Tyr Lys Thr Lys Val Lys Trp Asn Asp Ile Leu Asp Glu Asn
        435                 440                 445

Gly Lys Leu Arg Leu Ser Leu Gly Leu Phe Ala Pro Asp Thr Ile Thr
    450                 455                 460

Ser Leu Gly Lys Thr Gly Glu Asp Tyr His Lys Asn Glu Asp Ile Phe
465             470                 475                 480

Phe Thr Gly Tyr Gln Gly Asp Pro Thr Gly Gln Lys Pro Gly Asp Lys
                485                 490                 495

Asp Trp Tyr Gly Ile Ala Asn Leu Val Ala Asp Arg Thr Pro Ala Val
                500                 505                 510

Gly Asn Thr Phe Thr Thr Ser Phe Asn Thr Gly His Gly Lys Lys Trp
                515                 520                 525

Phe Val Asp Gly Lys Val Ser Lys Asp Ser Glu Trp Asn Tyr Arg Ser
530             535                 540

Val Ser Gly Val Leu Pro Thr Trp Arg Trp Gln Thr Ser Thr Gly
545                 550                 555                 560

Glu Lys Leu Arg Ala Glu Tyr Asp Phe Thr Asp Ala Tyr Asn Gly Gly
                565                 570                 575

Asn Ser Leu Lys Phe Ser Gly Asp Val Ala Gly Lys Thr Asp Gln Asp
        580                 585                 590

Val Arg Leu Tyr Ser Thr Lys Leu Glu Val Thr Glu Lys Thr Lys Leu
    595                 600                 605

Arg Val Ala His Lys Gly Gly Lys Gly Ser Lys Val Tyr Met Ala Phe
    610                 615                 620

Ser Thr Thr Pro Asp Tyr Lys Phe Asp Asp Ala Asp Ala Trp Lys Glu
625             630                 635                 640

Leu Thr Leu Ser Asp Asn Trp Thr Asn Glu Glu Phe Asp Leu Ser Ser
                645                 650                 655

Leu Ala Gly Lys Thr Ile Tyr Ala Val Lys Leu Phe Phe Glu His Glu
                660                 665                 670

Gly Ala Val Lys Asp Tyr Gln Phe Asn Leu Gly Gln Leu Thr Ile Ser
                675                 680                 685

Asp Asn His Gln Glu Pro Gln Ser Pro Thr Ser Phe Ser Val Val Lys
    690                 695                 700

Gln Ser Leu Lys Asn Ala Gln Glu Ala Glu Ala Val Val Gln Phe Lys
705             710                 715                 720

Gly Asn Lys Asp Ala Asp Phe Tyr Glu Val Tyr Glu Lys Asp Gly Asp
                725                 730                 735

Ser Trp Lys Leu Leu Thr Gly Ser Ser Ser Thr Thr Ile Tyr Leu Pro
                740                 745                 750

Lys Val Ser Arg Ser Ala Ser Ala Gln Gly Thr Thr Gln Glu Leu Lys
                755                 760                 765

Val Val Ala Val Gly Lys Asn Gly Val Arg Ser Glu Ala Ala Thr Thr
    770                 775                 780

Thr Phe Asp Trp Gly Met Thr Val Lys Asp Thr Ser Leu Pro Lys Pro
```

-continued

```
            785                 790                 795                 800
    Leu Ala Glu Asn Ile Val Pro Gly Ala Thr Val Ile Asp Ser Thr Phe
                        805                 810                 815
    Pro Lys Thr Glu Gly Glu Gly Ile Glu Gly Met Leu Asn Gly Thr
                820                 825                 830
    Ile Thr Ser Leu Ser Asp Lys Trp Ser Ala Gln Leu Ser Gly Ser
                    835                 840                 845
    Val Asp Ile Arg Leu Thr Lys Pro Arg Thr Val Arg Trp Val Met
        850                 855                 860
    Asp His Ala Gly Ala Gly Glu Ser Val Asn Asp Gly Leu Met Asn
    865                 870                 875                 880
    Thr Lys Asp Phe Asp Leu Tyr Tyr Lys Asp Ala Asp Gly Glu Trp Lys
                        885                 890                 895
    Leu Ala Lys Glu Val Arg Gly Asn Lys Ala His Val Thr Asp Ile Thr
                    900                 905                 910
    Leu Asp Lys Pro Ile Thr Ala Gln Asp Trp Arg Leu Asn Val Val Thr
                915                 920                 925
    Ser Asp Asn Gly Thr Pro Trp Lys Ala Ile Arg Ile Tyr Asn Trp Lys
        930                 935                 940
    Met Tyr Glu Lys Leu Asp Thr Glu Ser Val Asn Ile Pro Met Ala Lys
    945                 950                 955                 960
    Ala Ala Ala Arg Ser Leu Gly Asn Asn Lys Val Gln Val Gly Phe Ala
                        965                 970                 975
    Asp Val Gln Ala Gly Ala Thr Ile Thr Val Tyr Asp Asn Pro Asn Ser
                    980                 985                 990
    Gln Thr Pro Leu Ala Thr Leu Lys Ser Glu Val Gly Gly Asp Leu Ala
                995                 1000                1005
    Ser Ala Pro Leu Asp Leu Thr Asn Gln Ser Gly Leu Leu Tyr Tyr
        1010                1015                1020
    Arg Thr Gln Leu Pro Gly Lys Glu Ile Ser Asn Val Leu Ala Val
        1025                1030                1035
    Ser Val Pro Lys Asp Asp Arg Ile Lys Ser Val Ser Leu Glu
        1040                1045                1050
    Thr Gly Pro Lys Lys Thr Ser Tyr Ala Glu Gly Glu Asp Leu Asp
        1055                1060                1065
    Leu Arg Gly Gly Val Leu Arg Val Gln Tyr Glu Gly Gly Thr Glu
        1070                1075                1080
    Asp Glu Leu Ile Arg Leu Thr His Ala Gly Val Ser Val Ser Gly
        1085                1090                1095
    Phe Asp Thr His His Lys Gly Glu Gln Asn Leu Thr Leu Gln Tyr
        1100                1105                1110
    Leu Gly Gln Pro Val Asn Ala Asn Leu Ser Val Thr Val Thr Gly
        1115                1120                1125
    Gln Asp Glu Ala Ser Pro Lys Thr Ile Leu Gly Ile Glu Val Ser
        1130                1135                1140
    Gln Lys Pro Lys Lys Asp Tyr Leu Val Gly Asp Ser Leu Asp Leu
        1145                1150                1155
    Ser Glu Gly Arg Phe Ala Val Ala Tyr Ser Asn Asp Thr Met Glu
        1160                1165                1170
    Glu His Ser Phe Thr Asp Glu Gly Val Glu Ile Ser Gly Tyr Asp
        1175                1180                1185
    Ala Gln Lys Thr Gly Arg Gln Thr Leu Thr Leu Arg Tyr Gln Gly
        1190                1195                1200
```

```
His Glu Val Asn Phe Asp Val Leu Val Ser Pro Lys Ala Ala Leu
1205                1210                1215

Asn Asp Glu Tyr Leu Lys Gln Lys Leu Ala Glu Val Glu Ala Ala
1220                1225                1230

Lys Asn Lys Val Val Tyr Asn Phe Ala Ser Pro Glu Val Lys Glu
1235                1240                1245

Ala Phe Leu Lys Ala Ile Glu Ala Ala Glu Gln Val Leu Lys Asp
1250                1255                1260

His Glu Ile Ser Thr Gln Asp Gln Val Asn Asp Arg Leu Asn Lys
1265                1270                1275

Leu Thr Glu Ala His Lys Ala Leu Asn Gly Gln Glu Lys Phe Lys
1280                1285                1290

Glu Glu Lys Thr Glu Leu Asp Arg Leu Thr Gly Glu Val Gln Glu
1295                1300                1305

Leu Leu Asp Ala Lys Pro Asn His Pro Ser Gly Ser Ala Leu Ala
1310                1315                1320

Pro Leu Leu Glu Lys Asn Lys Val Leu Val Glu Lys Val Asp Leu
1325                1330                1335

Ser Pro Glu Glu Leu Ala Thr Ala Lys Gln Ser Leu Lys Asp Leu
1340                1345                1350

Val Ala Leu Leu Lys Glu Asp Lys Pro Ala Val Phe Ser Asp Ser
1355                1360                1365

Lys Thr Gly Val Glu Val His Phe Ser Asn Lys Glu Lys Thr Val
1370                1375                1380

Ile Lys Gly Leu Lys Val Glu Arg Val Gln Ala Ser Ala Glu Glu
1385                1390                1395

Lys Lys Tyr Phe Ala Gly Glu Asp Ala His Val Phe Glu Ile Glu
1400                1405                1410

Gly Leu Asp Glu Lys Gly Gln Asp Val Asp Leu Ser Tyr Ala Ser
1415                1420                1425

Ile Val Lys Ile Pro Ile Glu Lys Asp Lys Lys Val Lys Lys Val
1430                1435                1440

Phe Phe Leu Pro Glu Gly Lys Glu Ala Val Glu Leu Ala Phe Glu
1445                1450                1455

Gln Thr Asp Ser His Val Ile Phe Thr Ala Pro His Phe Thr His
1460                1465                1470

Tyr Ala Phe Val Tyr Glu Ser Ala Glu Lys Pro Gln Pro Ala Lys
1475                1480                1485

Pro Ala Pro Gln Asn Lys Val Leu Pro Lys Pro Thr Tyr Gln Pro
1490                1495                1500

Ala Ser Asp Gln Gln Lys Ala Pro Lys Leu Glu Val Gln Glu Glu
1505                1510                1515

Lys Val Ala Phe His Arg Gln Glu His Glu Asn Ala Glu Met Leu
1520                1525                1530

Val Gly Glu Gln Arg Val Ile Gln Gly Arg Asp Gly Leu Leu
1535                1540                1545

Arg His Val Phe Glu Val Asp Glu Asn Gly Gln Arg Arg Leu Arg
1550                1555                1560

Ser Thr Glu Val Ile Gln Glu Ala Ile Pro Glu Ile Val Glu Ile
1565                1570                1575

Gly Thr Lys Val Lys Thr Val Pro Ala Val Val Ala Thr Gln Glu
1580                1585                1590
```

| | | | | | | | | | | |
|---|---|---|---|---|---|---|---|---|---|---|
|Lys|Pro|Ala|Gln|Asn|Thr|Ala|Val|Lys|Ser|Glu|Glu|Ala|Ser|Lys|
|1595| | | | |1600| | | | |1605| | | | |

| | | | | | | | | | | |
|---|---|---|---|---|---|---|---|---|---|---|
|Gln|Leu|Pro|Asn|Thr|Gly|Thr|Ala|Asp|Ala|Asn|Glu|Ala|Leu|Ile|
|1610| | | | |1615| | | | |1620| | | | |

| | | | | | | | | | | |
|---|---|---|---|---|---|---|---|---|---|---|
|Ala|Gly|Leu|Ala|Ser|Leu|Gly|Leu|Ala|Ser|Leu|Ala|Leu|Thr|Leu|
|1625| | | | |1630| | | | |1635| | | | |

| | | | | | |
|---|---|---|---|---|---|
|Arg|Arg|Lys|Arg|Glu|Asp|Lys|Asp|
|1640| | | | |1645| | |

<210> SEQ ID NO 2
<211> LENGTH: 5021
<212> TYPE: DNA
<213> ORGANISM: Streptococcus pneumoniae

<400> SEQUENCE: 2

| | |
|---|---|
|atataaagcg ctttcttgaa acaacaaaa tcaatctttt aggaggagaa aatgaagaat|60|
|ccatttttg aaagacgttg tcgttacagt attcgtaagt tatcagtagg agcctgctcg|120|
|ctgatgattg gtgctgtttt atttgttggt ccagccttgg ctgaagaaac tgcagttcct|180|
|gaaaatagcg gagctaatac agagcttgtt tcaggagaga gtgagcattc gaccaatgaa|240|
|gctgataagc agaatgaagg ggaacatact agagaaaaca gctagaaaaa ggcagaagga|300|
|gtagcgacag catctgaaac tgcagaagca gctagcgcag ctaaaccaga ggaaaaagca|360|
|ggtgaggtgg ttgcagaaac accatctgca gaagcaaaac ctaagtctga caggaaaaca|420|
|gaagcaaagc ccgaagcaac taaccaaggg gatgagtcta aaccagcagc agaagctaat|480|
|aagactgaaa aagaagtcca gccagatgtc cctaaaaata cagaaaaaac attaaaacca|540|
|aaggaaatca aatttaattc ttgggaagaa ttgttaaaat gggaaccagg tgctcgtgaa|600|
|gatgatgcta ttaaccgcgg atctgttgtc ctcgcttcac gtcggacagg tcatttagtc|660|
|aatgaaaaag ctagcaagga agcaaaagtt caagccttat caaacaccaa ttctaaagca|720|
|aaagaccatg cttctgttgg tggagaagag ttcaaggcct atgcttttga ctattggcaa|780|
|tatctagatt caatggtctt ctgggaaggt ctcgtaccaa ctcctgacgt tattgatgca|840|
|ggtcaccgta acggggttcc tgtatacggt acactcttct tcaactggtc taatagtatt|900|
|gcagatcaag aaagatttgc tgaagctttg aagcaagacg cagatggtag cttcccaatt|960|
|gcccgtaaat ggtagacat ggccaagtat tatggctatg atggctattt catcaaccaa|1020|
|gaaacaactg gagatttggt taaacctctt ggagaaaaga tgcgccagtt tatgctctat|1080|
|agcaaggaat atgctgctaa ggtaaaccat ccaatcaagt attcttggta tgatgccatg|1140|
|acctataact atggacgtta ccatcaagat ggtttgggag aatacaacta ccaattcatg|1200|
|caaccagaag gagataaggt tccggcagat aacttctttg ctaactttaa ctgggataag|1260|
|gctaaaaatg attacactat tgcaactgcc aactggattg gtcgtaatcc ctatgatgta|1320|
|tttgcaggtt tggaattgca acagggtggt tcctacaaga caaaggttaa gtggaatgac|1380|
|attttagacg aaaatgggaa attgcgcctt tctcttggtt tatttgcccc agataccatt|1440|
|acaagtttag aaaaactgg tgaagattat cataaaaatg aagatatctt ctttacaggt|1500|
|tatcaaggag accccactgg ccaaaaaacca ggtgacaaag attggtatgg tattgctaac|1560|
|ctagttgcgg accgtacgcc agcggtaggt aatactttta ctacttcttt taatacaggt|1620|
|catggtaaaa atggttcgt agatggtaag gttctaagg attctgagtg gaattatcgt|1680|
|tcagtatcag gtgttcttcc aacatggcgc tggtggcaga cttcaacagg ggaaaaactt|1740|
|cgtgcagaat atgattttac agatgcctat aatggcggaa attccccttaa attctctggt|1800|

-continued

```
gatgtagccg gtaagacaga tcaggatgtg agactttatt ctactaagtt agaagtaact    1860
gagaagacca aacttcgtgt tgcccacaag ggaggaaaag gttctaaagt ttatatggca    1920
ttctctacaa ctccagacta caaattcgat gatgcagatg catggaaaga gctaaccctt    1980
tctgacaact ggacaaatga agaatttgat ctcagctcac tagcaggtaa aaccatctat    2040
gcagtcaaac tattttttga gcatgaaggt gctgtaaaag attatcagtt caacctcgga    2100
caattaacta tctcggacaa tcaccaagag ccacaatcgc cgacaagctt ttctgtagtg    2160
aaacaatctc ttaaaaatgc ccaagaagcg gaagcagttg tgcaatttaa aggcaacaag    2220
gatgcagatt tctatgaagt ttatgaaaaa gatggagaca gctggaaatt actaactggc    2280
tcatcttcta caactattta tctaccaaaa gttagccgct cagcaagtgc tcagggtaca    2340
actcaagaac tgaaggttgt agcagtcggt aaaaatggag ttcgttcaga agctgcaacc    2400
acaacctttg attggggtat gactgtaaaa gataccagcc taccaaaacc actagctgaa    2460
aatatcgttc caggtgcaac agttattgat agtactttcc ctaagactga aggtggagaa    2520
ggtattgaag gtatgttgaa cggtaccatt actagcttgt cagataaatg gtcttcagct    2580
cagttgagtg gtagtgtgga tattcgtttg accaagccac gtaccgttgt tagatgggtc    2640
atggatcatg caggggctgg tggtgagtct gttaacgatg gcttgatgaa caccaaagac    2700
tttgaccttt attataaaga tgcagatggt gagtggaagc tagctaagga agtccgtggc    2760
aacaaagcac acgtgacaga tatcactctt gataaaccaa tcactgctca agactggcgc    2820
ttgaatgttg tcacttctga caatggaact ccatggaagg ctattcgtat ctataactgg    2880
aaaatgtatg aaaagcttga tactgagagt gtcaatattc cgatggccaa ggctgcagcc    2940
cgttctctag gcaataacaa ggtacaagtt ggctttgcag atgtacaggc tggagcaact    3000
attaccgttt atgataatcc aaattctcaa actccgctcg caaccttgaa gagcgaagtt    3060
ggaggagacc tagcaagtgc accattggat ttgacaaatc aatctggtct tctttattat    3120
cgtacccagt tgccaggcaa ggaaattagt aatgtcctag cagtttccgt tccaaaagat    3180
gacagaagaa tcaagtcagt cagcctagaa acaggaccta agaaaacaag ctacgccgaa    3240
ggggaggatt tggaccttag aggtggtgtt cttcgagttc agtatgaagg aggaactgag    3300
gacgaactca ttcgcctaac tcacgcaggt gtatcagtat caggttttga tacgcatcat    3360
aagggagaac agaatcttac tctccaatat ttgggacaac cagtaaatgc taatttgtca    3420
gtgactgtca ctggccaaga cgaagcaagt ccgaaaacta ttttgggaat tgaagtaagt    3480
cagaaaccga aaaagatta cctagttggt gatagcttag acttgtctga aggacgcttt    3540
gcagtggctt atagcaatga caccatggaa gaacattcct ttactgatga gggagttgaa    3600
atttctggtt acgatgctca aaagactggt cgtcaaacct tgacgcttcg ttaccaaggt    3660
catgaagtca actttgatgt tttggtatct ccaaaagcag cattgaacga tgagtacctc    3720
aaacaaaaat tagcagaagt tgaagctgct aagaacaagg tggtctataa ctttgcttca    3780
ccagaagtaa agaagctttt cttgaaagca attgaagcgg ccgaacaagt gttgaaagac    3840
catgaaatta gcacccaaga tcaagtcaat gaccgactta ataaattgac agaagctcat    3900
aaagctctga atggtcaaga gaaatttaag gaagaaaaga cagagcttga tcgtttaaca    3960
ggtgaggttc aagaactctt ggatgccaaa ccaaaccatc cttcaggttc tgccctagct    4020
ccgcttcttg agaaaaacaa ggtcttggtt gaaaaagtag atttgagtcc agaagagctt    4080
gcaacagcga aacagagtct aaaagatctg gttgctttat tgaaagaaga caagccagca    4140
```

```
gtcttttctg atagtaaaac aggtgttgaa gtacacttct caaataaaga gaagactgtc    4200
atcaagggtt tgaaagtaga gcgtgttcaa gcaagtgctg aagagaagaa atactttgct    4260
ggagaagatg ctcatgtctt tgaaatagaa ggtttggatg aaaaaggtca agatgttgat    4320
ctctcttacg cttctattgt gaaaatccca attgaaaaag ataagaaagt taagaaagta    4380 ttttttcttac ctgaaggcaa agaggcagta gaattggctt ttgaacaaac ggatagtcat    4440
gttatcttta cagcaccaca ctttactcat tatgcctttg tttatgaatc tgctgaaaaa    4500
ccacaacctg ctaaaccagc accacaaaac aaagtccttc aaaacctac ttatcaaccg    4560 gcttctgatc aacaaaaggc tcctaaattg aagttcaag aggaaaaggt tgcctttcat    4620
cgtcaagagc atgaaaatgc tgagatgcta gttggggaac aacgagtcat catacaggga    4680
cgagatggac tgttaagaca tgtctttgaa gttgatgaaa acggtcagcg tcgtcttcgt    4740
tcaacagaag tcatccaaga agcgattcca gaaattgttg aaattggaac aaaagtaaaa    4800
acagtaccag cagtagtagc tacacaggaa aaaccagctc aaaatacagc agttaaatca    4860
gaagaagcaa gcaaacaatt gccaaataca ggaacagctg atgctaatga agccctaata    4920
gcaggcttag ccagccttgg tcttgctagt ttagccttga ccttgagacg gaaaagagaa    4980
gataaagatt aaatatcgaa aaatcttgtg aaatctttcc g                        5021
```

<210> SEQ ID NO 3
<211> LENGTH: 913
<212> TYPE: PRT
<213> ORGANISM: Artificial Sequence
<220> FEATURE:
<223> OTHER INFORMATION: Synthetic construct

<400> SEQUENCE: 3

```
Glu Ser Lys Pro Ala Ala Glu Ala Asn Lys Thr Glu Lys Glu Val Gln
1               5                   10                  15

Pro Asp Val Pro Lys Asn Thr Glu Lys Thr Leu Lys Pro Lys Glu Ile
            20                  25                  30

Lys Phe Asn Ser Trp Glu Glu Leu Leu Lys Trp Glu Pro Gly Ala Arg
        35                  40                  45

Glu Asp Asp Ala Ile Asn Arg Gly Ser Val Val Leu Ala Ser Arg Arg
    50                  55                  60

Thr Gly His Leu Val Asn Glu Lys Ala Ser Lys Glu Ala Lys Val Gln
65                  70                  75                  80

Ala Leu Ser Asn Thr Asn Ser Lys Ala Lys Asp His Ala Ser Val Gly
                85                  90                  95

Gly Glu Glu Phe Lys Ala Tyr Ala Phe Asp Tyr Trp Gln Tyr Leu Asp
            100                 105                 110

Ser Met Val Phe Trp Glu Gly Leu Val Pro Thr Pro Asp Val Ile Asp
        115                 120                 125

Ala Gly His Arg Asn Gly Val Pro Val Tyr Gly Thr Leu Phe Phe Asn
    130                 135                 140

Trp Ser Asn Ser Ile Ala Asp Gln Glu Arg Phe Ala Glu Ala Leu Lys
145                 150                 155                 160

Gln Asp Ala Asp Gly Ser Phe Pro Ile Ala Arg Lys Leu Val Asp Met
                165                 170                 175

Ala Lys Tyr Tyr Gly Tyr Asp Gly Tyr Phe Ile Asn Gln Glu Thr Thr
            180                 185                 190

Gly Asp Leu Val Lys Pro Leu Gly Glu Lys Met Arg Gln Phe Met Leu
        195                 200                 205
```

```
Tyr Ser Lys Glu Tyr Ala Ala Lys Val Asn His Pro Ile Lys Tyr Ser
    210             215                 220

Trp Tyr Asp Ala Met Thr Tyr Asn Tyr Gly Arg Tyr His Gln Asp Gly
225             230                 235                 240

Leu Gly Glu Tyr Asn Tyr Gln Phe Met Gln Pro Glu Gly Asp Lys Val
                245                 250                 255

Pro Ala Asp Asn Phe Phe Ala Asn Phe Asn Trp Asp Lys Ala Lys Asn
            260             265                 270

Asp Tyr Thr Ile Ala Thr Ala Asn Trp Ile Gly Arg Asn Pro Tyr Asp
        275             280                 285

Val Phe Ala Gly Leu Glu Leu Gln Gln Gly Ser Tyr Lys Thr Lys
    290             295                 300

Val Lys Trp Asn Asp Ile Leu Asp Glu Asn Gly Lys Leu Arg Leu Ser
305             310                 315                 320

Leu Gly Leu Phe Ala Pro Asp Thr Ile Thr Ser Leu Gly Lys Thr Gly
                325                 330                 335

Glu Asp Tyr His Lys Asn Glu Asp Ile Phe Phe Thr Gly Tyr Gln Gly
            340                 345                 350

Asp Pro Thr Gly Gln Lys Pro Gly Asp Lys Asp Trp Tyr Gly Ile Ala
        355                 360                 365

Asn Leu Val Ala Asp Arg Thr Pro Ala Val Gly Asn Thr Phe Thr Thr
    370                 375                 380

Ser Phe Asn Thr Gly His Gly Lys Lys Trp Phe Val Asp Gly Lys Val
385                 390                 395                 400

Ser Lys Asp Ser Glu Trp Asn Tyr Arg Ser Val Ser Gly Val Leu Pro
                405                 410                 415

Thr Trp Arg Trp Trp Gln Thr Ser Thr Gly Glu Lys Leu Arg Ala Glu
            420                 425                 430

Tyr Asp Phe Thr Asp Ala Tyr Asn Gly Gly Asn Ser Leu Lys Phe Ser
        435                 440                 445

Gly Asp Val Ala Gly Lys Thr Asp Gln Asp Val Arg Leu Tyr Ser Thr
    450                 455                 460

Lys Leu Glu Val Thr Glu Lys Thr Lys Leu Arg Val Ala His Lys Gly
465                 470                 475                 480

Gly Lys Gly Ser Lys Val Tyr Met Ala Phe Ser Thr Thr Pro Asp Tyr
                485                 490                 495

Lys Phe Asp Asp Ala Asp Ala Trp Lys Glu Leu Thr Leu Ser Asp Asn
            500                 505                 510

Trp Thr Asn Glu Glu Phe Asp Leu Ser Ser Leu Ala Gly Lys Thr Ile
        515                 520                 525

Tyr Ala Val Lys Leu Phe Phe Glu His Glu Gly Ala Val Lys Asp Tyr
    530                 535                 540

Gln Phe Asn Leu Gly Gln Leu Thr Ile Ser Asp Asn His Gln Glu Pro
545                 550                 555                 560

Gln Ser Pro Thr Ser Phe Ser Val Val Lys Gln Ser Leu Lys Asn Ala
                565                 570                 575

Gln Glu Ala Glu Ala Val Val Gln Phe Lys Gly Asn Lys Asp Ala Asp
            580                 585                 590

Phe Tyr Glu Val Tyr Glu Lys Asp Gly Asp Ser Trp Lys Leu Leu Thr
        595                 600                 605

Gly Ser Ser Ser Thr Thr Ile Tyr Leu Pro Lys Val Ser Arg Ser Ala
    610                 615                 620

Ser Ala Gln Gly Thr Thr Gln Glu Leu Lys Val Val Ala Val Gly Lys
```

```
                625                 630                 635                 640
     Asn Gly Val Arg Ser Glu Ala Ala Thr Thr Thr Phe Asp Trp Gly Met
                     645                 650                 655

Thr Val Lys Asp Thr Ser Leu Pro Lys Pro Leu Ala Glu Asn Ile Val
                     660                 665                 670

Pro Gly Ala Thr Val Ile Asp Ser Thr Phe Pro Lys Thr Glu Gly Gly
                     675                 680                 685

Glu Gly Ile Glu Gly Met Leu Asn Gly Thr Ile Thr Ser Leu Ser Asp
                     690                 695                 700

Lys Trp Ser Ser Ala Gln Leu Ser Gly Ser Val Asp Ile Arg Leu Thr
     705                 710                 715                 720

Lys Pro Arg Thr Val Val Arg Trp Val Met Asp His Ala Gly Ala Gly
                     725                 730                 735

Gly Glu Ser Val Asn Asp Gly Leu Met Asn Thr Lys Asp Phe Asp Leu
                     740                 745                 750

Tyr Tyr Lys Asp Ala Asp Gly Glu Trp Lys Leu Ala Lys Glu Val Arg
                     755                 760                 765

Gly Asn Lys Ala His Val Thr Asp Ile Thr Leu Asp Lys Pro Ile Thr
                     770                 775                 780

Ala Gln Asp Trp Arg Leu Asn Val Val Thr Ser Asp Asn Gly Thr Pro
     785                 790                 795                 800

Trp Lys Ala Ile Arg Ile Tyr Asn Trp Lys Met Tyr Glu Lys Leu Asp
                     805                 810                 815

Thr Glu Ser Val Asn Ile Pro Met Ala Lys Ala Ala Arg Ser Leu
                     820                 825                 830

Gly Asn Asn Lys Val Gln Val Gly Phe Ala Asp Val Gln Ala Gly Ala
                     835                 840                 845

Thr Ile Thr Val Tyr Asp Asn Pro Asn Ser Gln Thr Pro Leu Ala Thr
                     850                 855                 860

Leu Lys Ser Glu Val Gly Gly Asp Leu Ala Ser Ala Pro Leu Asp Leu
     865                 870                 875                 880

Thr Asn Gln Ser Gly Leu Leu Tyr Tyr Arg Thr Gln Leu Pro Gly Lys
                     885                 890                 895

Glu Ile Ser Asn Val Leu Ala Val Ser Val Pro Lys Asp Asp Arg Arg
                     900                 905                 910

Ile

<210> SEQ ID NO 4
<211> LENGTH: 1646
<212> TYPE: PRT
<213> ORGANISM: Artificial Sequence
<220> FEATURE:
<223> OTHER INFORMATION: Synthetic Construct

<400> SEQUENCE: 4

Met Lys Asn Pro Phe Phe Glu Arg Arg Cys Arg Tyr Ser Ile Arg Lys
     1               5                   10                  15

Leu Ser Val Gly Ala Cys Ser Leu Met Ile Gly Ala Val Leu Phe Val
                     20                  25                  30

Gly Pro Ala Leu Ala Glu Glu Thr Ala Val Pro Glu Asn Ser Gly Ala
                     35                  40                  45

Asn Thr Glu Leu Val Ser Gly Glu Ser Glu His Ser Thr Asn Glu Ala
                     50                  55                  60

Asp Lys Gln Asn Glu Gly Glu His Thr Arg Glu Asn Lys Leu Glu Lys
     65                  70                  75                  80
```

-continued

```
Ala Glu Gly Val Ala Thr Ala Ser Glu Thr Ala Glu Ala Ser Ala
                85                  90                  95
Ala Lys Pro Glu Glu Lys Ala Gly Glu Val Val Ala Glu Thr Pro Ser
            100                 105                 110
Ala Glu Ala Lys Pro Lys Ser Asp Lys Glu Thr Glu Ala Lys Pro Glu
            115                 120                 125
Ala Thr Asn Gln Gly Asp Glu Ser Lys Pro Ala Ala Glu Ala Asn Lys
            130                 135                 140
Thr Glu Lys Glu Val Gln Pro Asp Val Pro Lys Asn Thr Glu Lys Thr
145                 150                 155                 160
Leu Lys Pro Lys Glu Ile Lys Phe Asn Ser Trp Glu Glu Leu Leu Lys
                165                 170                 175
Trp Glu Pro Gly Ala Arg Glu Asp Ala Ile Asn Arg Gly Ser Val
            180                 185                 190
Val Leu Ala Ser Arg Arg Thr Gly His Leu Val Asn Glu Lys Ala Ser
            195                 200                 205
Lys Glu Ala Lys Val Gln Ala Leu Ser Asn Thr Asn Ser Lys Ala Lys
            210                 215                 220
Asp His Ala Ser Val Gly Gly Glu Glu Phe Lys Ala Tyr Ala Phe Asp
225                 230                 235                 240
Tyr Trp Gln Tyr Leu Asp Ser Met Val Phe Trp Glu Gly Leu Val Pro
                245                 250                 255
Thr Pro Asp Val Ile Asp Ala Gly His Arg Asn Gly Val Pro Val Tyr
            260                 265                 270
Gly Thr Leu Phe Phe Asn Trp Ser Asn Ser Ile Ala Asp Gln Glu Arg
            275                 280                 285
Phe Ala Glu Ala Leu Lys Gln Asp Ala Asp Gly Ser Phe Pro Ile Ala
            290                 295                 300
Arg Lys Leu Val Asp Met Ala Lys Tyr Tyr Gly Tyr Asp Gly Tyr Phe
305                 310                 315                 320
Ile Gln Gln Glu Thr Thr Gly Asp Leu Val Lys Pro Leu Gly Glu Lys
                325                 330                 335
Met Arg Gln Phe Met Leu Tyr Ser Lys Glu Tyr Ala Ala Lys Val Asn
            340                 345                 350
His Pro Ile Lys Tyr Ser Trp Tyr Asp Ala Met Thr Tyr Asn Tyr Gly
            355                 360                 365
Arg Tyr His Gln Asp Gly Leu Gly Glu Tyr Asn Tyr Gln Phe Met Gln
            370                 375                 380
Pro Glu Gly Asp Lys Val Pro Ala Asp Asn Phe Ala Asn Phe Asn
385                 390                 395                 400
Trp Asp Lys Ala Lys Asn Asp Tyr Thr Ile Ala Thr Ala Asn Trp Ile
                405                 410                 415
Gly Arg Asn Pro Tyr Asp Val Phe Ala Gly Leu Glu Leu Gln Gln Gly
            420                 425                 430
Gly Ser Tyr Lys Thr Lys Val Lys Trp Asn Asp Ile Leu Asp Glu Asn
            435                 440                 445
Gly Lys Leu Arg Leu Ser Leu Gly Leu Phe Ala Pro Asp Thr Ile Thr
            450                 455                 460
Ser Leu Gly Lys Thr Gly Glu Asp Tyr His Lys Asn Glu Asp Ile Phe
465                 470                 475                 480
Phe Thr Gly Tyr Gln Gly Asp Pro Thr Gly Gln Lys Pro Gly Asp Lys
                485                 490                 495
```

-continued

Asp Trp Tyr Gly Ile Ala Asn Leu Val Ala Asp Arg Thr Pro Ala Val
            500                 505                 510

Gly Asn Thr Phe Thr Thr Ser Phe Asn Thr Gly His Gly Lys Lys Trp
        515                 520                 525

Phe Val Asp Gly Lys Val Ser Lys Asp Ser Glu Trp Asn Tyr Arg Ser
    530                 535                 540

Val Ser Gly Val Leu Pro Thr Trp Arg Trp Gln Thr Ser Thr Gly
545                 550                 555                 560

Glu Lys Leu Arg Ala Glu Tyr Asp Phe Thr Asp Ala Tyr Asn Gly Gly
                565                 570                 575

Asn Ser Leu Lys Phe Ser Gly Asp Val Ala Gly Lys Thr Asp Gln Asp
            580                 585                 590

Val Arg Leu Tyr Ser Thr Lys Leu Glu Val Thr Glu Lys Thr Lys Leu
        595                 600                 605

Arg Val Ala His Lys Gly Gly Lys Gly Ser Lys Val Tyr Met Ala Phe
    610                 615                 620

Ser Thr Thr Pro Asp Tyr Lys Phe Asp Asp Ala Asp Ala Trp Lys Glu
625                 630                 635                 640

Leu Thr Leu Ser Asp Asn Trp Thr Asn Glu Glu Phe Asp Leu Ser Ser
                645                 650                 655

Leu Ala Gly Lys Thr Ile Tyr Ala Val Lys Leu Phe Phe Glu His Glu
            660                 665                 670

Gly Ala Val Lys Asp Tyr Gln Phe Asn Leu Gly Gln Leu Thr Ile Ser
        675                 680                 685

Asp Asn His Gln Glu Pro Gln Ser Pro Thr Ser Phe Ser Val Val Lys
    690                 695                 700

Gln Ser Leu Lys Asn Ala Gln Glu Ala Glu Ala Val Val Gln Phe Lys
705                 710                 715                 720

Gly Asn Lys Asp Ala Asp Phe Tyr Glu Val Tyr Glu Lys Asp Gly Asp
                725                 730                 735

Ser Trp Lys Leu Leu Thr Gly Ser Ser Thr Thr Ile Tyr Leu Pro
            740                 745                 750

Lys Val Ser Arg Ser Ala Ser Ala Gln Gly Thr Thr Gln Glu Leu Lys
        755                 760                 765

Val Val Ala Val Gly Lys Asn Gly Val Arg Ser Glu Ala Ala Thr Thr
    770                 775                 780

Thr Phe Asp Trp Gly Met Thr Val Lys Asp Thr Ser Leu Pro Lys Pro
785                 790                 795                 800

Leu Ala Glu Asn Ile Val Pro Gly Ala Thr Val Ile Asp Ser Thr Phe
                805                 810                 815

Pro Lys Thr Glu Gly Gly Glu Gly Ile Glu Gly Met Leu Asn Gly Thr
            820                 825                 830

Ile Thr Ser Leu Ser Asp Lys Trp Ser Ser Ala Gln Leu Ser Gly Ser
        835                 840                 845

Val Asp Ile Arg Leu Thr Lys Pro Arg Thr Val Arg Trp Val Met
    850                 855                 860

Asp His Ala Gly Ala Gly Gly Glu Ser Val Asn Asp Gly Leu Met Asn
865                 870                 875                 880

Thr Lys Asp Phe Asp Leu Tyr Tyr Lys Asp Ala Asp Gly Glu Trp Lys
                885                 890                 895

Leu Ala Lys Glu Val Arg Gly Asn Lys Ala His Val Thr Asp Ile Thr
            900                 905                 910

Leu Asp Lys Pro Ile Thr Ala Gln Asp Trp Arg Leu Asn Val Val Thr

-continued

|     |     |     |
| --- | --- | --- |
| 915 | 920 | 925 |

Ser Asp Asn Gly Thr Pro Trp Lys Ala Ile Arg Ile Tyr Asn Trp Lys
          930                 935                 940

Met Tyr Glu Lys Leu Asp Thr Glu Ser Val Asn Ile Pro Met Ala Lys
945                 950                 955                 960

Ala Ala Ala Arg Ser Leu Gly Asn Asn Lys Val Gln Val Gly Phe Ala
              965                 970                 975

Asp Val Gln Ala Gly Ala Thr Ile Thr Val Tyr Asp Asn Pro Asn Ser
              980                 985                 990

Gln Thr Pro Leu Ala Thr Leu Lys Ser Glu Val Gly Gly Asp Leu Ala
              995                1000                1005

Ser Ala Pro Leu Asp Leu Thr Asn Gln Ser Gly Leu Leu Tyr Tyr
      1010                1015                1020

Arg Thr Gln Leu Pro Gly Lys Glu Ile Ser Asn Val Leu Ala Val
      1025                1030                1035

Ser Val Pro Lys Asp Arg Arg Ile Lys Ser Val Ser Leu Glu
      1040                1045                1050

Thr Gly Pro Lys Lys Thr Ser Tyr Ala Glu Gly Glu Asp Leu Asp
      1055                1060                1065

Leu Arg Gly Gly Val Leu Arg Val Gln Tyr Glu Gly Gly Thr Glu
      1070                1075                1080

Asp Glu Leu Ile Arg Leu Thr His Ala Gly Val Ser Val Ser Gly
      1085                1090                1095

Phe Asp Thr His His Lys Gly Glu Gln Asn Leu Thr Leu Gln Tyr
      1100                1105                1110

Leu Gly Gln Pro Val Asn Ala Asn Leu Ser Val Thr Val Thr Gly
      1115                1120                1125

Gln Asp Glu Ala Ser Pro Lys Thr Ile Leu Gly Ile Glu Val Ser
      1130                1135                1140

Gln Lys Pro Lys Lys Asp Tyr Leu Val Gly Asp Ser Leu Asp Leu
      1145                1150                1155

Ser Glu Gly Arg Phe Ala Val Ala Tyr Ser Asn Asp Thr Met Glu
      1160                1165                1170

Glu His Ser Phe Thr Asp Glu Gly Val Glu Ile Ser Gly Tyr Asp
      1175                1180                1185

Ala Gln Lys Thr Gly Arg Gln Thr Leu Thr Leu Arg Tyr Gln Gly
      1190                1195                1200

His Glu Val Asn Phe Asp Val Leu Val Ser Pro Lys Ala Ala Leu
      1205                1210                1215

Asn Asp Glu Tyr Leu Lys Gln Lys Leu Ala Glu Val Glu Ala Ala
      1220                1225                1230

Lys Asn Lys Val Val Tyr Asn Phe Ala Ser Pro Glu Val Lys Glu
      1235                1240                1245

Ala Phe Leu Lys Ala Ile Glu Ala Ala Glu Gln Val Leu Lys Asp
      1250                1255                1260

His Glu Ile Ser Thr Gln Asp Gln Val Asn Asp Arg Leu Asn Lys
      1265                1270                1275

Leu Thr Glu Ala His Lys Ala Leu Asn Gly Gln Glu Lys Phe Lys
      1280                1285                1290

Glu Glu Lys Thr Glu Leu Asp Arg Leu Thr Gly Glu Val Gln Glu
      1295                1300                1305

Leu Leu Asp Ala Lys Pro Asn His Pro Ser Gly Ser Ala Leu Ala
      1310                1315                1320

```
Pro Leu Leu Glu Lys Asn Lys Val Leu Val Glu Lys Val Asp Leu
    1325                1330                1335

Ser Pro Glu Glu Leu Ala Thr Ala Lys Gln Ser Leu Lys Asp Leu
    1340                1345                1350

Val Ala Leu Leu Lys Glu Asp Lys Pro Ala Val Phe Ser Asp Ser
    1355                1360                1365

Lys Thr Gly Val Glu Val His Phe Ser Asn Lys Glu Lys Thr Val
    1370                1375                1380

Ile Lys Gly Leu Lys Val Glu Arg Val Gln Ala Ser Ala Glu Glu
    1385                1390                1395

Lys Lys Tyr Phe Ala Gly Glu Asp Ala His Val Phe Glu Ile Glu
    1400                1405                1410

Gly Leu Asp Glu Lys Gly Gln Asp Val Asp Leu Ser Tyr Ala Ser
    1415                1420                1425

Ile Val Lys Ile Pro Ile Glu Lys Asp Lys Val Lys Lys Val
    1430                1435                1440

Phe Phe Leu Pro Glu Gly Lys Glu Ala Val Glu Leu Ala Phe Glu
    1445                1450                1455

Gln Thr Asp Ser His Val Ile Phe Thr Ala Pro His Phe Thr His
    1460                1465                1470

Tyr Ala Phe Val Tyr Glu Ser Ala Glu Lys Pro Gln Pro Ala Lys
    1475                1480                1485

Pro Ala Pro Gln Asn Lys Val Leu Pro Lys Pro Thr Tyr Gln Pro
    1490                1495                1500

Ala Ser Asp Gln Gln Lys Ala Pro Lys Leu Glu Val Gln Glu Glu
    1505                1510                1515

Lys Val Ala Phe His Arg Gln Glu His Glu Asn Ala Glu Met Leu
    1520                1525                1530

Val Gly Glu Gln Arg Val Ile Ile Gln Gly Arg Asp Gly Leu Leu
    1535                1540                1545

Arg His Val Phe Glu Val Asp Glu Asn Gly Gln Arg Arg Leu Arg
    1550                1555                1560

Ser Thr Glu Val Ile Gln Glu Ala Ile Pro Glu Ile Val Glu Ile
    1565                1570                1575

Gly Thr Lys Val Lys Thr Val Pro Ala Val Val Ala Thr Gln Glu
    1580                1585                1590

Lys Pro Ala Gln Asn Thr Ala Val Lys Ser Glu Glu Ala Ser Lys
    1595                1600                1605

Gln Leu Pro Asn Thr Gly Thr Ala Asp Ala Asn Glu Ala Leu Ile
    1610                1615                1620

Ala Gly Leu Ala Ser Leu Gly Leu Ala Ser Leu Ala Leu Thr Leu
    1625                1630                1635

Arg Arg Lys Arg Glu Asp Lys Asp
    1640                1645

<210> SEQ ID NO 5
<211> LENGTH: 1646
<212> TYPE: PRT
<213> ORGANISM: Artificial Sequence
<220> FEATURE:
<223> OTHER INFORMATION: Synthetic Construct

<400> SEQUENCE: 5

Met Lys Asn Pro Phe Phe Glu Arg Arg Cys Arg Tyr Ser Ile Arg Lys
1               5                   10                  15
```

```
Leu Ser Val Gly Ala Cys Ser Leu Met Ile Gly Ala Val Leu Phe Val
            20                  25                  30
Gly Pro Ala Leu Ala Glu Glu Thr Ala Val Pro Glu Asn Ser Gly Ala
            35                  40                  45
Asn Thr Glu Leu Val Ser Gly Glu Ser Glu His Ser Thr Asn Glu Ala
 50                  55                  60
Asp Lys Gln Asn Glu Gly Glu His Thr Arg Glu Asn Lys Leu Glu Lys
 65                  70                  75                  80
Ala Glu Gly Val Ala Thr Ala Ser Glu Thr Ala Glu Ala Ala Ser Ala
                 85                  90                  95
Ala Lys Pro Glu Glu Lys Ala Gly Glu Val Val Ala Glu Thr Pro Ser
            100                 105                 110
Ala Glu Ala Lys Pro Lys Ser Asp Lys Glu Thr Glu Ala Lys Pro Glu
            115                 120                 125
Ala Thr Asn Gln Gly Asp Glu Ser Lys Pro Ala Ala Glu Ala Asn Lys
            130                 135                 140
Thr Glu Lys Glu Val Gln Pro Asp Val Pro Lys Asn Thr Glu Lys Thr
145                 150                 155                 160
Leu Lys Pro Lys Glu Ile Lys Phe Asn Ser Trp Glu Glu Leu Leu Lys
                165                 170                 175
Trp Glu Pro Gly Ala Arg Glu Asp Ala Ile Asn Arg Gly Ser Val
            180                 185                 190
Val Leu Ala Ser Arg Arg Thr Gly His Leu Val Asn Glu Lys Ala Ser
            195                 200                 205
Lys Glu Ala Lys Val Gln Ala Leu Ser Asn Thr Asn Ser Lys Ala Lys
            210                 215                 220
Asp His Ala Ser Val Gly Gly Glu Glu Phe Lys Ala Tyr Ala Phe Asp
225                 230                 235                 240
Tyr Trp Gln Tyr Leu Asp Ser Met Val Phe Trp Glu Gly Leu Val Pro
                245                 250                 255
Thr Pro Asp Val Ile Asp Ala Gly His Arg Asn Gly Val Pro Val Tyr
            260                 265                 270
Gly Thr Leu Phe Phe Asn Trp Ser Asn Ser Ile Ala Asp Gln Glu Arg
            275                 280                 285
Phe Ala Glu Ala Leu Lys Gln Asp Ala Asp Gly Ser Phe Pro Ile Ala
290                 295                 300
Arg Lys Leu Val Asp Met Ala Lys Tyr Tyr Gly Tyr Asp Gly Tyr Phe
305                 310                 315                 320
Ile Ala Gln Glu Thr Thr Gly Asp Leu Val Lys Pro Leu Gly Glu Lys
                325                 330                 335
Met Arg Gln Phe Met Leu Tyr Ser Lys Glu Tyr Ala Ala Lys Val Asn
            340                 345                 350
His Pro Ile Lys Tyr Ser Trp Tyr Asp Ala Met Thr Tyr Asn Tyr Gly
            355                 360                 365
Arg Tyr His Gln Asp Gly Leu Gly Glu Tyr Asn Gln Phe Met Gln
            370                 375                 380
Pro Glu Gly Asp Lys Val Pro Ala Asp Phe Phe Ala Asn Phe Asn
385                 390                 395                 400
Trp Asp Lys Ala Lys Asn Asp Tyr Thr Ile Ala Thr Ala Asn Trp Ile
                405                 410                 415
Gly Arg Asn Pro Tyr Asp Val Phe Ala Gly Leu Glu Leu Gln Gln Gly
            420                 425                 430
```

-continued

Gly Ser Tyr Lys Thr Lys Val Lys Trp Asn Asp Ile Leu Asp Glu Asn
            435                 440                 445

Gly Lys Leu Arg Leu Ser Leu Gly Leu Phe Ala Pro Asp Thr Ile Thr
    450                 455                 460

Ser Leu Gly Lys Thr Gly Glu Asp Tyr His Lys Asn Glu Asp Ile Phe
465                 470                 475                 480

Phe Thr Gly Tyr Gln Gly Asp Pro Thr Gly Gln Lys Pro Gly Asp Lys
                485                 490                 495

Asp Trp Tyr Gly Ile Ala Asn Leu Val Ala Asp Arg Thr Pro Ala Val
                500                 505                 510

Gly Asn Thr Phe Thr Thr Ser Phe Asn Thr Gly His Gly Lys Lys Trp
                515                 520                 525

Phe Val Asp Gly Lys Val Ser Lys Asp Ser Glu Trp Asn Tyr Arg Ser
530                 535                 540

Val Ser Gly Val Leu Pro Thr Trp Arg Trp Gln Thr Ser Thr Gly
545                 550                 555                 560

Glu Lys Leu Arg Ala Glu Tyr Asp Phe Thr Asp Ala Tyr Asn Gly Gly
                565                 570                 575

Asn Ser Leu Lys Phe Ser Gly Asp Val Ala Gly Lys Thr Asp Gln Asp
                580                 585                 590

Val Arg Leu Tyr Ser Thr Lys Leu Glu Val Thr Glu Lys Thr Lys Leu
                595                 600                 605

Arg Val Ala His Lys Gly Lys Gly Ser Lys Val Tyr Met Ala Phe
                610                 615                 620

Ser Thr Thr Pro Asp Tyr Lys Phe Asp Asp Ala Asp Trp Lys Glu
625                 630                 635                 640

Leu Thr Leu Ser Asp Asn Trp Thr Asn Glu Glu Phe Asp Leu Ser Ser
                645                 650                 655

Leu Ala Gly Lys Thr Ile Tyr Ala Val Lys Leu Phe Phe Glu His Glu
                660                 665                 670

Gly Ala Val Lys Asp Tyr Gln Phe Asn Leu Gly Gln Leu Thr Ile Ser
                675                 680                 685

Asp Asn His Gln Glu Pro Gln Ser Pro Thr Ser Phe Ser Val Val Lys
690                 695                 700

Gln Ser Leu Lys Asn Ala Gln Glu Ala Glu Ala Val Gln Phe Lys
705                 710                 715                 720

Gly Asn Lys Asp Ala Asp Phe Tyr Glu Val Tyr Glu Lys Asp Gly Asp
                725                 730                 735

Ser Trp Lys Leu Leu Thr Gly Ser Ser Ser Thr Thr Ile Tyr Leu Pro
                740                 745                 750

Lys Val Ser Arg Ser Ala Ser Ala Gln Gly Thr Thr Gln Glu Leu Lys
                755                 760                 765

Val Val Ala Val Gly Lys Asn Gly Val Arg Ser Glu Ala Ala Thr Thr
770                 775                 780

Thr Phe Asp Trp Gly Met Thr Val Lys Asp Thr Ser Leu Pro Lys Pro
785                 790                 795                 800

Leu Ala Glu Asn Ile Val Pro Gly Ala Thr Val Ile Asp Ser Thr Phe
                805                 810                 815

Pro Lys Thr Glu Gly Gly Glu Gly Ile Glu Gly Met Leu Asn Gly Thr
                820                 825                 830

Ile Thr Ser Leu Ser Asp Lys Trp Ser Ser Ala Gln Leu Ser Gly Ser
                835                 840                 845

Val Asp Ile Arg Leu Thr Lys Pro Arg Thr Val Val Arg Trp Val Met

-continued

```
            850                 855                 860
Asp His Ala Gly Ala Gly Glu Ser Val Asn Asp Gly Leu Met Asn
865                 870                 875                 880

Thr Lys Asp Phe Asp Leu Tyr Tyr Lys Asp Ala Asp Gly Glu Trp Lys
            885                 890                 895

Leu Ala Lys Glu Val Arg Gly Asn Lys Ala His Val Thr Asp Ile Thr
                900                 905                 910

Leu Asp Lys Pro Ile Thr Ala Gln Asp Trp Arg Leu Asn Val Val Thr
            915                 920                 925

Ser Asp Asn Gly Thr Pro Trp Lys Ala Ile Arg Ile Tyr Asn Trp Lys
            930                 935                 940

Met Tyr Glu Lys Leu Asp Thr Glu Ser Val Asn Ile Pro Met Ala Lys
945                 950                 955                 960

Ala Ala Ala Arg Ser Leu Gly Asn Asn Lys Val Gln Val Gly Phe Ala
                965                 970                 975

Asp Val Gln Ala Gly Ala Thr Ile Thr Val Tyr Asp Asn Pro Asn Ser
                980                 985                 990

Gln Thr Pro Leu Ala Thr Leu Lys  Ser Glu Val Gly Gly  Asp Leu Ala
            995                 1000                1005

Ser Ala  Pro Leu Asp Leu Thr  Asn Gln Ser Gly Leu  Leu Tyr Tyr
        1010                1015                1020

Arg Thr  Gln Leu Pro Gly Lys  Glu Ile Ser Asn Val  Leu Ala Val
        1025                1030                1035

Ser Val  Pro Lys Asp Arg  Arg Ile Lys Ser Val  Ser Leu Glu
        1040                1045                1050

Thr Gly  Pro Lys Lys Thr Ser  Tyr Ala Glu Gly Glu  Asp Leu Asp
        1055                1060                1065

Leu Arg  Gly Gly Val Leu Arg  Val Gln Tyr Glu Gly  Gly Thr Glu
        1070                1075                1080

Asp Glu  Leu Ile Arg Leu Thr  His Ala Gly Val Ser  Val Ser Gly
        1085                1090                1095

Phe Asp  Thr His His Lys Gly  Glu Gln Asn Leu Thr  Leu Gln Tyr
        1100                1105                1110

Leu Gly  Gln Pro Val Asn Ala  Asn Leu Ser Val Thr  Val Thr Gly
        1115                1120                1125

Gln Asp  Glu Ala Ser Pro Lys  Thr Ile Leu Gly Ile  Glu Val Ser
        1130                1135                1140

Gln Lys  Pro Lys Lys Asp Tyr  Leu Val Gly Asp Ser  Leu Asp Leu
        1145                1150                1155

Ser Glu  Gly Arg Phe Ala Val  Ala Tyr Ser Asn Asp  Thr Met Glu
        1160                1165                1170

Glu His  Ser Phe Thr Asp Glu  Gly Val Glu Ile Ser  Gly Tyr Asp
        1175                1180                1185

Ala Gln  Lys Thr Gly Arg Gln  Thr Leu Thr Leu Arg  Tyr Gln Gly
        1190                1195                1200

His Glu  Val Asn Phe Asp Val  Leu Val Ser Pro Lys  Ala Ala Leu
        1205                1210                1215

Asn Asp  Glu Tyr Leu Lys Gln  Lys Leu Ala Glu Val  Glu Ala Ala
        1220                1225                1230

Lys Asn  Lys Val Val Tyr Asn  Phe Ala Ser Pro Glu  Val Lys Glu
        1235                1240                1245

Ala Phe  Leu Lys Ala Ile Glu  Ala Ala Glu Gln Val  Leu Lys Asp
        1250                1255                1260
```

```
His Glu Ile Ser Thr Gln Asp Gln Val Asn Asp Arg Leu Asn Lys
1265                 1270                1275

Leu Thr Glu Ala His Lys Ala Leu Asn Gly Gln Glu Lys Phe Lys
1280                 1285                1290

Glu Glu Lys Thr Glu Leu Asp Arg Leu Thr Gly Glu Val Gln Glu
1295                 1300                1305

Leu Leu Asp Ala Lys Pro Asn His Pro Ser Gly Ser Ala Leu Ala
1310                 1315                1320

Pro Leu Leu Glu Lys Asn Lys Val Leu Val Glu Lys Val Asp Leu
1325                 1330                1335

Ser Pro Glu Glu Leu Ala Thr Ala Lys Gln Ser Leu Lys Asp Leu
1340                 1345                1350

Val Ala Leu Leu Lys Glu Asp Lys Pro Ala Val Phe Ser Asp Ser
1355                 1360                1365

Lys Thr Gly Val Glu Val His Phe Ser Asn Lys Glu Lys Thr Val
1370                 1375                1380

Ile Lys Gly Leu Lys Val Glu Arg Val Gln Ala Ser Ala Glu Glu
1385                 1390                1395

Lys Lys Tyr Phe Ala Gly Glu Asp Ala His Val Phe Glu Ile Glu
1400                 1405                1410

Gly Leu Asp Glu Lys Gly Gln Asp Val Asp Leu Ser Tyr Ala Ser
1415                 1420                1425

Ile Val Lys Ile Pro Ile Glu Lys Asp Lys Val Lys Lys Val
1430                 1435                1440

Phe Phe Leu Pro Glu Gly Lys Glu Ala Val Glu Leu Ala Phe Glu
1445                 1450                1455

Gln Thr Asp Ser His Val Ile Phe Thr Ala Pro His Phe Thr His
1460                 1465                1470

Tyr Ala Phe Val Tyr Glu Ser Ala Glu Lys Pro Gln Pro Ala Lys
1475                 1480                1485

Pro Ala Pro Gln Asn Lys Val Leu Pro Lys Pro Thr Tyr Gln Pro
1490                 1495                1500

Ala Ser Asp Gln Gln Lys Ala Pro Lys Leu Glu Val Gln Glu Glu
1505                 1510                1515

Lys Val Ala Phe His Arg Gln Glu His Glu Asn Ala Glu Met Leu
1520                 1525                1530

Val Gly Glu Gln Arg Val Ile Gln Gly Arg Asp Gly Leu Leu
1535                 1540                1545

Arg His Val Phe Glu Val Asp Glu Asn Gly Gln Arg Arg Leu Arg
1550                 1555                1560

Ser Thr Glu Val Ile Gln Glu Ala Ile Pro Glu Ile Val Glu Ile
1565                 1570                1575

Gly Thr Lys Val Lys Thr Val Pro Ala Val Val Ala Thr Gln Glu
1580                 1585                1590

Lys Pro Ala Gln Asn Thr Ala Val Lys Ser Glu Glu Ala Ser Lys
1595                 1600                1605

Gln Leu Pro Asn Thr Gly Thr Ala Asp Ala Asn Glu Ala Leu Ile
1610                 1615                1620

Ala Gly Leu Ala Ser Leu Gly Leu Ala Ser Leu Ala Leu Thr Leu
1625                 1630                1635

Arg Arg Lys Arg Glu Asp Lys Asp
1640                 1645
```

<210> SEQ ID NO 6
<211> LENGTH: 1646
<212> TYPE: PRT
<213> ORGANISM: Artificial Sequence
<220> FEATURE:
<223> OTHER INFORMATION: Synthetic Construct

<400> SEQUENCE: 6

```
Met Lys Asn Pro Phe Glu Arg Arg Cys Arg Tyr Ser Ile Arg Lys
1               5                   10                  15

Leu Ser Val Gly Ala Cys Ser Leu Met Ile Gly Ala Val Leu Phe Val
                20                  25                  30

Gly Pro Ala Leu Ala Glu Glu Thr Ala Val Pro Glu Asn Ser Gly Ala
                35                  40                  45

Asn Thr Glu Leu Val Ser Gly Ser Glu His Ser Thr Asn Glu Ala
        50                  55                  60

Asp Lys Gln Asn Glu Gly Glu His Thr Arg Glu Asn Lys Leu Glu Lys
65                  70                  75                  80

Ala Glu Gly Val Ala Thr Ala Ser Glu Thr Ala Glu Ala Ala Ser Ala
                85                  90                  95

Ala Lys Pro Glu Glu Lys Ala Gly Glu Val Val Ala Glu Thr Pro Ser
            100                 105                 110

Ala Glu Ala Lys Pro Lys Ser Asp Lys Glu Thr Glu Ala Lys Pro Glu
        115                 120                 125

Ala Thr Asn Gln Gly Asp Glu Ser Lys Pro Ala Ala Glu Ala Asn Lys
    130                 135                 140

Thr Glu Lys Glu Val Gln Pro Asp Val Pro Lys Asn Thr Glu Lys Thr
145                 150                 155                 160

Leu Lys Pro Lys Glu Ile Lys Phe Asn Ser Trp Glu Glu Leu Leu Lys
                165                 170                 175

Trp Glu Pro Gly Ala Arg Glu Asp Asp Ala Ile Asn Arg Gly Ser Val
            180                 185                 190

Val Leu Ala Ser Arg Arg Thr Gly His Leu Val Asn Glu Lys Ala Ser
        195                 200                 205

Lys Glu Ala Lys Val Gln Ala Leu Ser Asn Thr Asn Ser Lys Ala Lys
    210                 215                 220

Asp His Ala Ser Val Gly Gly Glu Glu Phe Lys Ala Tyr Ala Phe Asp
225                 230                 235                 240

Tyr Trp Gln Tyr Leu Asp Ser Met Val Phe Trp Gly Leu Val Pro
                245                 250                 255

Thr Pro Asp Val Ile Asp Ala Gly His Arg Asn Gly Val Pro Val Tyr
            260                 265                 270

Gly Thr Leu Phe Phe Asn Trp Ser Asn Ser Ile Ala Asp Gln Glu Arg
        275                 280                 285

Phe Ala Glu Ala Leu Lys Gln Asp Ala Asp Gly Ser Phe Pro Ile Ala
    290                 295                 300

Arg Lys Leu Val Asp Met Ala Lys Tyr Tyr Tyr Asp Gly Tyr Phe
305                 310                 315                 320

Ile Asn Gln Gln Thr Thr Gly Asp Leu Val Lys Pro Leu Gly Glu Lys
                325                 330                 335

Met Arg Gln Phe Met Leu Tyr Ser Lys Glu Tyr Ala Ala Lys Val Asn
            340                 345                 350

His Pro Ile Lys Tyr Ser Trp Tyr Asp Ala Met Thr Tyr Asn Tyr Gly
        355                 360                 365
```

-continued

```
Arg Tyr His Gln Asp Gly Leu Gly Glu Tyr Asn Tyr Gln Phe Met Gln
370                 375                 380

Pro Glu Gly Asp Lys Val Pro Ala Asp Asn Phe Phe Ala Asn Phe Asn
385                 390                 395                 400

Trp Asp Lys Ala Lys Asn Asp Tyr Thr Ile Ala Thr Ala Asn Trp Ile
                405                 410                 415

Gly Arg Asn Pro Tyr Asp Val Phe Ala Gly Leu Glu Leu Gln Gln Gly
                420                 425                 430

Gly Ser Tyr Lys Thr Lys Val Lys Trp Asn Asp Ile Leu Asp Glu Asn
            435                 440                 445

Gly Lys Leu Arg Leu Ser Leu Gly Leu Phe Ala Pro Asp Thr Ile Thr
450                 455                 460

Ser Leu Gly Lys Thr Gly Glu Asp Tyr His Lys Asn Glu Asp Ile Phe
465                 470                 475                 480

Phe Thr Gly Tyr Gln Gly Asp Pro Thr Gly Gln Lys Pro Gly Asp Lys
                485                 490                 495

Asp Trp Tyr Gly Ile Ala Asn Leu Val Ala Asp Arg Thr Pro Ala Val
                500                 505                 510

Gly Asn Thr Phe Thr Thr Ser Phe Asn Thr Gly His Gly Lys Lys Trp
            515                 520                 525

Phe Val Asp Gly Lys Val Ser Lys Asp Ser Glu Trp Asn Tyr Arg Ser
530                 535                 540

Val Ser Gly Val Leu Pro Thr Trp Arg Trp Gln Thr Ser Thr Gly
545                 550                 555                 560

Glu Lys Leu Arg Ala Glu Tyr Asp Phe Thr Asp Ala Tyr Asn Gly Gly
                565                 570                 575

Asn Ser Leu Lys Phe Ser Gly Asp Val Ala Gly Lys Thr Asp Gln Asp
            580                 585                 590

Val Arg Leu Tyr Ser Thr Lys Leu Glu Val Thr Glu Lys Thr Lys Leu
595                 600                 605

Arg Val Ala His Lys Gly Gly Lys Gly Ser Lys Val Tyr Met Ala Phe
610                 615                 620

Ser Thr Thr Pro Asp Tyr Lys Phe Asp Asp Ala Asp Ala Trp Lys Glu
625                 630                 635                 640

Leu Thr Leu Ser Asp Asn Trp Thr Asn Glu Glu Phe Asp Leu Ser Ser
                645                 650                 655

Leu Ala Gly Lys Thr Ile Tyr Ala Val Lys Leu Phe Phe Glu His Glu
                660                 665                 670

Gly Ala Val Lys Asp Tyr Gln Phe Asn Leu Gly Gln Leu Thr Ile Ser
            675                 680                 685

Asp Asn His Gln Glu Pro Gln Ser Pro Thr Ser Phe Ser Val Val Lys
690                 695                 700

Gln Ser Leu Lys Asn Ala Gln Glu Ala Glu Ala Val Val Gln Phe Lys
705                 710                 715                 720

Gly Asn Lys Asp Ala Asp Phe Tyr Glu Val Tyr Glu Lys Asp Gly Asp
                725                 730                 735

Ser Trp Lys Leu Leu Thr Gly Ser Ser Ser Thr Ile Tyr Leu Pro
                740                 745                 750

Lys Val Ser Arg Ser Ala Ser Gln Gly Thr Gln Glu Leu Lys
            755                 760                 765

Val Val Ala Val Gly Lys Asn Gly Val Arg Ser Glu Ala Ala Thr Thr
770                 775                 780

Thr Phe Asp Trp Gly Met Thr Val Lys Asp Thr Ser Leu Pro Lys Pro
```

-continued

```
            785                 790                 795                 800
Leu Ala Glu Asn Ile Val Pro Gly Ala Thr Val Ile Asp Ser Thr Phe
                    805                 810                 815
Pro Lys Thr Glu Gly Gly Gly Ile Glu Gly Met Leu Asn Gly Thr
                820                 825                 830
Ile Thr Ser Leu Ser Asp Lys Trp Ser Ser Ala Gln Leu Ser Gly Ser
                835                 840                 845
Val Asp Ile Arg Leu Thr Lys Pro Arg Thr Val Arg Trp Val Met
850                 855                 860
Asp His Ala Gly Ala Gly Gly Glu Ser Val Asn Asp Gly Leu Met Asn
865                 870                 875                 880
Thr Lys Asp Phe Asp Leu Tyr Tyr Lys Asp Ala Asp Gly Glu Trp Lys
                    885                 890                 895
Leu Ala Lys Glu Val Arg Gly Asn Lys Ala His Val Thr Asp Ile Thr
                900                 905                 910
Leu Asp Lys Pro Ile Thr Ala Gln Asp Trp Arg Leu Asn Val Val Thr
            915                 920                 925
Ser Asp Asn Gly Thr Pro Trp Lys Ala Ile Arg Ile Tyr Asn Trp Lys
930                 935                 940
Met Tyr Glu Lys Leu Asp Thr Glu Ser Val Asn Ile Pro Met Ala Lys
945                 950                 955                 960
Ala Ala Ala Arg Ser Leu Gly Asn Asn Lys Val Gln Val Gly Phe Ala
                965                 970                 975
Asp Val Gln Ala Gly Ala Thr Ile Thr Val Tyr Asp Asn Pro Asn Ser
                980                 985                 990
Gln Thr Pro Leu Ala Thr Leu Lys Ser Glu Val Gly Gly Asp Leu Ala
            995                 1000                1005
Ser Ala Pro Leu Asp Leu Thr Asn Gln Ser Gly Leu Leu Tyr Tyr
            1010                1015                1020
Arg Thr Gln Leu Pro Gly Lys Glu Ile Ser Asn Val Leu Ala Val
            1025                1030                1035
Ser Val Pro Lys Asp Asp Arg Ile Lys Ser Val Ser Leu Glu
            1040                1045                1050
Thr Gly Pro Lys Lys Thr Ser Tyr Ala Glu Gly Glu Asp Leu Asp
            1055                1060                1065
Leu Arg Gly Gly Val Leu Arg Val Gln Tyr Glu Gly Gly Thr Glu
            1070                1075                1080
Asp Glu Leu Ile Arg Leu Thr His Ala Gly Val Ser Val Ser Gly
            1085                1090                1095
Phe Asp Thr His His Lys Gly Glu Gln Asn Leu Thr Leu Gln Tyr
            1100                1105                1110
Leu Gly Gln Pro Val Asn Ala Asn Leu Ser Val Thr Val Thr Gly
            1115                1120                1125
Gln Asp Glu Ala Ser Pro Lys Thr Ile Leu Gly Ile Glu Val Ser
            1130                1135                1140
Gln Lys Pro Lys Lys Asp Tyr Leu Val Gly Asp Ser Leu Asp Leu
            1145                1150                1155
Ser Glu Gly Arg Phe Ala Val Ala Tyr Ser Asn Asp Thr Met Glu
            1160                1165                1170
Glu His Ser Phe Thr Asp Glu Gly Val Glu Ile Ser Gly Tyr Asp
            1175                1180                1185
Ala Gln Lys Thr Gly Arg Gln Thr Leu Thr Leu Arg Tyr Gln Gly
            1190                1195                1200
```

```
His Glu Val Asn Phe Asp Val Leu Val Ser Pro Lys Ala Ala Leu
1205                1210                1215

Asn Asp Glu Tyr Leu Lys Gln Lys Leu Ala Glu Val Glu Ala Ala
1220                1225                1230

Lys Asn Lys Val Val Tyr Asn Phe Ala Ser Pro Glu Val Lys Glu
1235                1240                1245

Ala Phe Leu Lys Ala Ile Glu Ala Ala Glu Gln Val Leu Lys Asp
1250                1255                1260

His Glu Ile Ser Thr Gln Asp Gln Val Asn Asp Arg Leu Asn Lys
1265                1270                1275

Leu Thr Glu Ala His Lys Ala Leu Asn Gly Gln Glu Lys Phe Lys
1280                1285                1290

Glu Glu Lys Thr Glu Leu Asp Arg Leu Thr Gly Glu Val Gln Glu
1295                1300                1305

Leu Leu Asp Ala Lys Pro Asn His Pro Ser Gly Ser Ala Leu Ala
1310                1315                1320

Pro Leu Leu Glu Lys Asn Lys Val Leu Val Glu Lys Val Asp Leu
1325                1330                1335

Ser Pro Glu Glu Leu Ala Thr Ala Lys Gln Ser Leu Lys Asp Leu
1340                1345                1350

Val Ala Leu Leu Lys Glu Asp Lys Pro Ala Val Phe Ser Asp Ser
1355                1360                1365

Lys Thr Gly Val Glu Val His Phe Ser Asn Lys Glu Lys Thr Val
1370                1375                1380

Ile Lys Gly Leu Lys Val Glu Arg Val Gln Ala Ser Ala Glu Glu
1385                1390                1395

Lys Lys Tyr Phe Ala Gly Glu Asp Ala His Val Phe Glu Ile Glu
1400                1405                1410

Gly Leu Asp Glu Lys Gly Gln Asp Val Asp Leu Ser Tyr Ala Ser
1415                1420                1425

Ile Val Lys Ile Pro Ile Glu Lys Asp Lys Lys Val Lys Lys Val
1430                1435                1440

Phe Phe Leu Pro Glu Gly Lys Glu Ala Val Glu Leu Ala Phe Glu
1445                1450                1455

Gln Thr Asp Ser His Val Ile Phe Thr Ala Pro His Phe Thr His
1460                1465                1470

Tyr Ala Phe Val Tyr Glu Ser Ala Glu Lys Pro Gln Pro Ala Lys
1475                1480                1485

Pro Ala Pro Gln Asn Lys Val Leu Pro Lys Pro Thr Tyr Gln Pro
1490                1495                1500

Ala Ser Asp Gln Gln Lys Ala Pro Lys Leu Glu Val Gln Glu Glu
1505                1510                1515

Lys Val Ala Phe His Arg Gln Glu His Glu Asn Ala Glu Met Leu
1520                1525                1530

Val Gly Glu Gln Arg Val Ile Ile Gln Gly Arg Asp Gly Leu Leu
1535                1540                1545

Arg His Val Phe Glu Val Asp Glu Asn Gly Gln Arg Arg Leu Arg
1550                1555                1560

Ser Thr Glu Val Ile Gln Glu Ala Ile Pro Glu Ile Val Glu Ile
1565                1570                1575

Gly Thr Lys Val Lys Thr Val Pro Ala Val Val Ala Thr Gln Glu
1580                1585                1590
```

```
Lys Pro Ala Gln Asn Thr Ala Val Lys Ser Glu Glu Ala Ser Lys
    1595                1600                1605

Gln Leu Pro Asn Thr Gly Thr Ala Asp Ala Asn Glu Ala Leu Ile
    1610                1615                1620

Ala Gly Leu Ala Ser Leu Gly Leu Ala Ser Leu Ala Leu Thr Leu
    1625                1630                1635

Arg Arg Lys Arg Glu Asp Lys Asp
    1640                1645

<210> SEQ ID NO 7
<211> LENGTH: 913
<212> TYPE: PRT
<213> ORGANISM: Artificial Sequence
<220> FEATURE:
<223> OTHER INFORMATION: Synthetic construct

<400> SEQUENCE: 7

Glu Ser Lys Pro Ala Ala Glu Ala Asn Lys Thr Glu Lys Glu Val Gln
1               5                   10                  15

Pro Asp Val Pro Lys Asn Thr Glu Lys Thr Leu Lys Pro Lys Glu Ile
                20                  25                  30

Lys Phe Asn Ser Trp Glu Glu Leu Leu Lys Trp Glu Pro Gly Ala Arg
            35                  40                  45

Glu Asp Asp Ala Ile Asn Arg Gly Ser Val Val Leu Ala Ser Arg Arg
    50                  55                  60

Thr Gly His Leu Val Asn Glu Lys Ala Ser Lys Ala Lys Val Gln
65              70                  75                  80

Ala Leu Ser Asn Thr Asn Ser Lys Ala Lys Asp His Ala Ser Val Gly
                85                  90                  95

Gly Glu Glu Phe Lys Ala Tyr Ala Phe Asp Tyr Trp Gln Tyr Leu Asp
                100                 105                 110

Ser Met Val Phe Trp Glu Gly Leu Val Pro Thr Pro Asp Val Ile Asp
            115                 120                 125

Ala Gly His Arg Asn Gly Val Pro Val Tyr Gly Thr Leu Phe Phe Asn
    130                 135                 140

Trp Ser Asn Ser Ile Ala Asp Gln Glu Arg Phe Ala Glu Ala Leu Lys
145                 150                 155                 160

Gln Asp Ala Asp Gly Ser Phe Pro Ile Ala Arg Lys Leu Val Asp Met
                165                 170                 175

Ala Lys Tyr Tyr Gly Tyr Asp Gly Tyr Phe Ile Gln Gln Glu Thr Thr
            180                 185                 190

Gly Asp Leu Val Lys Pro Leu Gly Glu Lys Met Arg Gln Phe Met Leu
        195                 200                 205

Tyr Ser Lys Glu Tyr Ala Ala Lys Val Asn His Pro Ile Lys Tyr Ser
    210                 215                 220

Trp Tyr Asp Ala Met Thr Tyr Asn Tyr Gly Arg Tyr His Gln Asp Gly
225                 230                 235                 240

Leu Gly Glu Tyr Asn Tyr Gln Phe Met Gln Pro Glu Gly Asp Lys Val
                245                 250                 255

Pro Ala Asp Asn Phe Phe Ala Asn Phe Asn Trp Asp Lys Ala Lys Asn
            260                 265                 270

Asp Tyr Thr Ile Ala Thr Ala Asn Trp Ile Gly Arg Asn Pro Tyr Asp
        275                 280                 285

Val Phe Ala Gly Leu Glu Leu Gln Gln Gly Gly Ser Tyr Lys Thr Lys
    290                 295                 300
```

```
Val Lys Trp Asn Asp Ile Leu Asp Glu Asn Gly Lys Leu Arg Leu Ser
305                 310                 315                 320

Leu Gly Leu Phe Ala Pro Asp Thr Ile Thr Ser Leu Gly Lys Thr Gly
            325                 330                 335

Glu Asp Tyr His Lys Asn Glu Asp Ile Phe Phe Thr Gly Tyr Gln Gly
            340                 345                 350

Asp Pro Thr Gly Gln Lys Pro Gly Asp Lys Asp Trp Tyr Gly Ile Ala
            355                 360                 365

Asn Leu Val Ala Asp Arg Thr Pro Ala Val Gly Asn Thr Phe Thr Thr
370                 375                 380

Ser Phe Asn Thr Gly His Gly Lys Lys Trp Phe Val Asp Gly Lys Val
385                 390                 395                 400

Ser Lys Asp Ser Glu Trp Asn Tyr Arg Ser Val Ser Gly Val Leu Pro
            405                 410                 415

Thr Trp Arg Trp Trp Gln Thr Ser Thr Gly Glu Lys Leu Arg Ala Glu
            420                 425                 430

Tyr Asp Phe Thr Asp Ala Tyr Asn Gly Gly Asn Ser Leu Lys Phe Ser
            435                 440                 445

Gly Asp Val Ala Gly Lys Thr Asp Gln Asp Val Arg Leu Tyr Ser Thr
450                 455                 460

Lys Leu Glu Val Thr Glu Lys Thr Lys Leu Arg Val Ala His Lys Gly
465                 470                 475                 480

Gly Lys Gly Ser Lys Val Tyr Met Ala Phe Ser Thr Thr Pro Asp Tyr
            485                 490                 495

Lys Phe Asp Asp Ala Asp Ala Trp Lys Glu Leu Thr Leu Ser Asp Asn
            500                 505                 510

Trp Thr Asn Glu Glu Phe Asp Leu Ser Ser Leu Ala Gly Lys Thr Ile
            515                 520                 525

Tyr Ala Val Lys Leu Phe Phe Glu His Glu Gly Ala Val Lys Asp Tyr
530                 535                 540

Gln Phe Asn Leu Gly Gln Leu Thr Ile Ser Asp Asn His Gln Glu Pro
545                 550                 555                 560

Gln Ser Pro Thr Ser Phe Ser Val Val Lys Gln Ser Leu Lys Asn Ala
            565                 570                 575

Gln Glu Ala Glu Ala Val Val Gln Phe Lys Gly Asn Lys Asp Ala Asp
            580                 585                 590

Phe Tyr Glu Val Tyr Glu Lys Asp Gly Asp Ser Trp Lys Leu Leu Thr
            595                 600                 605

Gly Ser Ser Ser Thr Thr Ile Tyr Leu Pro Lys Val Ser Arg Ser Ala
610                 615                 620

Ser Ala Gln Gly Thr Thr Gln Glu Leu Lys Val Val Ala Val Gly Lys
625                 630                 635                 640

Asn Gly Val Arg Ser Glu Ala Ala Thr Thr Thr Phe Asp Trp Gly Met
            645                 650                 655

Thr Val Lys Asp Thr Ser Leu Pro Lys Pro Leu Ala Glu Asn Ile Val
            660                 665                 670

Pro Gly Ala Thr Val Ile Asp Ser Thr Phe Pro Lys Thr Glu Gly Gly
            675                 680                 685

Glu Gly Ile Glu Gly Met Leu Asn Gly Thr Ile Thr Ser Leu Ser Asp
            690                 695                 700

Lys Trp Ser Ser Ala Gln Leu Ser Gly Ser Val Asp Ile Arg Leu Thr
705                 710                 715                 720

Lys Pro Arg Thr Val Val Arg Trp Val Met Asp His Ala Gly Ala Gly
```

```
                    725                 730                 735
Gly Glu Ser Val Asn Asp Gly Leu Met Asn Thr Lys Asp Phe Asp Leu
                740                 745                 750

Tyr Tyr Lys Asp Ala Asp Gly Glu Trp Lys Leu Ala Lys Glu Val Arg
            755                 760                 765

Gly Asn Lys Ala His Val Thr Asp Ile Thr Leu Asp Lys Pro Ile Thr
        770                 775                 780

Ala Gln Asp Trp Arg Leu Asn Val Val Thr Ser Asp Asn Gly Thr Pro
785                 790                 795                 800

Trp Lys Ala Ile Arg Ile Tyr Asn Trp Lys Met Tyr Glu Lys Leu Asp
                805                 810                 815

Thr Glu Ser Val Asn Ile Pro Met Ala Lys Ala Ala Arg Ser Leu
            820                 825                 830

Gly Asn Asn Lys Val Gln Val Gly Phe Ala Asp Val Gln Ala Gly Ala
        835                 840                 845

Thr Ile Thr Val Tyr Asp Asn Pro Asn Ser Gln Thr Pro Leu Ala Thr
    850                 855                 860

Leu Lys Ser Glu Val Gly Gly Asp Leu Ala Ser Ala Pro Leu Asp Leu
865                 870                 875                 880

Thr Asn Gln Ser Gly Leu Leu Tyr Tyr Arg Thr Gln Leu Pro Gly Lys
                885                 890                 895

Glu Ile Ser Asn Val Leu Ala Val Ser Val Pro Lys Asp Asp Arg Arg
            900                 905                 910

Ile

<210> SEQ ID NO 8
<211> LENGTH: 913
<212> TYPE: PRT
<213> ORGANISM: Artificial Sequence
<220> FEATURE:
<223> OTHER INFORMATION: Synthetic Construct

<400> SEQUENCE: 8

Glu Ser Lys Pro Ala Ala Glu Ala Asn Lys Thr Glu Lys Glu Val Gln
1               5                   10                  15

Pro Asp Val Pro Lys Asn Thr Glu Lys Thr Leu Lys Pro Lys Glu Ile
            20                  25                  30

Lys Phe Asn Ser Trp Glu Glu Leu Leu Lys Trp Glu Pro Gly Ala Arg
        35                  40                  45

Glu Asp Asp Ala Ile Asn Arg Gly Ser Val Val Leu Ala Ser Arg Arg
    50                  55                  60

Thr Gly His Leu Val Asn Glu Lys Ala Ser Lys Glu Ala Lys Val Gln
65                  70                  75                  80

Ala Leu Ser Asn Thr Asn Ser Lys Ala Lys Asp His Ala Ser Val Gly
                85                  90                  95

Gly Glu Glu Phe Lys Ala Tyr Ala Phe Asp Tyr Trp Gln Tyr Leu Asp
            100                 105                 110

Ser Met Val Phe Trp Glu Gly Leu Val Pro Thr Pro Asp Val Ile Asp
        115                 120                 125

Ala Gly His Arg Asn Gly Val Pro Val Tyr Gly Thr Leu Phe Phe Asn
    130                 135                 140

Trp Ser Asn Ser Ile Ala Asp Gln Glu Arg Phe Ala Glu Ala Leu Lys
145                 150                 155                 160

Gln Asp Ala Asp Gly Ser Phe Pro Ile Ala Arg Lys Leu Val Asp Met
                165                 170                 175
```

```
Ala Lys Tyr Tyr Gly Tyr Asp Gly Tyr Phe Ile Ala Gln Glu Thr Thr
            180                 185                 190

Gly Asp Leu Val Lys Pro Leu Gly Glu Lys Met Arg Gln Phe Met Leu
            195                 200             205

Tyr Ser Lys Glu Tyr Ala Ala Lys Val Asn His Pro Ile Lys Tyr Ser
        210                 215                 220

Trp Tyr Asp Ala Met Thr Tyr Asn Tyr Gly Arg Tyr His Gln Asp Gly
225                 230                 235                 240

Leu Gly Glu Tyr Asn Tyr Gln Phe Met Gln Pro Gly Asp Lys Val
                245                 250                 255

Pro Ala Asp Asn Phe Phe Ala Asn Phe Asn Trp Asp Lys Ala Lys Asn
                260                 265                 270

Asp Tyr Thr Ile Ala Thr Ala Asn Trp Ile Gly Arg Asn Pro Tyr Asp
        275                 280                 285

Val Phe Ala Gly Leu Glu Leu Gln Gln Gly Gly Ser Tyr Lys Thr Lys
        290                 295                 300

Val Lys Trp Asn Asp Ile Leu Asp Glu Asn Gly Lys Leu Arg Leu Ser
305                 310                 315                 320

Leu Gly Leu Phe Ala Pro Asp Thr Ile Thr Ser Leu Gly Lys Thr Gly
                325                 330                 335

Glu Asp Tyr His Lys Asn Glu Asp Ile Phe Phe Thr Gly Tyr Gln Gly
                340                 345                 350

Asp Pro Thr Gly Gln Lys Pro Gly Asp Lys Asp Trp Tyr Gly Ile Ala
                355                 360                 365

Asn Leu Val Ala Asp Arg Thr Pro Ala Val Gly Asn Thr Phe Thr Thr
            370                 375                 380

Ser Phe Asn Thr Gly His Gly Lys Lys Trp Phe Val Asp Gly Lys Val
385                 390                 395                 400

Ser Lys Asp Ser Glu Trp Asn Tyr Arg Ser Val Ser Gly Val Leu Pro
                405                 410                 415

Thr Trp Arg Trp Trp Gln Thr Ser Thr Gly Glu Lys Leu Arg Ala Glu
            420                 425                 430

Tyr Asp Phe Thr Asp Ala Tyr Asn Gly Gly Asn Ser Leu Lys Phe Ser
                435                 440                 445

Gly Asp Val Ala Gly Lys Thr Asp Gln Asp Val Arg Leu Tyr Ser Thr
        450                 455                 460

Lys Leu Glu Val Thr Glu Lys Thr Lys Leu Arg Val Ala His Lys Gly
465                 470                 475                 480

Gly Lys Gly Ser Lys Val Tyr Met Ala Phe Ser Thr Thr Pro Asp Tyr
                485                 490                 495

Lys Phe Asp Asp Ala Asp Ala Trp Lys Glu Leu Thr Leu Ser Asp Asn
                500                 505                 510

Trp Thr Asn Glu Glu Phe Asp Leu Ser Ser Leu Ala Gly Lys Thr Ile
            515                 520                 525

Tyr Ala Val Lys Leu Phe Phe Glu His Glu Gly Ala Val Lys Asp Tyr
        530                 535                 540

Gln Phe Asn Leu Gly Gln Leu Thr Ile Ser Asp Asn His Gln Glu Pro
545                 550                 555                 560

Gln Ser Pro Thr Ser Phe Ser Val Val Lys Gln Ser Leu Lys Asn Ala
                565                 570                 575

Gln Glu Ala Glu Ala Val Val Gln Phe Lys Gly Asn Lys Asp Ala Asp
                580                 585                 590
```

```
Phe Tyr Glu Val Tyr Glu Lys Asp Gly Asp Ser Trp Lys Leu Leu Thr
            595                 600                 605

Gly Ser Ser Ser Thr Thr Ile Tyr Leu Pro Lys Val Ser Arg Ser Ala
610                 615                 620

Ser Ala Gln Gly Thr Thr Gln Glu Leu Lys Val Val Ala Val Gly Lys
625                 630                 635                 640

Asn Gly Val Arg Ser Glu Ala Ala Thr Thr Phe Asp Trp Gly Met
            645                 650                 655

Thr Val Lys Asp Thr Ser Leu Pro Lys Pro Leu Ala Glu Asn Ile Val
            660                 665                 670

Pro Gly Ala Thr Val Ile Asp Ser Thr Phe Pro Lys Thr Glu Gly Gly
            675                 680                 685

Glu Gly Ile Glu Gly Met Leu Asn Gly Thr Ile Thr Ser Leu Ser Asp
            690                 695                 700

Lys Trp Ser Ser Ala Gln Leu Ser Gly Ser Val Asp Ile Arg Leu Thr
705                 710                 715                 720

Lys Pro Arg Thr Val Val Arg Trp Val Met Asp His Ala Gly Ala Gly
            725                 730                 735

Gly Glu Ser Val Asn Asp Gly Leu Met Asn Thr Lys Asp Phe Asp Leu
            740                 745                 750

Tyr Tyr Lys Asp Ala Asp Gly Glu Trp Lys Leu Ala Lys Glu Val Arg
            755                 760                 765

Gly Asn Lys Ala His Val Thr Asp Ile Thr Leu Asp Lys Pro Ile Thr
            770                 775                 780

Ala Gln Asp Trp Arg Leu Asn Val Val Thr Ser Asp Asn Gly Thr Pro
785                 790                 795                 800

Trp Lys Ala Ile Arg Ile Tyr Asn Trp Lys Met Tyr Glu Lys Leu Asp
            805                 810                 815

Thr Glu Ser Val Asn Ile Pro Met Ala Lys Ala Ala Arg Ser Leu
            820                 825                 830

Gly Asn Asn Lys Val Gln Val Gly Phe Ala Asp Val Gln Ala Gly Ala
            835                 840                 845

Thr Ile Thr Val Tyr Asp Asn Pro Asn Ser Gln Thr Pro Leu Ala Thr
            850                 855                 860

Leu Lys Ser Glu Val Gly Gly Asp Leu Ala Ser Ala Pro Leu Asp Leu
865                 870                 875                 880

Thr Asn Gln Ser Gly Leu Leu Tyr Tyr Arg Thr Gln Leu Pro Gly Lys
            885                 890                 895

Glu Ile Ser Asn Val Leu Ala Val Ser Val Pro Lys Asp Asp Arg Arg
            900                 905                 910

Ile

<210> SEQ ID NO 9
<211> LENGTH: 913
<212> TYPE: PRT
<213> ORGANISM: Artificial Sequence
<220> FEATURE:
<223> OTHER INFORMATION: Synthetic Construct

<400> SEQUENCE: 9

Glu Ser Lys Pro Ala Ala Glu Ala Asn Lys Thr Glu Lys Glu Val Gln
1               5                   10                  15

Pro Asp Val Pro Lys Asn Thr Glu Lys Thr Leu Lys Pro Lys Glu Ile
            20                  25                  30

Lys Phe Asn Ser Trp Glu Glu Leu Leu Lys Trp Glu Pro Gly Ala Arg
```

```
                35                  40                  45
Glu Asp Asp Ala Ile Asn Arg Gly Ser Val Val Leu Ala Ser Arg Arg
 50                  55                  60

Thr Gly His Leu Val Asn Glu Lys Ala Ser Lys Glu Ala Lys Val Gln
 65                  70                  75                  80

Ala Leu Ser Asn Thr Asn Ser Lys Ala Lys Asp His Ala Ser Val Gly
                 85                  90                  95

Gly Glu Glu Phe Lys Ala Tyr Ala Phe Asp Tyr Trp Gln Tyr Leu Asp
                100                 105                 110

Ser Met Val Phe Trp Glu Gly Leu Val Pro Thr Pro Asp Val Ile Asp
                115                 120                 125

Ala Gly His Arg Asn Gly Val Pro Val Tyr Gly Thr Leu Phe Phe Asn
                130                 135                 140

Trp Ser Asn Ser Ile Ala Asp Gln Glu Arg Phe Ala Glu Ala Leu Lys
145                 150                 155                 160

Gln Asp Ala Asp Gly Ser Phe Pro Ile Ala Arg Lys Leu Val Asp Met
                165                 170                 175

Ala Lys Tyr Tyr Gly Tyr Asp Gly Tyr Phe Ile Asn Gln Gln Thr Thr
                180                 185                 190

Gly Asp Leu Val Lys Pro Leu Gly Glu Lys Met Arg Gln Phe Met Leu
                195                 200                 205

Tyr Ser Lys Glu Tyr Ala Ala Lys Val Asn His Pro Ile Lys Tyr Ser
210                 215                 220

Trp Tyr Asp Ala Met Thr Tyr Asn Tyr Gly Arg Tyr His Gln Asp Gly
225                 230                 235                 240

Leu Gly Glu Tyr Asn Tyr Gln Phe Met Gln Pro Gly Asp Lys Val
                245                 250                 255

Pro Ala Asp Asn Phe Phe Ala Asn Phe Asn Trp Asp Lys Ala Lys Asn
                260                 265                 270

Asp Tyr Thr Ile Ala Thr Ala Asn Trp Ile Gly Arg Asn Pro Tyr Asp
                275                 280                 285

Val Phe Ala Gly Leu Glu Leu Gln Gln Gly Gly Ser Tyr Lys Thr Lys
                290                 295                 300

Val Lys Trp Asn Asp Ile Leu Asp Glu Asn Gly Lys Leu Arg Leu Ser
305                 310                 315                 320

Leu Gly Leu Phe Ala Pro Asp Thr Ile Thr Ser Leu Gly Lys Thr Gly
                325                 330                 335

Glu Asp Tyr His Lys Asn Glu Asp Ile Phe Phe Thr Gly Tyr Gln Gly
                340                 345                 350

Asp Pro Thr Gly Gln Lys Pro Gly Asp Lys Asp Trp Tyr Gly Ile Ala
                355                 360                 365

Asn Leu Val Ala Asp Arg Thr Pro Ala Val Gly Asn Thr Phe Thr Thr
                370                 375                 380

Ser Phe Asn Thr Gly His Gly Lys Lys Trp Phe Val Asp Gly Lys Val
385                 390                 395                 400

Ser Lys Asp Ser Glu Trp Asn Tyr Arg Ser Val Ser Gly Val Leu Pro
                405                 410                 415

Thr Trp Arg Trp Trp Gln Thr Ser Thr Gly Lys Leu Arg Ala Glu
                420                 425                 430

Tyr Asp Phe Thr Asp Ala Tyr Asn Gly Gly Asn Ser Leu Lys Phe Ser
                435                 440                 445

Gly Asp Val Ala Gly Lys Thr Asp Gln Asp Val Arg Leu Tyr Ser Thr
450                 455                 460
```

```
Lys Leu Glu Val Thr Glu Lys Thr Lys Leu Arg Val Ala His Lys Gly
465                 470                 475                 480

Gly Lys Gly Ser Lys Val Tyr Met Ala Phe Ser Thr Thr Pro Asp Tyr
                485                 490                 495

Lys Phe Asp Asp Ala Asp Ala Trp Lys Glu Leu Thr Leu Ser Asp Asn
            500                 505                 510

Trp Thr Asn Glu Glu Phe Asp Leu Ser Ser Leu Ala Gly Lys Thr Ile
        515                 520                 525

Tyr Ala Val Lys Leu Phe Phe Glu His Glu Gly Ala Val Lys Asp Tyr
    530                 535                 540

Gln Phe Asn Leu Gly Gln Leu Thr Ile Ser Asp Asn His Gln Glu Pro
545                 550                 555                 560

Gln Ser Pro Thr Ser Phe Ser Val Val Lys Gln Ser Leu Lys Asn Ala
                565                 570                 575

Gln Glu Ala Glu Ala Val Val Gln Phe Lys Gly Asn Lys Asp Ala Asp
            580                 585                 590

Phe Tyr Glu Val Tyr Glu Lys Asp Gly Asp Ser Trp Lys Leu Leu Thr
        595                 600                 605

Gly Ser Ser Ser Thr Thr Ile Tyr Leu Pro Lys Val Ser Arg Ser Ala
    610                 615                 620

Ser Ala Gln Gly Thr Thr Gln Glu Leu Lys Val Val Ala Val Gly Lys
625                 630                 635                 640

Asn Gly Val Arg Ser Glu Ala Ala Thr Thr Thr Phe Asp Trp Gly Met
                645                 650                 655

Thr Val Lys Asp Thr Ser Leu Pro Lys Pro Leu Ala Glu Asn Ile Val
            660                 665                 670

Pro Gly Ala Thr Val Ile Asp Ser Thr Phe Pro Lys Thr Glu Gly Gly
        675                 680                 685

Glu Gly Ile Glu Gly Met Leu Asn Gly Thr Ile Thr Ser Leu Ser Asp
    690                 695                 700

Lys Trp Ser Ser Ala Gln Leu Ser Gly Ser Val Asp Ile Arg Leu Thr
705                 710                 715                 720

Lys Pro Arg Thr Val Val Arg Trp Val Met Asp His Ala Gly Ala Gly
                725                 730                 735

Gly Glu Ser Val Asn Asp Gly Leu Met Asn Thr Lys Asp Phe Asp Leu
            740                 745                 750

Tyr Tyr Lys Asp Ala Asp Gly Glu Trp Lys Leu Ala Lys Glu Val Arg
        755                 760                 765

Gly Asn Lys Ala His Val Thr Asp Ile Thr Leu Asp Lys Pro Ile Thr
    770                 775                 780

Ala Gln Asp Trp Arg Leu Asn Val Val Thr Ser Asp Asn Gly Thr Pro
785                 790                 795                 800

Trp Lys Ala Ile Arg Ile Tyr Asn Trp Lys Met Tyr Glu Lys Leu Asp
                805                 810                 815

Thr Glu Ser Val Asn Ile Pro Met Ala Lys Ala Ala Arg Ser Leu
            820                 825                 830

Gly Asn Asn Lys Val Gln Val Gly Phe Ala Asp Val Gln Ala Gly Ala
        835                 840                 845

Thr Ile Thr Val Tyr Asp Asn Pro Asn Ser Gln Thr Pro Leu Ala Thr
    850                 855                 860

Leu Lys Ser Glu Val Gly Gly Asp Leu Ala Ser Ala Pro Leu Asp Leu
865                 870                 875                 880
```

```
Thr Asn Gln Ser Gly Leu Leu Tyr Tyr Arg Thr Gln Leu Pro Gly Lys
                885                 890                 895

Glu Ile Ser Asn Val Leu Ala Val Ser Val Pro Lys Asp Asp Arg Arg
            900                 905                 910

Ile

<210> SEQ ID NO 10
<211> LENGTH: 104
<212> TYPE: PRT
<213> ORGANISM: Artificial Sequence
<220> FEATURE:
<223> OTHER INFORMATION: Synthetic Construct

<400> SEQUENCE: 10

Glu Gln Glu Glu Asp Gly Ser Phe Pro Leu Ala Asp Lys Leu Leu Glu
1               5                   10                  15

Val Ala Asp Tyr Tyr Gly Phe Asp Gly Trp Phe Ile Asn Gln Glu Thr
            20                  25                  30

Glu Gly Ala Asp Glu Gly Thr Ala Glu Ala Met Gln Ala Phe Leu Val
        35                  40                  45

Tyr Leu Gln Glu Gln Lys Pro Glu Gly Met His Ile Met Trp Tyr Asp
    50                  55                  60

Ser Met Ile Asp Thr Gly Ala Ile Ala Trp Gln Asn His Leu Thr Asp
65                  70                  75                  80

Arg Asn Lys Met Tyr Leu Gln Asn Gly Ser Thr Arg Val Ala Asp Ser
                85                  90                  95

Met Phe Leu Asn Phe Trp Trp Arg
            100

<210> SEQ ID NO 11
<211> LENGTH: 109
<212> TYPE: PRT
<213> ORGANISM: Artificial Sequence
<220> FEATURE:
<223> OTHER INFORMATION: Synthetic Construct

<400> SEQUENCE: 11

Lys Gln Asp Ala Asp Gly Ser Phe Pro Ile Ala Arg Lys Leu Val Asp
1               5                   10                  15

Met Ala Lys Tyr Tyr Gly Tyr Asp Gly Tyr Phe Ile Asn Gln Glu Thr
            20                  25                  30

Thr Gly Asp Leu Val Lys Pro Leu Gly Glu Lys Met Arg Gln Phe Met
        35                  40                  45

Leu Tyr Ser Lys Glu Tyr Ala Ala Lys Val Asn His Pro Ile Lys Tyr
    50                  55                  60

Ser Trp Tyr Asp Ala Met Thr Tyr Asn Tyr Gly Arg Tyr His Gln Asp
65                  70                  75                  80

Gly Leu Gly Glu Tyr Asn Tyr Gln Phe Met Gln Pro Glu Gly Asp Lys
                85                  90                  95

Val Pro Ala Asp Asn Phe Ala Asn Phe Asn Trp Asp
            100                 105

<210> SEQ ID NO 12
<211> LENGTH: 115
<212> TYPE: PRT
<213> ORGANISM: Artificial Sequence
<220> FEATURE:
<223> OTHER INFORMATION: Synthetic Construct

<400> SEQUENCE: 12
```

```
Pro Leu Leu Asn Asn Ala Thr Asp Asp Pro Met Arg Leu Trp Ser Pro
1               5                   10                  15

Tyr Tyr Ala Asp Gln Leu Val Ala Ile Ala Lys His Tyr Gly Phe Asp
            20                  25                  30

Gly Trp Leu Phe Asn Ile Glu Cys Glu Phe Pro Phe Pro Thr Asn
        35                  40                  45

Pro Lys Phe Lys Ala Glu Glu Leu Ala Lys Phe Leu His Tyr Phe Lys
        50                  55                  60

Glu Lys Leu His Asn Glu Ile Pro Gly Ser Gln Leu Ile Trp Tyr Asp
65              70                  75                  80

Ser Met Thr Asn Glu Gly Glu Ile His Trp Gln Asn Gln Leu Thr Trp
                85                  90                  95

Lys Asn Glu Leu Phe Phe Lys Asn Thr Asp Gly Ile Phe Leu Asn Tyr
            100                 105                 110

Trp Trp Lys
        115
```

<210> SEQ ID NO 13
<211> LENGTH: 893
<212> TYPE: PRT
<213> ORGANISM: Artificial Sequence
<220> FEATURE:
<223> OTHER INFORMATION: Synthetic Construct

<400> SEQUENCE: 13

```
Glu Ser Lys Pro Ala Ala Glu Ala Asn Lys Thr Glu Lys Glu Val Gln
1               5                   10                  15

Pro Asp Val Pro Lys Asn Thr Glu Lys Thr Leu Lys Pro Lys Glu Ile
            20                  25                  30

Lys Phe Asn Ser Trp Glu Glu Leu Leu Lys Trp Glu Pro Gly Ala Arg
        35                  40                  45

Glu Asp Asp Ala Ile Asn Arg Gly Ser Val Val Leu Ala Ser Arg Arg
    50                  55                  60

Thr Gly His Leu Val Asn Glu Lys Ala Ser Lys Glu Ala Lys Val Gln
65              70                  75                  80

Ala Leu Ser Asn Thr Asn Ser Lys Ala Lys Asp His Ala Ser Val Gly
                85                  90                  95

Gly Glu Glu Phe Lys Ala Tyr Ala Phe Asp Tyr Trp Gln Tyr Leu Asp
            100                 105                 110

Ser Met Val Phe Trp Glu Gly Leu Val Pro Thr Pro Asp Val Ile Asp
        115                 120                 125

Ala Gly His Arg Asn Gly Val Pro Val Tyr Gly Thr Leu Phe Phe Asn
    130                 135                 140

Trp Ser Asn Ser Ile Ala Asp Gln Glu Arg Phe Ala Glu Ala Leu Lys
145                 150                 155                 160

Gln Asp Ala Asp Gly Ser Phe Pro Ile Ala Arg Lys Leu Val Asp Met
            165                 170                 175

Ala Lys Tyr Tyr Gly Tyr Asp Gly Tyr Phe Ile Asn Gln Glu Thr Thr
        180                 185                 190

Gly Asp Leu Val Lys Pro Leu Gly Glu Lys Met Arg Gln Phe Met Leu
    195                 200                 205

Tyr Ser Lys Glu Tyr Ala Ala Lys Val Asn His Pro Ile Lys Tyr Ser
    210                 215                 220

Trp Phe Asp Ala Met Thr Tyr Asn Tyr Gly Arg Tyr His Gln Asp Gly
225                 230                 235                 240
```

-continued

```
Leu Gly Glu Tyr Asn Tyr Gln Phe Met Gln Pro Gly Asp Lys Val
            245                 250                 255

Pro Ala Asp Asn Phe Phe Ala Asn Phe Asn Trp Asp Lys Ala Lys Asn
                260                 265                 270

Asp Tyr Thr Ile Ala Thr Ala Asn Trp Ile Gly Arg Asn Pro Tyr Asp
            275                 280                 285

Val Phe Ala Gly Leu Glu Leu Gln Gln Gly Ser Tyr Lys Thr Lys
            290                 295                 300

Val Lys Trp Asn Asp Ile Leu Asp Glu Asn Gly Lys Leu Arg Leu Ser
305                 310                 315                 320

Leu Gly Leu Phe Ala Pro Asp Thr Ile Thr Ser Leu Gly Lys Thr Gly
                325                 330                 335

Glu Asp Tyr His Lys Asn Glu Asp Ile Phe Phe Thr Gly Tyr Gln Gly
                340                 345                 350

Asp Pro Thr Gly Gln Lys Pro Gly Asp Lys Asp Trp Tyr Gly Ile Ala
                355                 360                 365

Asn Leu Val Ala Asp Arg Thr Pro Ala Val Gly Asn Thr Phe Thr Thr
            370                 375                 380

Ser Phe Asn Thr Gly His Gly Lys Lys Trp Phe Val Asp Gly Lys Val
385                 390                 395                 400

Ser Lys Asp Ser Glu Trp Asn Tyr Arg Ser Val Ser Gly Val Leu Pro
                405                 410                 415

Thr Trp Arg Trp Trp Gln Thr Ser Thr Gly Glu Lys Leu Arg Ala Glu
                420                 425                 430

Tyr Asp Phe Thr Asp Ala Tyr Asn Gly Gly Asn Ser Leu Lys Phe Ser
                435                 440                 445

Gly Asp Val Ala Gly Lys Thr Asp Gln Asp Val Arg Leu Tyr Ser Thr
            450                 455                 460

Lys Leu Glu Val Thr Glu Lys Thr Lys Leu Arg Val Ala His Lys Gly
465                 470                 475                 480

Gly Lys Gly Ser Lys Val Tyr Met Ala Phe Ser Thr Thr Pro Asp Tyr
                485                 490                 495

Lys Phe Asp Asp Ala Asp Ala Trp Lys Glu Leu Thr Leu Ser Asp Asn
                500                 505                 510

Trp Thr Asn Glu Glu Phe Asp Leu Ser Ser Leu Ala Gly Lys Thr Ile
            515                 520                 525

Tyr Ala Val Lys Leu Phe Phe Glu His Glu Gly Ala Val Lys Asp Tyr
530                 535                 540

Gln Phe Asn Leu Gly Gln Leu Thr Ile Ser Asp Asn His Gln Glu Pro
545                 550                 555                 560

Gln Ser Pro Thr Ser Phe Ser Val Val Lys Gln Ser Leu Lys Asn Ala
                565                 570                 575

Gln Glu Ala Glu Ala Val Val Gln Phe Lys Gly Asn Lys Asp Ala Asp
                580                 585                 590

Phe Tyr Glu Val Tyr Glu Lys Asp Gly Asp Ser Trp Lys Leu Leu Thr
            595                 600                 605

Gly Ser Ser Ser Thr Thr Ile Tyr Leu Pro Lys Val Ser Arg Ser Ala
            610                 615                 620

Ser Ala Gln Gly Thr Thr Gln Glu Leu Lys Val Val Ala Val Gly Lys
625                 630                 635                 640

Asn Gly Val Arg Ser Glu Ala Ala Thr Thr Phe Asp Trp Gly Met
                645                 650                 655
```

```
Thr Val Lys Asp Thr Ser Leu Pro Lys Pro Leu Ala Glu Asn Ile Val
            660                 665                 670

Pro Gly Ala Thr Val Ile Asp Ser Thr Phe Pro Lys Thr Glu Gly Gly
        675                 680                 685

Glu Gly Ile Glu Gly Met Leu Asn Gly Thr Ile Thr Ser Leu Ser Asp
    690                 695                 700

Lys Trp Ser Ser Ala Gln Leu Ser Gly Ser Val Asp Ile Arg Leu Thr
705                 710                 715                 720

Lys Pro Arg Thr Val Arg Trp Val Met Asp His Ala Gly Ala Gly
                725                 730                 735

Gly Glu Ser Val Asn Asp Gly Leu Met Asn Thr Lys Asp Phe Asp Leu
            740                 745                 750

Tyr Tyr Lys Asp Ala Asp Gly Glu Trp Lys Leu Ala Lys Glu Val Arg
        755                 760                 765

Gly Asn Lys Ala His Val Thr Asp Ile Thr Leu Asp Lys Pro Ile Thr
    770                 775                 780

Ala Gln Asp Trp Arg Leu Asn Val Val Thr Ser Asp Asn Gly Thr Pro
785                 790                 795                 800

Trp Lys Ala Ile Arg Ile Tyr Asn Trp Lys Met Tyr Glu Lys Leu Asp
                805                 810                 815

Thr Glu Ser Val Asn Ile Pro Met Ala Lys Ala Ala Arg Ser Leu
            820                 825                 830

Gly Asn Asn Lys Val Gln Val Gly Phe Ala Asp Val Gln Ala Gly Ala
        835                 840                 845

Thr Ile Thr Val Tyr Asp Asn Pro Asn Ser Gln Thr Pro Leu Ala Thr
    850                 855                 860

Leu Lys Ser Glu Val Gly Gly Asp Leu Ala Ser Ala Pro Leu Asp Leu
865                 870                 875                 880

Thr Asn Gln Ser Gly Leu Leu Tyr Tyr Arg Thr Gln Leu
                885                 890

<210> SEQ ID NO 14
<211> LENGTH: 893
<212> TYPE: PRT
<213> ORGANISM: Artificial Sequence
<220> FEATURE:
<223> OTHER INFORMATION: Synthetic Construct

<400> SEQUENCE: 14

Glu Ser Lys Pro Ala Ala Glu Ala Asn Lys Thr Glu Lys Glu Val Gln
1               5                   10                  15

Pro Asp Val Pro Lys Asn Thr Glu Lys Thr Leu Lys Pro Lys Glu Ile
            20                  25                  30

Lys Phe Asn Ser Trp Glu Glu Leu Leu Lys Trp Glu Pro Gly Ala Arg
        35                  40                  45

Glu Asp Asp Ala Ile Asn Arg Gly Ser Val Val Leu Ala Ser Arg Arg
    50                  55                  60

Thr Gly His Leu Val Asn Glu Lys Ala Ser Lys Glu Ala Lys Val Gln
65                  70                  75                  80

Ala Leu Ser Asn Thr Asn Ser Lys Ala Lys Asp His Ala Ser Val Gly
                85                  90                  95

Gly Glu Glu Phe Lys Ala Tyr Ala Phe Asp Tyr Trp Gln Tyr Leu Asp
            100                 105                 110

Ser Met Val Phe Trp Glu Gly Leu Val Pro Thr Pro Asp Val Ile Asp
        115                 120                 125
```

Ala Gly His Arg Asn Gly Val Pro Val Tyr Gly Thr Leu Phe Phe Asn
130                 135                 140

Trp Ser Asn Ser Ile Ala Asp Gln Glu Arg Phe Ala Glu Ala Leu Lys
145                 150                 155                 160

Gln Asp Ala Asp Gly Ser Phe Pro Ile Ala Arg Lys Leu Val Asp Met
            165                 170                 175

Ala Lys Tyr Tyr Gly Tyr Asp Gly Tyr Phe Ile Asn Gln Glu Thr Thr
        180                 185                 190

Gly Asp Leu Val Lys Pro Leu Gly Glu Lys Met Arg Gln Phe Met Leu
    195                 200                 205

Tyr Ser Lys Glu Tyr Ala Ala Lys Val Asn His Pro Ile Lys Tyr Ser
210                 215                 220

Trp Tyr Asp Ala Met Thr Tyr Asn Tyr Gly Arg Tyr Trp Gln Asp Gly
225                 230                 235                 240

Leu Gly Glu Tyr Asn Tyr Gln Phe Met Gln Pro Glu Gly Asp Lys Val
            245                 250                 255

Pro Ala Asp Asn Phe Phe Ala Asn Phe Asn Trp Asp Lys Ala Lys Asn
        260                 265                 270

Asp Tyr Thr Ile Ala Thr Ala Asn Trp Ile Gly Arg Asn Pro Tyr Asp
    275                 280                 285

Val Phe Ala Gly Leu Glu Leu Gln Gln Gly Gly Ser Tyr Lys Thr Lys
290                 295                 300

Val Lys Trp Asn Asp Ile Leu Asp Glu Asn Gly Lys Leu Arg Leu Ser
305                 310                 315                 320

Leu Gly Leu Phe Ala Pro Asp Thr Ile Thr Ser Leu Gly Lys Thr Gly
            325                 330                 335

Glu Asp Tyr His Lys Asn Glu Asp Ile Phe Phe Thr Gly Tyr Gln Gly
        340                 345                 350

Asp Pro Thr Gly Gln Lys Pro Gly Asp Lys Asp Trp Tyr Gly Ile Ala
    355                 360                 365

Asn Leu Val Ala Asp Arg Thr Pro Ala Val Gly Asn Thr Phe Thr Thr
370                 375                 380

Ser Phe Asn Thr Gly His Gly Lys Lys Trp Phe Val Asp Gly Lys Val
385                 390                 395                 400

Ser Lys Asp Ser Glu Trp Asn Tyr Arg Ser Val Ser Gly Val Leu Pro
            405                 410                 415

Thr Trp Arg Trp Trp Gln Thr Ser Thr Gly Glu Lys Leu Arg Ala Glu
        420                 425                 430

Tyr Asp Phe Thr Asp Ala Tyr Asn Gly Gly Asn Ser Leu Lys Phe Ser
    435                 440                 445

Gly Asp Val Ala Gly Lys Thr Asp Gln Asp Val Arg Leu Tyr Ser Thr
450                 455                 460

Lys Leu Glu Val Thr Glu Lys Thr Lys Leu Arg Val Ala His Lys Gly
465                 470                 475                 480

Gly Lys Gly Ser Lys Val Tyr Met Ala Phe Ser Thr Thr Pro Asp Tyr
            485                 490                 495

Lys Phe Asp Asp Ala Asp Ala Trp Lys Glu Leu Thr Leu Ser Asp Asn
        500                 505                 510

Trp Thr Asn Glu Glu Phe Asp Leu Ser Ser Leu Ala Gly Lys Thr Ile
    515                 520                 525

Tyr Ala Val Lys Leu Phe Phe Glu His Glu Gly Ala Val Lys Asp Tyr
530                 535                 540

Gln Phe Asn Leu Gly Gln Leu Thr Ile Ser Asp Asn His Gln Glu Pro

```
            545                 550                 555                 560
    Gln Ser Pro Thr Ser Phe Ser Val Val Lys Gln Ser Leu Lys Asn Ala
                    565                 570                 575

Gln Glu Ala Glu Ala Val Val Gln Phe Lys Gly Asn Lys Asp Ala Asp
                580                 585                 590

Phe Tyr Glu Val Tyr Glu Lys Asp Gly Asp Ser Trp Lys Leu Leu Thr
                595                 600                 605

Gly Ser Ser Thr Thr Ile Tyr Leu Pro Lys Val Ser Arg Ser Ala
            610                 615                 620

Ser Ala Gln Gly Thr Thr Gln Glu Leu Lys Val Val Ala Val Gly Lys
    625                 630                 635                 640

Asn Gly Val Arg Ser Glu Ala Ala Thr Thr Phe Asp Trp Gly Met
                    645                 650                 655

Thr Val Lys Asp Thr Ser Leu Pro Lys Pro Leu Ala Glu Asn Ile Val
                    660                 665                 670

Pro Gly Ala Thr Val Ile Asp Ser Thr Phe Pro Lys Thr Glu Gly Gly
                675                 680                 685

Glu Gly Ile Glu Gly Met Leu Asn Gly Thr Ile Thr Ser Leu Ser Asp
            690                 695                 700

Lys Trp Ser Ser Ala Gln Leu Ser Gly Ser Val Asp Ile Arg Leu Thr
    705                 710                 715                 720

Lys Pro Arg Thr Val Arg Trp Val Met Asp His Ala Gly Ala Gly
                    725                 730                 735

Gly Glu Ser Val Asn Asp Gly Leu Met Asn Thr Lys Asp Phe Asp Leu
                740                 745                 750

Tyr Tyr Lys Asp Ala Asp Gly Glu Trp Lys Leu Ala Lys Glu Val Arg
                755                 760                 765

Gly Asn Lys Ala His Val Thr Asp Ile Thr Leu Asp Lys Pro Ile Thr
                770                 775                 780

Ala Gln Asp Trp Arg Leu Asn Val Val Thr Ser Asp Asn Gly Thr Pro
    785                 790                 795                 800

Trp Lys Ala Ile Arg Ile Tyr Asn Trp Lys Met Tyr Glu Lys Leu Asp
                    805                 810                 815

Thr Glu Ser Val Asn Ile Pro Met Ala Lys Ala Ala Arg Ser Leu
                820                 825                 830

Gly Asn Asn Lys Val Gln Val Gly Phe Ala Asp Val Gln Ala Gly Ala
                835                 840                 845

Thr Ile Thr Val Tyr Asp Asn Pro Asn Ser Gln Thr Pro Leu Ala Thr
    850                 855                 860

Leu Lys Ser Glu Val Gly Gly Asp Leu Ala Ser Ala Pro Leu Asp Leu
    865                 870                 875                 880

Thr Asn Gln Ser Gly Leu Leu Tyr Tyr Arg Thr Gln Leu
                    885                 890

<210> SEQ ID NO 15
<211> LENGTH: 649
<212> TYPE: PRT
<213> ORGANISM: Artificial Sequence
<220> FEATURE:
<223> OTHER INFORMATION: Synthetic Construct

<400> SEQUENCE: 15

Lys Thr Leu Lys Pro Lys Glu Ile Lys Phe Asn Ser Trp Glu Leu
1               5                   10                  15

Leu Lys Trp Glu Pro Gly Ala Arg Glu Asp Asp Ala Ile Asn Arg Gly
```

-continued

```
                20                  25                  30
Ser Val Val Leu Ala Ser Arg Arg Thr Gly His Leu Val Asn Glu Lys
                    35                  40                  45
Ala Ser Lys Glu Ala Lys Val Gln Ala Leu Ser Asn Thr Asn Ser Lys
 50                  55                  60
Ala Lys Asp His Ala Ser Val Gly Gly Glu Phe Lys Ala Tyr Ala
 65                  70                  75                  80
Phe Asp Tyr Trp Gln Tyr Leu Asp Ser Met Val Phe Trp Gly Leu
                    85                  90                  95
Val Pro Thr Pro Asp Val Ile Asp Ala Gly His Arg Asn Gly Val Pro
                    100                 105                 110
Val Tyr Gly Thr Leu Phe Phe Asn Trp Ser Asn Ser Ile Ala Asp Gln
                    115                 120                 125
Glu Arg Phe Ala Glu Ala Leu Lys Gln Asp Ala Asp Gly Ser Phe Pro
 130                 135                 140
Ile Ala Arg Lys Leu Val Asp Met Ala Lys Tyr Tyr Gly Tyr Asp Gly
 145                 150                 155                 160
Tyr Phe Ile Asn Gln Glu Thr Thr Gly Asp Leu Val Lys Pro Leu Gly
                    165                 170                 175
Glu Lys Met Arg Gln Phe Met Leu Tyr Ser Lys Glu Tyr Ala Ala Lys
                    180                 185                 190
Val Asn His Pro Ile Lys Tyr Ser Trp Tyr Asp Ala Met Thr Tyr Asn
                    195                 200                 205
Tyr Gly Arg Tyr His Gln Asp Gly Leu Gly Glu Tyr Asn Tyr Gln Phe
                    210                 215                 220
Met Gln Pro Glu Gly Asp Lys Val Pro Ala Asp Asn Phe Phe Ala Asn
 225                 230                 235                 240
Phe Asn Trp Asp Lys Ala Lys Asn Asp Tyr Thr Ile Ala Thr Ala Asn
                    245                 250                 255
Trp Ile Gly Arg Asn Pro Tyr Asp Val Phe Ala Gly Leu Glu Leu Gln
                    260                 265                 270
Gln Gly Gly Ser Tyr Lys Thr Lys Val Lys Trp Asn Asp Ile Leu Asp
                    275                 280                 285
Glu Asn Gly Lys Leu Arg Leu Ser Leu Gly Leu Phe Ala Pro Asp Thr
                    290                 295                 300
Ile Thr Ser Leu Gly Lys Thr Gly Glu Asp Tyr His Lys Asn Glu Asp
 305                 310                 315                 320
Ile Phe Phe Thr Gly Tyr Gln Gly Asp Pro Thr Gly Gln Lys Pro Gly
                    325                 330                 335
Asp Lys Asp Trp Tyr Gly Ile Ala Asn Leu Val Ala Asp Arg Thr Pro
                    340                 345                 350
Ala Val Gly Asn Thr Phe Thr Thr Ser Phe Asn Thr Gly His Gly Lys
                    355                 360                 365
Lys Trp Phe Val Asp Gly Lys Val Ser Lys Asp Ser Glu Trp Asn Tyr
                    370                 375                 380
Arg Ser Val Ser Gly Val Leu Pro Thr Trp Arg Trp Gln Thr Ser
 385                 390                 395                 400
Thr Gly Glu Lys Leu Arg Ala Glu Tyr Asp Phe Thr Asp Ala Tyr Asn
                    405                 410                 415
Gly Gly Asn Ser Leu Lys Phe Ser Gly Asp Val Ala Gly Lys Thr Asp
                    420                 425                 430
Gln Asp Val Arg Leu Tyr Ser Thr Lys Leu Glu Val Thr Glu Lys Thr
                    435                 440                 445
```

```
Lys Leu Arg Val Ala His Lys Gly Gly Lys Gly Ser Lys Val Tyr Met
            450                 455                 460

Ala Phe Ser Thr Thr Pro Asp Tyr Lys Phe Asp Ala Asp Ala Trp
465                 470                 475                 480

Lys Glu Leu Thr Leu Ser Asp Asn Trp Thr Asn Glu Glu Phe Asp Leu
                485                 490                 495

Ser Ser Leu Ala Gly Lys Thr Ile Tyr Ala Val Lys Leu Phe Phe Glu
                500                 505                 510

His Glu Gly Ala Val Lys Asp Tyr Gln Phe Asn Leu Gly Gln Leu Thr
                515                 520                 525

Ile Ser Asp Asn His Gln Glu Pro Gln Ser Pro Thr Ser Phe Ser Val
                530                 535                 540

Val Lys Gln Ser Leu Lys Asn Ala Gln Glu Ala Glu Ala Val Val Gln
545                 550                 555                 560

Phe Lys Gly Asn Lys Asp Ala Asp Phe Tyr Glu Val Tyr Glu Lys Asp
                565                 570                 575

Gly Asp Ser Trp Lys Leu Leu Thr Gly Ser Ser Ser Thr Thr Ile Tyr
                580                 585                 590

Leu Pro Lys Val Ser Arg Ser Ala Ser Ala Gln Gly Thr Thr Gln Glu
                595                 600                 605

Leu Lys Val Val Ala Val Gly Lys Asn Gly Val Arg Ser Glu Ala Ala
610                 615                 620

Thr Thr Thr Phe Asp Trp Gly Met Thr Val Lys Asp Thr Ser Leu Pro
625                 630                 635                 640

Lys Pro Leu Ala Glu Asn Ile Val Pro
                645

<210> SEQ ID NO 16
<211> LENGTH: 35
<212> TYPE: PRT
<213> ORGANISM: Artificial Sequence
<220> FEATURE:
<223> OTHER INFORMATION: Synthetic Construct

<400> SEQUENCE: 16

Thr Ala Thr Ala Thr Ala Cys Ala Thr Ala Thr Gly Gly Ala Gly Thr
1               5                   10                  15

Cys Thr Ala Ala Ala Cys Cys Ala Gly Cys Ala Gly Cys Ala Gly Ala
                20                  25                  30

Ala Gly Cys
        35

<210> SEQ ID NO 17
<211> LENGTH: 36
<212> TYPE: PRT
<213> ORGANISM: Artificial Sequence
<220> FEATURE:
<223> OTHER INFORMATION: Synthetic Construct

<400> SEQUENCE: 17

Gly Cys Gly Cys Gly Cys Cys Thr Cys Gly Ala Gly Thr Thr Cys Thr
1               5                   10                  15

Thr Cys Thr Gly Thr Cys Ala Thr Cys Thr Thr Thr Thr Gly Gly Ala
                20                  25                  30

Ala Cys Gly Gly
        35
```